(12) United States Patent
Akada

(10) Patent No.: US 10,023,836 B2
(45) Date of Patent: Jul. 17, 2018

(54) MEDIUM FOR YEASTS

(71) Applicants: YAMAGUCHI UNIVERSITY, Yamaguchi (JP); KOHJIN LIFE SCIENCES CO., LTD., Tokyo (JP)

(72) Inventor: Rinji Akada, Yamaguchi (JP)

(73) Assignees: YAMAGUCHI UNIVERSITY, Yamaguchi (JP); KOHJIN LIFE SCIENCES CO., LTD., Tokyo (JP)

(*) Notice: Subject to any disclaimer, the term of this patent is extended or adjusted under 35 U.S.C. 154(b) by 270 days.

(21) Appl. No.: 14/423,292

(22) PCT Filed: Aug. 23, 2013

(86) PCT No.: PCT/JP2013/073238
§ 371 (c)(1),
(2) Date: Feb. 23, 2015

(87) PCT Pub. No.: WO2014/030774
PCT Pub. Date: Feb. 27, 2014

(65) Prior Publication Data
US 2015/0299647 A1    Oct. 22, 2015

(30) Foreign Application Priority Data
Aug. 24, 2012 (JP) .................... 2012-184774

(51) Int. Cl.
*C12N 1/16* (2006.01)

(52) U.S. Cl.
CPC ..................... *C12N 1/16* (2013.01)

(58) Field of Classification Search
CPC ........................................ C12N 1/16
See application file for complete search history.

(56) References Cited

U.S. PATENT DOCUMENTS 4,623,626 A * 11/1986 Kusakabe ............ C12N 9/0022
435/191

FOREIGN PATENT DOCUMENTS

| JP | 63-500494 | 2/1988 |
|---|---|---|
| JP | 01-141591 | 6/1989 |
| JP | 03-262481 | 11/1991 |
| JP | 06-225784 | 8/1994 |
| JP | 2004-298139 | 10/2004 |
| JP | 2006-34214 | 2/2006 |
| JP | 2007-252342 | 10/2007 |

OTHER PUBLICATIONS

Deesuth, O, et al "Optimization of Nitrogen and Metal Ions Supplementation for Very High Gravity Bioethanol Fermentation from Sweet Sorghum Juice Using an Orthogonal Array Design" Energies, 2012,5, pp. 3178-3197; doi:10.3390/en5093178.*

Ishmayana, S et al "Preliminary Evidence of Inositol Supplementation Effect on Cell Growth, Viability and Plasma Membrane Fluidity of the Yeast *Saccharomyces cerevisiae*" Procedia Chemistry, 2015,17, pp. 162-169; doi:10.1016/j.proche.2015.12.106.*

Amri M.A. et al., "Growth and Flocculation of Two *Saccharomyces uvarum* Strains", European Journal of Applied Microbiology and Biotechnology, 1979, pp. 227-234, vol. 7.

Yasuyuki Suehara, "Effect of Vitamins on Mycelium Formation in *Candida albicans*", The Journal of Fukuoka Dental College, 1995, pp. 25-31, vol. 22, No. 1.

Search report from PCT/JP2013/073238, dated Nov. 5, 2013.

* cited by examiner

*Primary Examiner* — Christopher R Tate
*Assistant Examiner* — Aaron J Kosar
(74) *Attorney, Agent, or Firm* — Greenblum & Bernstein P.L.C.

(57) ABSTRACT

In order to provide a culture medium eliminating variation by lot of component concentrations, the present invention provides a culture medium, and preferably a chemical-synthetic culture medium, imparting a proliferation ability to yeast that is equivalent to or greater than that of a YPD culture medium. A culture medium is provided which includes sugars as a carbon source capable of being assimilated by yeast; amino acids as a nitrogen source; vitamins; inositol; zinc ion ($Zn^{2+}$); potassium ion ($K^+$), and magnesium ion ($Mg^{2+}$), and in which inositol concentration is between 50 and 10,000 mg/L.

12 Claims, 43 Drawing Sheets

OD change over time

After 2 days

Final OD$_{600}$
YPD: 14, AYD: 15, SD 4.

Final OD$_{600}$
YPD: 30, AYD: 39, SD 12.

MEDIUM FOR YEASTS

FIELD OF THE INVENTION

The present invention relates to a yeast culture medium, and to a yeast culture method in which the yeast is cultivated in the yeast culture medium under aerobic conditions.

BACKGROUND OF THE INVENTION

A culture medium in which an organism capable of being cultivated, such as a microorganism or cultured cell, is cultivated can be divided into two broad categories: rich mediums and synthetic mediums. Efficiency of proliferation of the microorganisms and of production of useful substances is often greatly influenced by the composition of the culture medium, which is deemed to be critically important. It is commonly known that a culture medium in which microorganisms are cultivated is configured by a carbon source, a nitrogen source, minerals, vitamins, a specified growth factor, and the like. A rich medium is believed to be ideal for proliferation, whereas a synthetic medium where categories and concentrations of individual chemical substances are known is believed to be incapable of surpassing a rich medium in proliferation.

Conventionally, a YPD culture medium has been widely used as a rich medium used to cultivate yeast, the YPD culture medium being configured by 1% yeast extract, 2% peptone (partial fragment of casein), and 2% dextrose (equivalent to glucose). However, the YPD culture medium is expensive. Therefore, a majority of the usage of the YPD culture medium in typical corporations is between a research phase and a pilot plant phase. However, chemical components configuring the YPD culture medium are not known in specific detail because the YPD culture medium includes natural extracts in its composition, and there is variation in components between production lots. As a result, sizable variation in organic activity such as proliferation and fermentation may occur between lots. During large-scale fermentation production, an inexpensive molasses is almost always used; however, in recent years an upward trend in costs for molasses has been observed, and an inexpensive culture medium to replace molasses has been sought.

Meanwhile, a YNB culture medium (Yeast Nitrogen Base) manufactured in 1946 by Wickerham can be obtained at low cost as a synthetic medium used to cultivate yeast, and is therefore still widely used in research investigating nutritional requirements of mutant strains or the like. However, proliferation speed when cultivating yeast is slow as compared to a rich medium, and therefore the YNB culture medium is not utilized in large-scale fermentation production or the like. In addition, although the structural components thereof are precisely known, what role the structural components play in proliferation and fermentation is unclear. In addition, an MM culture medium, for example, in which 0.5% $(NH_4)_2SO_4$ and 2% glucose are added to 0.67% YNB culture medium without amino acids and without ammonium sulfate is used as a synthetic medium for experimentation.

Other examples of a yeast culture medium may include an agar-agar culture medium for separation and identification of a high ethanol productivity soy sauce fermentative yeast strain which includes between 3.5 and 10% (w/v) glucose and between 0.8 and 1.2% (w/v) manganese chloride, and does not include 1% (w/v) or more of table salt, in a yeast nutrient culture medium (see, for example, Patent Literature 1); a culture medium for inducing expression of a foreign gene product in a yeast cell, the culture medium including a casamino acid having a concentration of between 20 and 160 g/L (see, for example, Patent Literature 2); a 4-hydroxy-2(or 5)-ethyl-5(or 2)-methyl-3(2H)furanone producing culture medium composition in which pentose (as a carbon source) and amino acid (as a nitrogen source) are at least combined (see, for example, Patent Literature 3); a culture medium which is a differential or selective medium for *Zygosaccharomyces bailii* and *Zygosaccharomyces bisporus* yeasts, the culture medium including a basic inorganic culture medium supplemented by, for example, vitamins such as myo-inositol 4.0% (w/v), trace elements, glucose and formic acid as sole carbon and energy sources, an adapted acid-base indicator, and (as desired) an antibiotic bacteriostatic agent and agar-agar (see, for example, Patent Literature 4); a lactic acid producing culture medium producing lactic acid by fermentation which cultivates microorganisms including yeast having lactic acid synthesizing abilities, the culture medium including between 10 µg/L and 70 µg/L of folic acid or folic acid precursor (see, for example, Patent Literature 5); a yeast culture medium in a liquid, the culture medium being configured by oleic acid, lactic acid, palmitic acid, glutamic acid, citric acid, potassium ion, calcium ion, zinc ion, iron (ii) ion, manganese ion, biotin, thiamine, pyridoxine, inositol, nicotinamide, folic acid, riboflavin, and choline ion, and not including yeast extract (see, for example, Patent Literature 6); and a method of cultivating eukaryotic cells, including yeast cells and plant cells, using a dry powder cultivation culture medium in which pH is automatically adjusted (see, for example, Patent Literature 7).

Examples of a completely synthetic medium for microorganism or cell proliferation may include a completely synthetic medium for mammalian fibroblasts in which polyvinylpyrrolidone, ascorbic acid phosphate, lipids, and cholesterol have been added to a basic culture medium containing human recombinant epithelial cell growth factor or the like (see, for example, Patent Literature 8); and a completely synthetic non-blood serum medium for cultivating human frozen primary hepatocytes after melting, the culture medium containing glucocorticoid, prolactin, cholera toxin, and hepatocyte growth factor (see, for example, Patent Literature 9). Another example is a method of producing a useful chemical compound that includes various steps of fermenting microorganism strains on an industrial scale in a chemically precise fermentation culture medium configured by essentially chemically precise structural components; and collecting the useful chemical compound from the fermentation culture solution, the chemically precise structural components of the chemically precise culture medium being a carbon source selected from a group configured by carbohydrates such as glucose, lactose, fructose, sucrose, maltodextrin, starch, and inulin; glycerin; vegetable oil; hydrocarbons; alcohols such as methanol and ethanol; and organic acids such as acetate and a higher-quality alkanoic acid, and a nitrogen source selected from a group configured by urea; ammonia; nitrate; ammonium salts such as ammonium sulfate, ammonium phosphate, and ammonium nitrate; and amino acids such as glutamate and lysine (see, for example, Patent Literature 10).

With respect to yeast proliferation, additional examples may include a method of promoting yeast proliferation in which a lipid and protein complex is added to a culture medium (see, for example, Patent Literature 11); a culture medium containing a fungal proliferation promotion composition that contains β-glucan as an active ingredient (see, for example, Patent Literature 12); a microorganism proliferation promotion composition containing a glucose supply source and apiose, and including a fungus such as yeast that contains one part or more of apiose per 100 parts glucose (see, for example, Patent Literature 13); and a yeast culture medium in which a flavonoid identified as a factor promoting proliferation of yeast in molasses is chemically synthesized and added, the culture medium not using molasses-derived components intended to reinforce high sugar dough fermentation activity (see, for example, Patent Literature 14).

RELATED ART

Patent Literature

Patent Literature 1: Japanese Patent No. 3904187
Patent Literature 2: Japanese Patent Publication No. H07-106141
Patent Literature 3: Japanese Patent Laid-open Publication No. 2001-120293
Patent Literature 4: Japanese Publication of PCT International Application No. 2003-501047
Patent Literature 5: Japanese Patent Laid-open Publication No. 2008-301766
Patent Literature 6: Japanese Publication of PCT International Application No. 2005-503784
Patent Literature 7: Japanese Patent Laid-open Publication No. 2009-165485
Patent Literature 8: Japanese Patent Laid-open Publication No. 2006-158388
Patent Literature 9: Japanese Patent Laid-open Publication No. 2002-233399
Patent Literature 10: Japanese Patent Laid-open Publication No. 2008-200053
Patent Literature 11: Japanese Patent Laid-open Publication No. 2006-081446
Patent Literature 12: Japanese Patent Laid-open Publication No. 2009-148201
Patent Literature 13: Japanese Patent Laid-open Publication No. 2008-245602
Patent Literature 14: Japanese Patent Laid-open Publication No. 2007-252342

SUMMARY OF THE INVENTION

Problems to be Solved by the Invention

In searching for a baker's yeast having a high level of fermentation ability, a YPD culture medium that is currently in common use is known to have component concentrations that vary by lot, and as a result to have biological activity (such as proliferation) that fluctuates greatly by lot. Accordingly, the YPD culture medium requires investigation of differences in results for each lot, and time and effort must be expended in order to select a superior lot. Therefore, a culture medium which eliminates variation by lot of component concentrations is desired.

The present invention provides a culture medium, and preferably a chemical-synthetic culture medium, imparting a proliferation ability to yeast that is equivalent to or greater than that of a YPD culture medium.

Means for Solving the Problems

First, the inventors of the present invention focused attention on a marked reduction in pH when yeast is cultured in a culture medium to which ammonium sulfate, which is widely used as a nitrogen source, has been added; the inventors of the present invention then investigated proliferation by substituting an amino acid for ammonium sulfate. As a result, a culture medium could be produced having a level of proliferation markedly higher than in a case where ammonium sulfate is added. However, the culture medium was unable to attain a level of proliferation rivaling that of the YPD culture medium, and therefore a further investigation was conducted into whether a useful component not included in existing synthetic mediums was present in a yeast extract fluid contained in the YPD culture medium, the component being useful for increasing proliferation. However, no specific factor dramatically increasing proliferation could be found. Given this, components believed to be particularly useful for proliferation were investigated by dropping one or more structural components from the existing chemical-synthetic medium, and the inventors of the present invention confirmed that several components were essential to yeast growth, and that several components were either not necessary or were detrimental to yeast growth. In addition, manganese, copper, boric acid, sodium, molybdenum, folic acid, PABA, and riboflavin, which are added to YNB, were confirmed to have no particularly positive effect on yeast proliferation. However, proliferation fell when no amino acid whatsoever was added, but even when amino acids were dropped one at a time, the amino acid causing the reduction in proliferation could not be identified, and so the inventors of the present invention could only conjecture that amino acid contributed to yeast proliferation by combination with structural components. Thus, determining a configuration of components for a culture medium having proliferation equivalent to YPD was extremely difficult. However, continuing with subsequent trial-and-error, surprisingly, when approximately 500 times an amount of an MM culture medium (a composition in which 0.5% ammonium sulfate as a nitrogen source and 2% glucose as a carbon source were added to 0.17% YNB (free of amino acid, ammonium sulfate, and glucose) (Y2030, "Yeast Nitrogen Base w/o AA, carbohydrate & w/o AS", manufactured by US Biological Co.)), which is widely used to cultivate yeast, was added to myo-inositol, proliferation equivalent to that of the YPD culture medium was confirmed to be exhibited. An additive amount of other structural components such that myo-inositol would be a rate-limiting step was investigated, a configuration of components having a culture medium having proliferation equivalent to that of YPD was determined, and the present invention was finalized.

Specifically, the present invention relates to: (1) A yeast culture medium that includes sugars as a carbon source capable of being assimilated by yeast; amino acids as a nitrogen source; vitamins; inositol; zinc ion ($Zn^{2+}$); potassium ion ($K^+$), and magnesium ion ($Mg^{2+}$), and in which inositol concentration is between 50 and 10,000 mg/L; (2) The yeast culture medium according to (1) in which the inositol is a proliferation limiting factor; (3) The yeast culture medium according to (1) or (2) that further includes, as the nitrogen source, one or more nucleic acid bases selected from adenine, uracil, guanine, cytosine, and thymine; (4) The yeast culture medium according to any one of (1) to (3) in which aspartic acid is included as the amino acid serving as the nitrogen source; (5) The yeast culture medium according to any one of (1) to (3) in which at least three are selected from aspartic acid, arginine, lysine, proline, glutamic acid, alanine, isoleucine, phenylalanine, valine, tyrosine, methionine, serine, threonine, glycine, asparagine, glutamine, cysteine, leucine, tryptophan, and histidine as the amino acid serving as the nitrogen source; (6) The yeast culture medium according to (5) in which acetyl tyrosine is included instead of tyrosine; (7) The yeast culture medium according to any one of (1) to (6) in which ammonium sulfate is not included as the nitrogen source; (8) The yeast culture medium according to any one of (1) to (7) in which ammonium chloride is not included as the nitrogen source; (9) The yeast culture medium according to any one of (1) to (8) in which ammonium acetate is not included as the nitrogen source; (10) The yeast culture medium according to any one of (1) to (9) that includes at least two selected from biotin, pantothenic acid, niacin, pyridoxine, and thiamine as the vitamin; (11) The yeast culture medium according to (10) in which β-alanine is included instead of pantothenic acid; (12) The yeast culture medium according to any one of (1) to (11) that includes one or more sugars selected from glucose, lactose, mannose, fructose, sucrose, maltose, and raffinose as the carbon source capable of assimilated by yeast; (13) The yeast culture medium according to any one of (1) to (12) in which yeast extract is not included; (14) The yeast culture medium according to any one of (1) to (13) in which, in a case where proliferation of *Saccharomyces cerevisie* RAK3599 strain yeast after 24 hours is indicated by $OD_{600}$, an $OD_{600}$ value is equal to or greater than 80% that of the YPD culture medium; and (15) The yeast culture medium according to (14) in which the $OD_{600}$ value is equal to or greater than 90% that of the YPD culture medium.

In addition, the present invention relates to (16) The yeast culture medium according to any one of (1) to (15) in which the yeast belongs to any one of *Candida* genus, *Kluyveromyces* genus, *Pichia* genus, *Saccharomyces* genus, and *Schizosaccharomyces* genus; (17) The yeast culture medium according to (16) in which the yeast belongs to the *Saccharomyces* genus, and pantothenic acid and biotin are included as vitamins; (18) The yeast culture medium according to (16) in which the yeast belongs to the *Kluyveromyces* genus, and pantothenic acid, biotin, and niacin are included as vitamins; and (19) The yeast culture medium according to (16) in which the yeast belongs to the *Candida* genus, and one or more selected from pyridoxine, biotin, pantothenic acid, thiamine, and niacin are included as vitamins.

Moreover, the present invention relates to (20) An AYD yeast culture medium having a culture medium composition shown in Table 1, below.

TABLE 1

| Structural Component | Concentration | Structural Component | Concentration |
|---|---|---|---|
| Glucose | 20 g/L | Asparagine | 0.5 g/L |
| $KH_2PO_4$ | 1 g/L | Glutamine | 5 g/L |
| $MgSO_4 \cdot 7H_2O$ | 0.5 g/L | Cysteine | 0.01 g/L |
| Aspartic acid | 5 g/L | Leucine | 1 g/L |
| Arginine | 10 g/L | Tryptophan | 0.1 g/L |
| Lysine | 1 g/L | Histidine | 0.1 g/L |
| Proline | 1 g/L | Adenine | 0.1 g/L |
| Glutamic acid | 1 g/L | Uracil | 0.1 g/L |
| Alanine | 1 g/L | myo-Inositol | 1 g/L |
| Isoleucine | 1 g/L | Pantothenic acid | 4000 μg/L |
| Phenylalanine | 1 g/L | Nicotinic acid (Niacin) | 4000 μg/L |
| Valine | 1 g/L | Pyridoxine | 400 μg/L |
| N-Acetyl tyrosine | 1 g/L | Thiamine | 400 μg/L |
| Methionine | 0.1 g/L | Biotin | 2 μg/L |
| Serine | 0.5 g/L | Ferric (III) chloride | 4000 μg/L |
| Threonine | 0.5 g/L | Zinc sulfate | 400 μg/L |
| Glycine | 0.1 g/L | | |

The present invention further relates to (21) A yeast culture method cultivating yeast in the yeast culture medium according to any one of (1) to (20) under aerobic conditions; and (22) A method of determining nutritional requirements of the yeast by causing yeast to proliferate under aerobic conditions in a culture medium where a specific component is eliminated from the AYD yeast culture medium according to (20).

Effect of the Invention

According to the present invention, investigation is more efficient at a research laboratory phase of yeast useful in industry, including not only prepared baker's yeast but also yeast used in manufacture of fermented food and beverages such as liquor, miso, soy sauce, and pickles; a yeast culture method can be established having a high level of fermentation ability; and production can be stabilized and costs reduced. In addition, a more positive effect can be obtained in microbiology and fermentation industries, such as the discovery of important factors in yeast cultivation.

MODE FOR CARRYING OUT THE INVENTION

Figure 1:
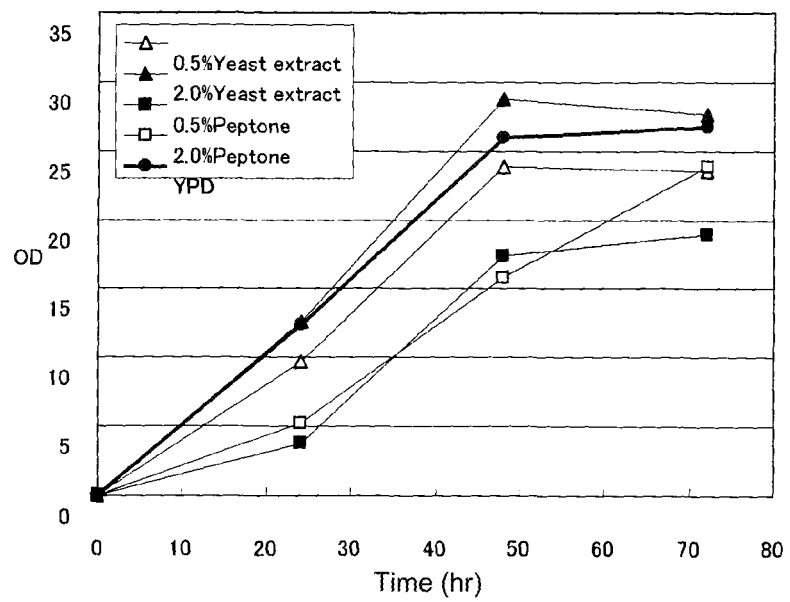
FIG. 1 illustrates proliferation of yeast in a culture medium in which 2% glucose and either polypeptone or yeast extract have been added to 0.17% YNB. A vertical axis indicates $OD_{600}$.

Examples of a yeast culture medium according to the present invention are not particularly limited so long as the culture medium includes a sugar as a carbon source capable of being assimilated by a yeast; an amino acid as a nitrogen source; a vitamin; inositol; zinc ion; and $K^+$ and $Mg^{2+}$, and has an inositol concentration of between 50 and 10,000 mg/L. In the present invention, fungal proliferation refers to a phenomenon where a number of fungi increases, and one example of a value serving as an indicator of fungal proliferation is optical density (OD) of a culture solution. A wavelength measuring OD can be determined as appropriate for a specimen, a measuring device, and a measurement method; however, a favorable example is $OD_{600}$. A method of measuring OD, using a typical method, can dilute a culture solution as necessary after a predetermined amount of time has passed and make a measurement using an absorptiometer, or can be carried out by automatic measuring equipment. A method of determining proliferation using specified automatic measuring equipment is superior in being capable of continuously obtaining an accurate logarithmic growth phase proliferation curve; however, measurement is performed without diluting the culture solution, and therefore in a case where an $OD_{600}$ value exceeds a measurement ability of the measuring equipment, for example, the equipment may be incapable of obtaining an accurate record of the proliferation curve. In addition, as the yeast culture medium according to the present invention, a culture medium is preferred in which the logarithmic growth phase proliferation curve is an extremely close approximation of, or is identical to, a slope of a proliferation curve for a YPD culture medium, or in which the slope of the proliferation curve for the YPD culture medium is exceeded. For example, a culture medium is preferred in which the $OD_{600}$ value after an appropriate amount of time had elapsed after initiating culture, such as 6 hours, 12 hours, 24 hours, 28 hours, 48 hours, 72 hours, or the like, is 65% or more of the YPD culture medium, preferably 70% or more, preferably 75% or more, preferably 80% or more, more preferably 85% or more, more preferably 90% or more, still more preferably 95% or more, and yet more preferably 100% or more. Specifically, in a case where proliferation after 24 hours of a *Saccharomyces cerevisiae* RAK3599 strain of yeast is represented by $OD_{600}$, a preferred example of the culture medium is 80% or more of the YPD culture medium, and preferably is 90% or more, and of these an AYD culture medium shown in Table 1 above is a particularly preferred example.

So long as the yeast is taxonomically classified, the yeast is not particularly limited and examples may include *Debaryomyces*, *Hansenula*, *Candida*, *Kluyveromyces*, *Metschnikowia*, *Nematospora*, *Pichia*, *Saccharomyces*, *Saccharomycodes*, *Schizosaccharomyces*, *Schwanniomyces*, *Trichosporon*, *Torulopsis*, *Rhodotorula*, *Yarrowia*, and the like. More specifically, examples may include *Candida* yeasts such as *C. albicans*, *C. utilis*, *C. glabrata*, *C. boidinii*, *C. tropicalis*, *C. lipolytica*, *C. flaveri*, and *C. versatilis*; *Debaryomyces* yeasts such as *D. hansenii*; *Hansenula* yeasts such as *H. anomala*; *Kluyveromyces* yeasts such as *K. africanus*, *K. lactis*, *K. marxianus*, and *K. phaseolosporous*; *Metschnikowia* yeasts such as *M. pulcherrima*; *Pichia* yeasts such as *P. stipitis*, *P. farinosa*, *P. pastris*, and *P. anomala*; *Rhodotorula* yeasts such as *R. minuta* and *R. mucilaginosa*; *Saccharomyces* yeasts such as *S. kudriavzevii*, *S. cerevisiae*, *S. douglasii*, *S. carlsbergensis*, *S. paradoxus*, *S. pastorianus*, *S. bayanus*, *S. mangini*, and *S. mikatae*; *Schwanniomyces* yeasts such as *S. alluvius*, *S. occidentalis*, and *S. castellii*; *Saccharomycodes* yeasts such as *S. ludwigii*; *Nematospora* yeasts such as *N. coryli*; *Schizosaccharomyces* yeasts such as *S. pombe*; *Trichosporon* yeasts such as *T. pullulans* and *T. penicillatum*; *Yarrowia* (*saccharomycopsis*) *lipolytica*; and the like, as well as mutants of the above yeasts.

Examples of a mutant of the above-noted yeasts can include a yeast mutant exhibiting growth similar to that of the RAK3599 strain when cultivated in the culture medium according to the present invention. In addition, the yeast mutant noted above refers to a yeast or yeast population that has developed a mutation, and is not limited to a yeast having a mutation in only one gene. Instead, the yeast mutant may also include multiple mutation yeast that has developed mutations in a plurality of genes. The mutation may be an induced mutation from UV bombardment, ethyl methanesulfonate (EMS) processing, or the like; a natural mutation; or a mutation may be developed using a gene recombination technique. An example of the yeast mutant can be a nutrient-requiring yeast strain, of which histidine-, leucine-, lysine-, tryptophan-, uracil-, and/or adenine-requiring yeast strains are commonly known examples (see Brachmann et al., Yeast, vol. 14 115-132, 1998, for example).

Examples of the sugar serving as the carbon source used in the culture medium composition are not particularly limited so long as the sugar is capable of being assimilated in the yeast. Specific examples may include simple sugars such as glucose, mannose, fructose, and galactose; disaccharides such as sucrose, maltose, and lactose; trisaccharides such as raffinose; and the like. Of these, glucose is particularly preferred. These sugars can be added singly or in combination of two or more.

An amount of the sugar added to the culture medium of the present invention during use can be determined as appropriate in consideration of cost and/or a range not adversely affecting a positive effect of the yeast culture medium of the present invention. When added to the culture medium, final concentration of the sugar serving as the carbon source is preferably between 1 and 200 g/L, more preferably between 5 and 100 g/L, still more preferably between 10 and 50 g/L, and between 15 and 25 g/L is particularly preferred.

Examples of the amino acid(s) serving as the nitrogen source included in the culture medium of the present invention are not particularly limited so long as the amino acid, its derivative, or a salt thereof does not inhibit proliferation of the yeast. Specific examples can include twenty types of amino acid, i.e., aspartic acid (Asp), arginine (Arg), lysine (Lys), proline (Pro), glutamic acid (Glu), alanine (Ala), methionine (Met), serine (Ser), threonine (Thr), glycine (Gly), asparagine (Asn), isoleucine (Ile), leucine (Leu), phenylalanine (Phe), valine (Val), tryptophan (Trp), tyrosine (Tyr), glutamine (Gln), histidine (His), and cysteine (Cys); a derivative thereof; or a salt thereof. Various L-isomers of the amino acids are preferred.

Examples of the salt of the amino acids can include aspartic acid salts such as L-aspartic acid sodium salt monohydrate, potassium L-aspartic acid, and magnesium L-aspartic acid; arginine salts such as L-arginine hydrochloride; lysine salts such as L-lysine hydrochloride; glutamic acid salts such as monosodium L-glutamate; asparagine salts such as L-asparagine monohydrate; a derivative of tyrosine such as acetyl tyrosine; cysteine salts such as cysteine hydrochloride monohydrate; and histidine salts such as histidine hydrochloride monohydrate.

An amount of each amino acid serving as the nitrogen source added to the culture medium of the present invention during use can be determined as appropriate in consideration of cost and/or a range not adversely affecting a positive effect of the yeast culture medium of the present invention. When added to the culture medium, final concentration of the total amount of amino acid is preferably between 1 and 100 g/L, more preferably between 10 and 50 g/L, still more preferably between 20 and 40 g/L, and between 25 and 35 g/L is particularly preferred. Hereafter, a content amount of individual amino acids is described.

The concentration of aspartic acid in the yeast culture medium of the present invention is, in terms of L-aspartic acid sodium salt monohydrate for example, preferably between 0.1 and 10 g/L, more preferably between 0.5 and 8 g/L, still more preferably between 3 and 7 g/L, and between 4 and 6 g/L is particularly preferred.

The concentration of arginine in the yeast culture medium of the present invention is, in terms of arginine hydrochloride for example, preferably between 1 and 50 g/L, more preferably between 5 and 20 g/L, still more preferably between 8 and 12 g/L, and between 9 and 11 g/L is particularly preferred.

The concentration of lysine in the yeast culture medium of the present invention is, in terms of lysine hydrochloride for example, preferably between 0.1 and 5 g/L, more preferably between 0.5 and 3 g/L, still more preferably between 0.7 and 2 g/L, and between 0.8 and 1.2 g/L is particularly preferred.

The concentration of proline in the yeast culture medium of the present invention is preferably between 0.1 and 5 g/L, more preferably between 0.5 and 3 g/L, still more preferably between 0.7 and 2 g/L, and between 0.8 and 1.2 g/L is particularly preferred.

The concentration of glutamic acid in the yeast culture medium of the present invention is, in terms of monosodium glutamate monohydrate for example, preferably between 0.1 and 5 g/L, more preferably between 0.5 and 3 g/L, still more preferably between 0.7 and 2 g/L, and between 0.8 and 1.2 g/L is particularly preferred.

The concentration of alanine in the yeast culture medium of the present invention is preferably between 0.1 and 5 g/L, more preferably between 0.5 and 3 g/L, still more preferably between 0.7 and 2 g/L, and between 0.8 and 1.2 g/L is particularly preferred.

The concentration of isoleucine in the yeast culture medium of the present invention is preferably between 0.1 and 5 g/L, more preferably between 0.5 and 3 g/L, still more preferably between 0.7 and 2 g/L, and between 0.8 and 1.2 g/L is particularly preferred.

The concentration of phenylalanine in the yeast culture medium of the present invention is preferably between 0.1 and 5 g/L, more preferably between 0.5 and 3 g/L, still more preferably between 0.7 and 2 g/L, and between 0.8 and 1.2 g/L is particularly preferred.

The concentration of valine in the yeast culture medium of the present invention is preferably between 0.1 and 5 g/L, more preferably between 0.5 and 3 g/L, still more preferably between 0.7 and 2 g/L, and between 0.8 and 1.2 g/L is particularly preferred.

The concentration of tyrosine in the yeast culture medium of the present invention is, in terms of N-acetyl tyrosine (hereafter also referred to simply as "acetyl tyrosine") for example, preferably between 0.1 and 5 g/L, more preferably between 0.5 and 3 g/L, still more preferably between 0.7 and 2 g/L, and between 0.8 and 1.2 g/L is particularly preferred.

The concentration of methionine in the yeast culture medium of the present invention is preferably between 0.01 and 1 g/L, more preferably between 0.02 and 0.5 g/L, still more preferably between 0.05 and 0.2 g/L, and between 0.08 and 0.12 g/L is particularly preferred.

The concentration of serine in the yeast culture medium of the present invention is preferably between 0.01 and 5 g/L, more preferably between 0.1 and 2 g/L, still more preferably between 0.2 and 1.2 g/L, and between 0.3 and 0.7 g/L is particularly preferred.

The concentration of threonine in the yeast culture medium of the present invention is preferably between 0.01 and 5 g/L, more preferably between 0.1 and 2 g/L, still more preferably between 0.2 and 1.2 g/L, and between 0.3 and 0.7 g/L is particularly preferred.

The concentration of glycine in the yeast culture medium of the present invention is preferably between 0.01 and 1 g/L, more preferably between 0.02 and 0.5 g/L, still more preferably between 0.05 and 0.2 g/L, and between 0.08 and 0.12 g/L is particularly preferred.

The concentration of asparagine in the yeast culture medium of the present invention is, in terms of asparagine monohydrate for example, preferably between 0.01 and 5 g/L, more preferably between 0.1 and 2 g/L, still more preferably between 0.2 and 1.2 g/L, and between 0.3 and 0.7 g/L is particularly preferred.

The concentration of glutamine in the yeast culture medium of the present invention is preferably between 0.1 and 7.5 g/L, more preferably between 0.5 and 7 g/L, still more preferably between 3 and 6.5 g/L, and between 4 and 6 g/L is particularly preferred.

The concentration of cysteine in the yeast culture medium of the present invention is, in terms of cysteine hydrochloride monohydrate for example, preferably between 0.001 and 0.08 g/L, more preferably between 0.005 and 0.05 g/L, still more preferably between 0.0075 and 0.025 g/L, and between 0.008 and 0.012 g/L is particularly preferred.

The concentration of leucine in the yeast culture medium of the present invention is preferably between 0.1 and 5 g/L, more preferably between 0.5 and 3 g/L, still more preferably between 0.7 and 2 g/L, and between 0.8 and 1.2 g/L is particularly preferred.

The concentration of tryptophan in the yeast culture medium of the present invention is preferably between 0.01 and 1 g/L, more preferably between 0.02 and 0.5 g/L, still more preferably between 0.05 and 0.2 g/L, and between 0.08 and 0.12 g/L is particularly preferred.

The concentration of histidine in the yeast culture medium of the present invention is, in terms of histidine hydrochloride monohydrate for example, preferably between 0.01 and 1 g/L, more preferably between 0.02 and 0.5 g/L, still more preferably between 0.05 and 0.2 g/L, and between 0.08 and 0.12 g/L is particularly preferred.

In a case where one kind of amino acid is added to the yeast culture medium of the present invention as the nitrogen source amino acid, aspartic acid is preferably added.

In a case where there are two kinds of amino acid added to the yeast culture medium of the present invention as the nitrogen source amino acids, examples can include 19 combinations such as aspartic acid with glutamic acid; aspartic acid with arginine; aspartic acid with lysine; aspartic acid with proline; aspartic acid with alanine; aspartic acid with isoleucine; aspartic acid with phenylalanine; aspartic acid with valine; aspartic acid with tyrosine; aspartic acid with methionine; aspartic acid with serine; aspartic acid with threonine; aspartic acid with glycine; aspartic acid with asparagine; aspartic acid with glutamine; aspartic acid with cysteine; aspartic acid with leucine; aspartic acid with tryptophan; and aspartic acid with histidine.

The nitrogen source amino acid preferably includes at least three kinds selected from aspartic acid, arginine, lysine, proline, glutamic acid, alanine, isoleucine, phenylalanine, valine, tyrosine, methionine, serine, threonine, glycine, asparagine, glutamine, cysteine, leucine, tryptophan, and histidine.

Examples of the at least three kinds of amino acid selected as the nitrogen source can include at least 1140 combinations having at least three kinds of amino acids, such as aspartic acid, glutamic acid, and arginine; aspartic acid, glutamic acid, and alanine; aspartic acid, glutamic acid, and leucine; aspartic acid, glutamic acid, and isoleucine; aspartic acid, glutamic acid, and cysteine; aspartic acid, arginine, and alanine; aspartic acid, arginine, and leucine; aspartic acid, arginine, and isoleucine; aspartic acid, arginine, and valine; aspartic acid, arginine, and glutamine; aspartic acid, arginine, and cysteine; aspartic acid, arginine, and asparagine; aspartic acid, arginine, and tyrocine; aspartic acid, lysine, and leucine; aspartic acid, lysine, and isoleucine; aspartic acid, lysine, and valine; aspartic acid, lysine, and glutamine; aspartic acid, lysine, and cysteine; aspartic acid, lysine, and asparagine; aspartic acid, lysine, and tyrosine; aspartic acid, proline, and leucine; aspartic acid, proline, and isoleucine; aspartic acid, proline, and valine; aspartic acid, proline, and glutamine; aspartic acid, proline, and cysteine; aspartic acid, proline, and asparagine; aspartic acid, proline, and tyrosine; glutamic acid, arginine, and alanine; glutamic acid, arginine, and leucine; glutamic acid, arginine, and isoleucine; glutamic acid, arginine, and valine; glutamic acid, arginine, and glutamine; glutamic acid, arginine, cysteine; glutamic acid, arginine, and asparagine; glutamic acid, arginine, and tyrosine; glutamic acid, lysine, and leucine; glutamic acid, lysine, and isoleucine; glutamic acid, lysine, and valine; glutamic acid, lysine, and glutamine; glutamic acid, lysine, and cysteine; glutamic acid, lysine, and asparagine; glutamic acid, lysine, and tyrosine; glutamic acid, proline, and leucine; glutamic acid, proline, and isoleucine; glutamic acid, proline, and valine; glutamic acid, proline, and glutamine; glutamic acid, proline, and cysteine; glutamic acid, proline, and asparagine; and glutamic acid, proline, and tyrosine, for example, for aspartic acid or glutamic acid; arginine, alanine, and methionine; arginine, leucine, and tyrosine; arginine, isoleucine, and threonine; alanine, valine, and serine; arginine, phenylalanine, and glutamine; arginine, proline, and cysteine; and arginine, asparagine, and glutamine.

In addition to the amino acid, nucleic acid(s) such as uracil, adenine, guanine, cytosine, and thymine; a derivative thereof; or a salt thereof may be further added singly or in combination of two or more as the nitrogen source included in the yeast culture medium of the present invention, so far as does not inhibit proliferation of the yeast. Examples of the derivative can include, as an adenine derivative, adenine hemisulfate. The concentration of each nucleic acid in the yeast culture medium of the present invention is preferably between 0.01 and 1 g/L, more preferably between 0.02 and 0.5 g/L, still more preferably between 0.05 and 0.2 g/L, and between 0.08 and 0.12 g/L is particularly preferred.

Furthermore, as the nitrogen source included in the yeast culture medium of the present invention, a nitrogen source is preferred which can inhibit excessive reduction of pH of the culture medium accompanying culture of the yeast and can maintain proliferation of the yeast. Therefore, ammonium ions such as ammonium sulfate, ammonium chloride, and ammonium acetate are preferably not included as the nitrogen source capable of being assimilated by the yeast.

Vitamins included in the yeast culture medium of the present invention are not particularly limited so long as they are vitamins, derivatives thereof, or salts thereof not inhibiting proliferation of the yeast, examples of which can include biotin, pantothenic acid, niacin, pyridoxine, and thiamine. Examples of pantothenic acid, a derivative thereof, or a salt thereof can include calcium pantothenate, sodium pantothenate, and panthenol. Examples of niacin, a derivative thereof, or a salt thereof can include nicotinic acid, nicotinamide, and nicotinyl alcohol. Examples of a thiamine derivative can include thiamine hydrochloride, thiamine nitrate, bisthiamine nitrate, thiamine dicetyl sulfuric acid ester salt, fursultiamine hydrochloride, octotiamine, and benfotiamine. Examples of pyridoxine, a derivative thereof, or a salt thereof can include pyridoxine hydrochloride, pyridoxal (pyridoxal phosphate), and pyridoxamine. Preferably, two or more kinds of the above-noted vitamins are included, more preferably three or more kinds, and still more preferably four or more kinds.

In a case where the yeast belongs to the *Saccharomyces* genus, examples of the vitamins can include combinations containing biotin and pantothenic acid; biotin, pantothenic acid, and niacin; biotin, pantothenic acid, and pyridoxine; biotin, pantothenic acid, and thiamine; biotin, pantothenic acid, niacin, and pyridoxine; biotin, pantothenic acid, niacin, and thiamine; biotin, pantothenic acid, pyridoxine, and thiamine; and biotin, pantothenic acid, niacin, pyridoxine, and thiamine. In a case where the yeast belongs to the *Kluyveromyces* genus, examples can include combinations containing biotin, pantothenic acid, and niacin; biotin, pantothenic acid, niacin, and pyridoxine; biotin, pantothenic acid, niacin, and thiamine; and biotin, pantothenic acid, niacin, pyridoxine, and thiamine. In a case where the yeast belongs to the *Candida* genus, examples of the vitamins can include combinations containing at least one selected from pyridoxine, biotin, pantothenic acid, thiamine, and niacin.

An amount of each vitamin added to the culture medium of the present invention during use can be determined as appropriate in consideration of cost and/or a range not adversely affecting a positive effect of the yeast culture medium of the present invention, and specifically includes the following examples.

The concentration of pantothenic acid in the culture medium of the present invention is preferably between 10 and 50,000 µg/L, more preferably between 100 and 25,000 µg/L, still more preferably between 1000 and 7500 µg/L, and between 3000 and 5000 µg/L is particularly preferred.

The concentration of niacin (nicotinic acid) in the culture medium of the present invention is preferably between 10 and 50,000 µg/L, more preferably between 100 and 25,000 µg/L, still more preferably between 1000 and 7500 µg/L, and between 3000 and 5000 µg/L is particularly preferred.

The concentration of pyridoxine in the culture medium of the present invention is preferably between 1 and 5000 µg/L, more preferably between 10 and 2500 µg/L, still more preferably between 100 and 750 µg/L, and between 300 and 500 µg/L is particularly preferred.

The concentration of thiamine in the culture medium of the present invention is preferably between 1 and 5000 µg/L, more preferably between 10 and 2500 µg/L, still more preferably between 100 and 750 µg/L, and between 300 and 500 µg/L is particularly preferred.

Examples of an amount of biotin added to the culture medium of the present invention during use can be between 0.02 and 150 µg/L, preferably between 0.2 and 20 µg/L, more preferably between 0.5 and 10 µg/L, still more preferably between 1 and 5 µg/L, and between 1.5 and 3 µg/L is particularly preferred.

The inositol in the culture medium of the present invention is myo-inositol, and because a logarithmic growth phase proliferation curve equivalent to YPD can be obtained by adding an effective amount, the inositol must be added as a proliferation limiting factor in the present invention. The concentration of myo-inositol in the culture medium of the present invention is between 50 and 10,000 mg/L, preferably between 100 and 7500 mg/L, more preferably between 500 and 5000 mg/L, still more preferably between 750 and 3000 mg/L, and between 1000 and 2500 mg/L is particularly preferred.

An example of a metallic ion added to the culture medium of the present invention is a zinc ion ($Zn^{2+}$), and other metallic ions can also be added so long as the metallic ion does not inhibit proliferation of the yeast. An example of such other metallic ions can include, specifically, iron ions ($Fe^{3+}$ and/or $Fe^{2+}$).

As a specific example of the $Zn^{2+}$, zinc sulfate ($ZnSO_4$) or the like can be added, and the concentration of $Zn^{2+}$ in the culture medium of the present invention is, in terms of $ZnSO_4$, preferably between 1 and 5000 µg/L, more preferably between 50 and 1000 µg/L, still more preferably between 100 and 750 µg/L, and between 300 and 500 µg/L is particularly preferred.

As a specific example of the $Fe^{3+}$, a ferric chloride ($FeCl_3$) anhydride or hydrate can be added, and examples of an amount of $Fe^{3+}$ added to the culture medium of the present invention during use can, in terms of $FeCl_3$ (anhydride), be between 1 and 500,000 µg/L, preferably between 200 and 40,000 µg/L, more preferably between 500 and 10,000 µg/L, still more preferably between 1000 and 7500 µg/L, and between 3000 and 5000 µg/L is particularly preferred. Examples of the $Fe^{2+}$ can include $FeSO_4$ anhydride or hydrate, $FeCl_2$ anhydride or hydrate, or the like.

An inorganic ion included in the culture medium of the present invention is not particularly limited so long as the inorganic ion does not inhibit proliferation of the yeast; however, a potassium ion ($K^+$) and a magnesium ion ($Mg^{2+}$) are required.

Specifically, the $K^+$ can be added as dipotassium phosphate ($K_2HPO_4$), potassium dihydrogen phosphate ($KH_2PO_4$), or potassium chloride (KCl), which can be used singly or a plurality of which can be mixed for use. The concentration of $K^+$ in the culture medium of the present invention is, in terms of $KH_2PO_4$ for example, preferably between 0.1 and 10 g/L, more preferably between 0.1 and 5 g/L, still more preferably between 0.5 and 2.5 g/L, and between 0.8 and 1.2 g/L is particularly preferred.

Specifically, the $Mg^{2+}$ can be added as magnesium sulfate-heptahydrate, magnesium chloride-hexahydrate, magnesium citrate, magnesium hydrogen phosphate, or potassium magnesium chloride, which can be used singly or a plurality of which can be mixed for use. The concentration of $Mg^{2+}$ in the culture medium of the present invention is, in terms of magnesium sulfate-heptahydrate for example, preferably between 0.01 and 5 g/L, more preferably between 0.1 and 2 g/L, still more preferably between 0.2 and 1.2 g/L, and between 0.3 and 0.7 g/L is particularly preferred.

In addition, in a case where increasing the proliferation of the yeast in the culture medium of the present invention is a particular focus, corn steep liquor, yeast extract, polypeptone, meat extract, and the like can be added as necessary. However, a culture medium that does not include the yeast extract, corn steep liquor, polypeptone, meat extract, and the like due to being a chemical synthetic culture medium can advantageously achieve the effects of the present invention.

Depending on a fungal count, ease of handling, and the like, an embodiment of the culture medium of the present invention may be a liquid culture medium, or may be a solid culture medium to which a polysaccharide such as agar-agar has been added. In the case of a liquid culture medium, in order to elevate yeast proliferation, the yeast is preferably cultured in aerobic conditions supplied with oxygen, and specific examples of a method for culturing in aerobic conditions can include shaking culture, aerated and agitated culture, or aerobic roller tube culture performed in commonly known ways.

Depending on cultivation temperature of each strain, a high level of proliferation can be exhibited, and examples of a preferred cultivation temperature can include, for *Saccharomyces* genus, between 25 and 35° C.; for *Candida* yeast, between 25 and 35° C.; for *Kluyveromyces* yeast, between 25 and 45° C.; for *Pichia* yeast, between 25 and 35° C.; and for *Schizosaccharomyces* yeast, between 25 and 35° C.

An amount of yeast added to the culture medium of the present invention is preferably between 1 and 10% (VAT) from a perspective of ease of use in a culture, proliferation speed, time to reach final concentration, and the like. However, the amount of yeast added is not limited to this range, and can be cultivated at a higher or lower concentration according to ingredients used and objectives.

The present invention is described in further detail below with reference to embodiments. However, the technical scope of the present invention is not limited to these embodiments. Moreover, the order in which the embodiments are listed approximately follows a timeline of an experiment. In addition, investigation data for concentration settings and necessary components is not limited to that noted below. Although there is an enormous amount of data due to a trial-and-error procedure, only data necessary to describe characteristic features of the present invention has been provided. The vertical axis of graphs in FIGS. 8 to 20 and 22 to 52 indicates $OD_{600}$.

Embodiment 1

(1) Investigation 1

[Materials and Method]

(Trial Yeast Strain)

A BY sequence yeast (see, for example, Brachmann et al. 1998. Yeast 14: 115-132) and a RAK sequence yeast were used as yeast strains. Specifically, yeasts were used such as *Saccharomyces cerevisiae* RAK3599 strain; *Saccharomyces cerevisiae* RAK2683 strain; *Saccharomyces cerevisiae* BY4741 strain (leu2Δ0 ura3Δ0 his3Δ1 met15Δ0); *Saccharomyces cerevisiae* BY4700 strain (ura3Δ0); *Saccharomyces cerevisiae* BY4712 strain (leu2Δ0); *Saccharomyces cerevisiae* BY4714 strain (his3Δ1); *Saccharomyces cerevisiae* BY4725+URA3 strain (ade2Δ::hisG); *Saccharomyces cerevisiae* BY4710 strain (TrpΔ63); *Schizosaccharomyces pombe* FY7507 strain; *Zygosaccharomyces* RAK5576 strain; *Kluyveromyces marxianus* NCYC587 (RAK3684) strain, NCYC1429 (RAK3685) strain, and NCYC2791 (RAK3686) strain; *Kluyveromyces lactis* NRRLY-1140 strain; *Pichia stipitis* NBRC 10063 (RAK5128) strain; *Candida glabrata* BY23876 strain; and the like. The noted yeast strains of the embodiment are held at Yamaguchi University Faculty of Engineering, and can be purchased in lots having fixed conditions.

(Basic Culture Method)

In a case where no special provisions are made, a procedure for a cultivation experiment using the culture medium to be investigated for proliferation was such that a yeast undergoing investigation was pre-cultured in a YPD liquid culture medium at 28° C. for 24 hours, after which the yeast was adjusted such that $OD_{600}=20$. Thereafter, 5 μL of culture solution was inoculated in 5 mL of each culture medium to be investigated, which had been dispensed into L-shaped test tubes (final $OD_{60}=0.02$); aerobic roller tube culture was performed at 28° C.; and OD was continuously measured with an automatic spectrophotometer (BioPhoto recorder TVS062CA, ADVANTEC). In addition, $OD_{600}$ was measured every 15 minutes by a spectrophotometer (Cell density meter co8000, WPA). Hereafter, data is represented by graphs for a case using the automatic spectrophotometer; however, these graphs are primarily used to compare the slope of logarithmic growth phase proliferation curves for each culture medium, and because $OD_{600}$ is measured without dilution, values where $OD_{600}=3$ to 3.5 or more may be incorrect.

[Preliminary Experiment]

In order to establish a composition of the synthetic culture medium for increasing proliferation of yeast, first proliferation of yeast was investigated in a YPD culture medium (a eutrophic culture medium having a target proliferation) and in an MM culture medium selected as a minimally synthetic culture medium. A culture medium used as the MM culture medium had a composition in which 0.5% ammonium sulfate as a nitrogen source and 2% glucose as a carbon source were added to 0.17% YNB (free of amino acid, ammonium sulfate, and glucose) (Y2030, "Yeast Nitrogen Base w/o AA, carbohydrate & w/o AS", manufactured by US Biological Co.), shown in Table 2 below. In addition, the composition of a YPD culture medium used was 1% yeast extract, 2% peptone, 2% glucose, and a pH between 5.6 and 6.0. In various 1 mL liquid culture solutions ($OD_{600}=35$), 10 mL commercially available baker's yeast was inoculated, and after one day $OD_{600}$ and pH were measured for 1/20 solutions.

TABLE 2

| Salt (mg/L) | | Vitamin (mg/L) | | Trace element (mg/L) | |
|---|---|---|---|---|---|
| $KH_2PO_4$ | 1,000 | Biotin | 0.002 | Boric acid | 0.5 |
| $MgSO_4$ | 500 | Ca pantothenate | 0.4 | $CuSO_4$ | 0.04 |
| NaCl | 100 | Folic acid | 0.002 | KI | 0.1 |
| $CaCl_2$ | 100 | Inositol | 2.0 | $FeCl_3$ | 0.2 |
| | | Niacin | 0.4 | $MnSO_4$ | 0.4 |
| | | PABA | 0.2 | $Na_2MoO_4$ | 0.2 |
| | | Pyridoxine, HCl | 0.4 | $ZnSO_4$ | 0.4 |
| | | Riboflavin | 0.2 | | |
| | | Thiamine, HCl | 0.4 | | |

(Relationship Between Proliferation and Culture Solution pH)

In the YPD culture medium, an $OD_{600}$ value was 0.82 and pH was 6.0, whereas in the MM culture medium, the $OD_{600}$ value was 0.35 and pH was 2.4. The pH of the MM culture medium after cultivation was extremely low in comparison to the YPD culture medium, and so the change in pH of the culture medium was investigated.

(Investigation of Culture Medium pH)

In the composition per 1 mL of liquid culture mediums shown in Table 3 below, the pH of the culture mediums prior to cultivation was adjusted to 6.0, and cultivation of commercially available baker's yeast was performed for 24 hours. As a result, for (1) MM+buffer, pH was not very much reduced; however, proliferation did not reach that of (6) MM pH6 (no buffer). For (2) MM+2% PP culture medium and (3) MM+1% YE culture medium, pH was not very much reduced and proliferation was favorable as compared to (1) MM+buffer, but did not reach that of (5) YPD culture medium. Accordingly, a direct relationship between proliferation and a reduction in pH could not be discerned.

TABLE 3

| Culture medium designation | Culture medium composition (per 1 mL) | | After 24 hr | |
|---|---|---|---|---|
| | 0.5 mL | 0.5 mL | $OD_{600}$ pH | (1/20) |
| (1) MM + buffer | 2 × MM | Citric acid phosphate buffer - (pH 6.0) | 6.5 | 4.8 |
| (2) MM + 2% PP | 2 × MM | 4% polypeptone | 14.0 | 4.8 |
| (3) MM + 1% YE | 2 × MM | 2% yeast extract | 16.5 | 5.0 |
| (4) MM | MM | — | 6.0 | 2.5 |
| (5) YPD | YPD | — | 21.0 | 5.8 |
| (6) MM (pH 6 by NaOH) (no buffer) | 2 × MM | $H_2O$ | 8.0 | 2.5 |

(2) Investigation 2

[Investigation of Proliferation Factors Contained in Yeast Extract]

In Table 3, proliferation was comparatively high in a case where the (2) MM+2% PP culture medium and (3) MM+1% YE culture medium were used, and therefore comparison to proliferation in the YPD culture medium was performed using a culture medium having a composition in which polypeptone or yeast extract and 2% glucose was added to 0.17% YNB (w/o AA, carbohydrate & w/o AS). Results are shown in FIG. 1. By adding 2% yeast extract, proliferation equal to or greater than a level of the YPD culture medium was reached; however, with polypeptone, proliferation did not increase to the level of the YPD culture medium. Accordingly, a decision was made to investigate proliferation factors predicted as being contained in the yeast extract.

(3) Investigation 3
[Investigation of Nitrogen Source]

In a culture medium where various amino acids shown in Table 4 below were used singly as the nitrogen source in the MM culture medium instead of ammonium sulfate or, alternatively, where ammonium phosphate, ammonium chloride (Sigma U4426), ammonium formate (Sigma 04507AC), or ammonium acetate (Sigma U9469) were each used as an ammonium salt other than ammonium sulfate, RAK2683 yeast strain was cultivated for 24 hours, after which the $OD_{600}$, pH, and the like were investigated. Results are shown in Table 4.

lysine are added singly. In addition, not only ammonium sulfate, but ammonium salts such as ammonium chloride and ammonium acetate serving as the nitrogen source did not, as a whole, exhibit favorable proliferation.

Figure 2:
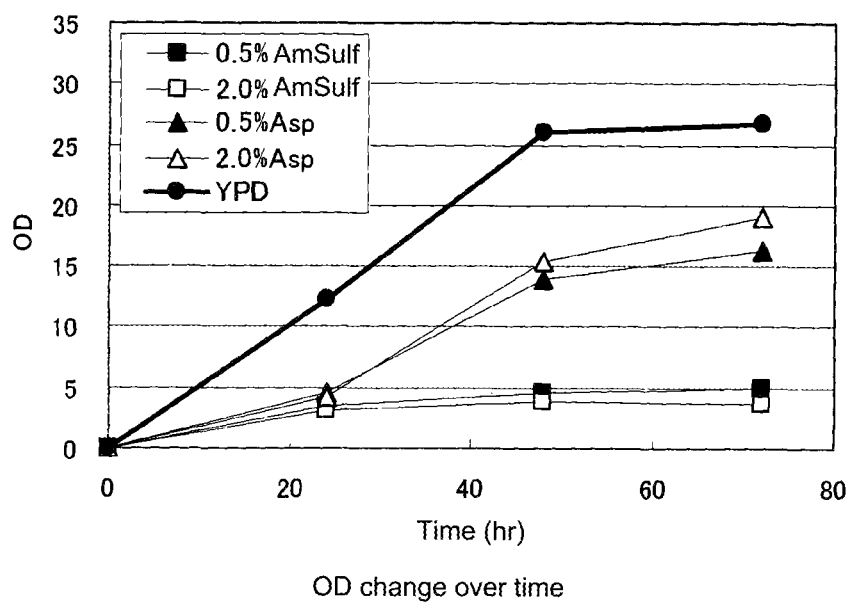
FIG. 2 illustrates $OD_{600}$ when yeast is cultivated in a culture medium in which 2% glucose and either aspartic acid or ammonium sulfate have been added to 0.17% YNB. The vertical axis indicates $OD_{600}$.

In Table 4, a culture medium was prepared in which aspartic acid (Asp), which had the highest value for $OD_{600}$ after 48 hours, was swapped with ammonium sulfate, and the proliferation of yeast (commercially available baker's yeast) in the MM culture medium and YPD was compared. Results are shown in FIG. 2. Despite not reaching the proliferation level of YPD, a culture medium to which between 0.5 and 2.0% aspartic acid had been added was seen to have proliferation markedly improved over that of a culture medium to which ammonium sulfate had been added. Based on this information, a BM culture medium in which 2% aspartic acid had been added as a nitrogen source to 0.17% YNB and 2% glucose was used as an object of investigation.

In order to identify the proliferation factor contained in the yeast extract, attention was first turned to molecular weight, and 10% yeast extract was fractionated into substances having a molecular weight less than 5000 (M<5000)

TABLE 4

| | Amino acid/nitrogen source | Symbol | Abbrev. | Reagent | Concentration | pH | Final con. | pH after inoc. | 48 h pH | 48 h OD |
|---|---|---|---|---|---|---|---|---|---|---|
| 1 | Alanine | Ala | A | L-Alanine | 10% w/v | 6.33 | 2% w/v | 5.1 | 4.2 | 4 |
| 2 | Arginine | Arg | R | L-Arginine hydrochloride | 20% w/v | 5.74 | 2% w/v | 4.7 | 3.1 | 9 |
| 3 | Asparagine | Asn | N | L-Asparagine monohydrate | 1% w/v | 4.5 | 2% w/v | 4.4 | 5.2 | 11 |
| 4 | Aspartic acid | Asp | D | L-Aspartic acid sodium salt monohydrate | 20% w/v | 6.73 | 2% w/v | 5.7 | 5.1 | 19 |
| 5 | Cysteine | Cys | C | L-Cysteine | 10% w/v | 5.08 | 2% w/v | 4.6 | 4.1 | — |
| 6 | Glutamic acid | Glu | E | L-Glutamic acid sodium salt hydrate | 20% w/v | 6.91 | 2% w/v | 5.8 | 5.4 | 15 |
| 7 | Glutamine | Gln | Q | L-Glutamine | 4% w/v | 5.55 | 2% w/v | 4.8 | 4.5 | 8 |
| 8 | Glycine | Gly | G | Glycine (amino acid) | 10% w/v | 6.20 | 2% w/v | 5.1 | 4.9 | 0 |
| 9 | Histidine | His | H | L-Histidine hydrochloride hydrate | 5% w/v | 3.92 | 2% w/v | 3.8 | 3.8 | 0 |
| 10 | Isoleucine | Ile | I | L-Isoleucine | 2% w/v | 6.17 | 1% w/v | 4.9 | 3.9 | 2 |
| 11 | Leucine | Leu | L | L-Leucine | 1% w/v | 5.93 | 0.5% w/v | 4.7 | 3.7 | 4 |
| 12 | Lysine | Lys | K | L-Lysine hydrochloride | 20% w/v | 5.55 | 2% w/v | 4.6 | 4.6 | 0 |
| 13 | Methionine | Met | M | L-Methionine | 4% w/v | 5.96 | 2% w/v | 4.8 | 3.8 | 3 |
| 14 | Phenylalanine | Phe | F | L-Phenylalanine | 1% w/v | 5.10 | 0.5% w/v | 4.6 | 3.5 | 3 |
| 15 | Proline | Pro | P | L-Proline | 20% w/v | 6.61 | 2% w/v | 4.7 | 3.7 | 15 |
| 16 | Serine | Ser | S | L-Serine | 20% w/v | 6.04 | 2% w/v | 4.8 | 6.3 | 10 |
| 17 | Threonine | Thr | T | L-Threonine | 5% w/v | 5.31 | 2% w/v | 4.8 | 3.8 | 0 |
| 18 | Tryptophan | Trp | W | L-Tryptophan | 0.5% w/v | 7.48 | 0.25% w/v | 4.5 | 3.5 | 2 |
| 19 | Valine | Val | V | L-VALINE | 4% w/v | 5.95 | 2% w/v | 4.9 | 4.0 | 2 |
| 20 | Ammonium phosphate | | | | 10% w/v | 6.00 | 2% w/v | 6.1 | 5.7 | 6 |
| 21 | Ammonium chloride | | | | 20% w/v | 4.94 | 2% w/v | 4.1 | 2.5 | 3 |
| 22 | Ammonium formate | | | Ammonium formate | 20% w/v | 6.87 | 2% w/v | 5.5 | 4.7 | 6 |
| 23 | Ammonium acetate | | | | 20% w/v | 7.44 | 2% w/v | 6.2 | 5.8 | 2 |
| 24 | Ammonium sulfate | | | | 20% w/v | 5.41 | 2% w/v | 4.5 | 2.6 | 1 |

Figure 3:
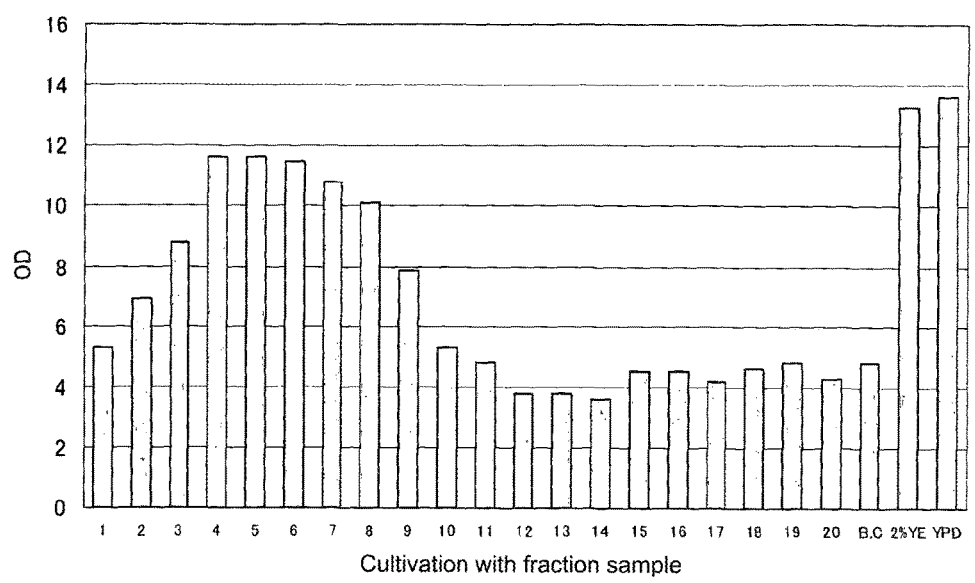
FIG. 3 illustrates $OD_{600}$ 24 hours after a yeast extract fraction sample is added to a culture medium and cultivated. The vertical axis indicates $OD_{600}$.
Figure 4C:
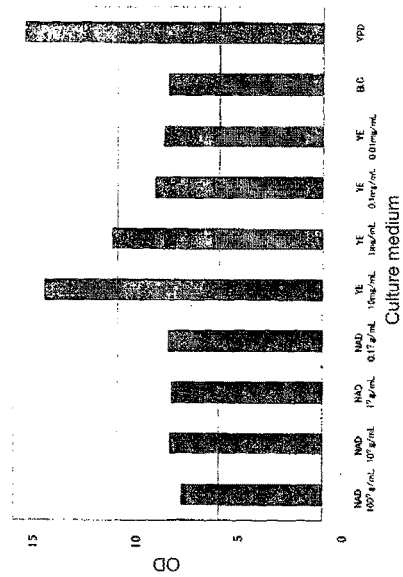
FIG. 4 illustrates $OD_{600}$ 24 hours after yeast has been cultivated in a culture medium in which components noted below have been added to a BM culture medium. YPD and YE (yeast extract) are used as controls. The vertical axis indicates $OD_{600}$. (a) indicates results of adding acetyl-CoA and CoA; (b) indicates results of adding yeast RNA (RNA); and (c) indicates results of adding NAD.
Figure 4A:
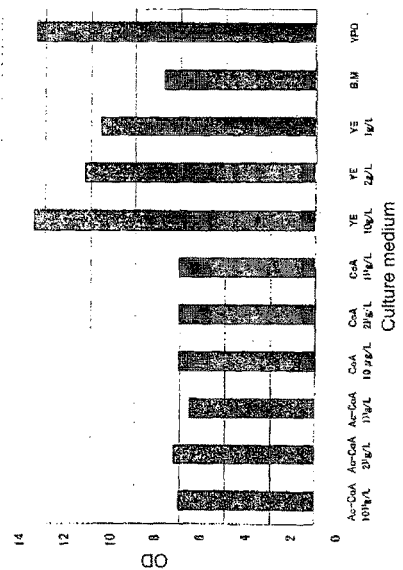
Figure 4B:
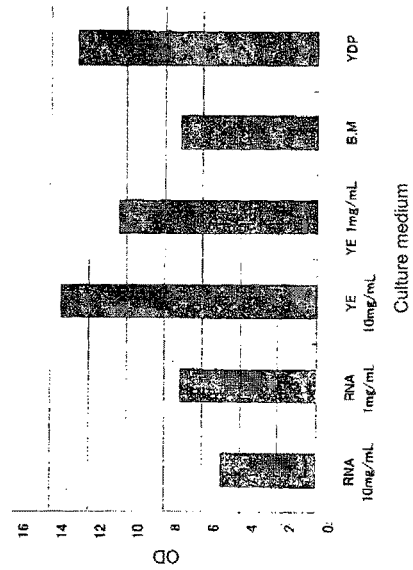

When ammonium sulfate from Table 4 above is added, pH was confirmed to be reduced and proliferation was confirmed to be extremely poor as compared to other nitrogen sources. Furthermore, favorable proliferation is exhibited when aspartic acid, glutamic acid, proline, and the like are added singly as the amino acid, whereas almost no proliferation is exhibited when glycine, histidine, threonine, and and substances having a molecular weight greater than 5000 (M>5000), and RAK2683 strain was cultivated in a culture medium including both fractionated substances at various concentrations, whereupon a reduction in proliferation due to a reduction in concentration of the yeast extract (M<5000) was no different from an ordinary reduction in proliferation of yeast extract. Therefore, the important proliferation factor that was sought was inferred to be included in M<5000. Next, the yeast extract (M<5000) was further fractionated and proliferation was tested. Results are shown in FIG. 3. The substances contained in fraction numbers 4 to 6 in FIG. 3 (roughly 500<M<1000) were presumed to increase proliferation. As the substances having a molecular weight of roughly 500<M<1000, Acetyl-CoA, CoA, yeast RNA (RNA), and NAD were selected; each was added to a BM culture medium; and RAK2683 yeast strain was cultivated for 24 hours, after which $OD_{600}$ was measured. Moreover, the yeast extract (YE)-added culture medium and YPD culture medium were treated as positive controls. Results are shown in FIGS. 4A to 4C. Each of Acetyl-CoA, CoA, yeast RNA, and NAD have similar proliferation in the BM culture medium, none of them reaching the proliferation level of YPD, and it cannot be claimed that any play a significant role as a proliferation factor. At this stage, investigation of the proliferation factor contained in yeast extract was halted.

(4) Investigation 4

[Investigation of Carbon Source]

Figure 5:
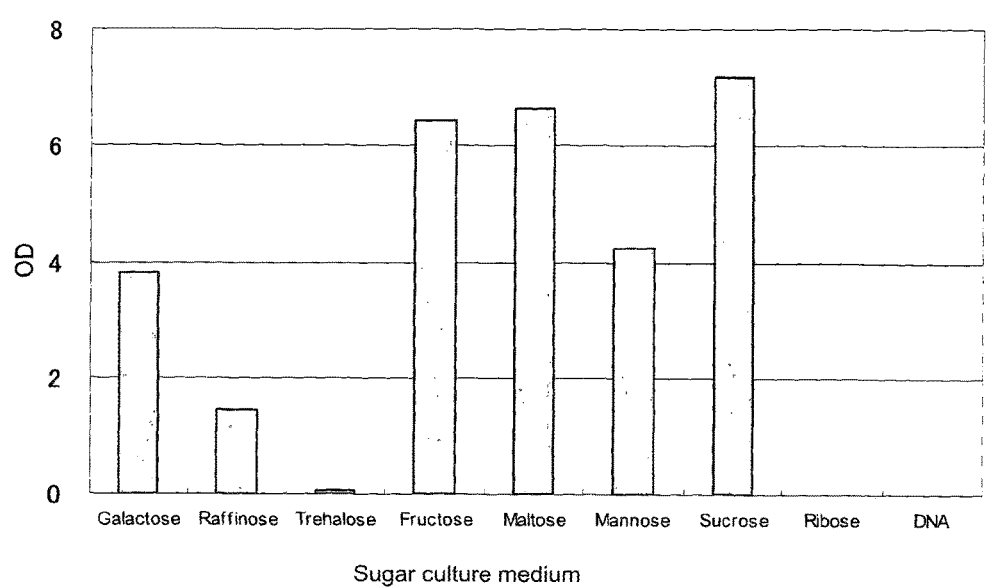
FIG. 5 illustrates $OD_{600}$ 24 hours after yeast has been cultivated in a culture medium in which galactose, raffinose, trehalose, fructose, maltose, mannose, sucrose, ribose, or DNA has been added instead of glucose in a BM culture medium. The vertical axis indicates $OD_{600}$.

$OD_{600}$ was measured after commercially available baker's yeast had been cultivated at 28° C. for 24 hours in a culture medium in which 2% of sugars such as galactose, raffinose, trehalose, fructose, maltose, mannose, sucrose, and ribose, or DNA (negative control) had been added instead of glucose in the BM culture medium. Results are shown in FIG. 5. In a case where trehalose, ribose, or DNA are added singly instead of glucose, the yeast exhibits no proliferation whatsoever, and using trehalose or ribose as the carbon source was understood to be difficult.

Figure 6A:
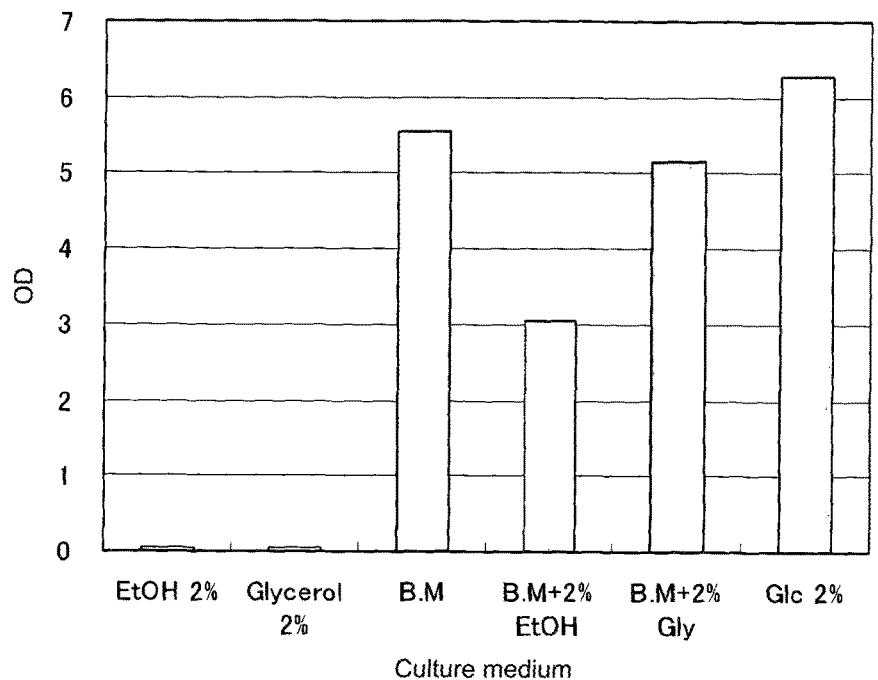
FIG. 6 illustrates $OD_{600}$ 24 hours after ethanol, glycerol, or albumin has been added to the BM culture medium either containing or not containing glucose, and yeast has been cultivated. (a) indicates results of ethanol and glycerol, and (b) indicates results of albumin. The vertical axis indicates $OD_{600}$.
Figure 6B:
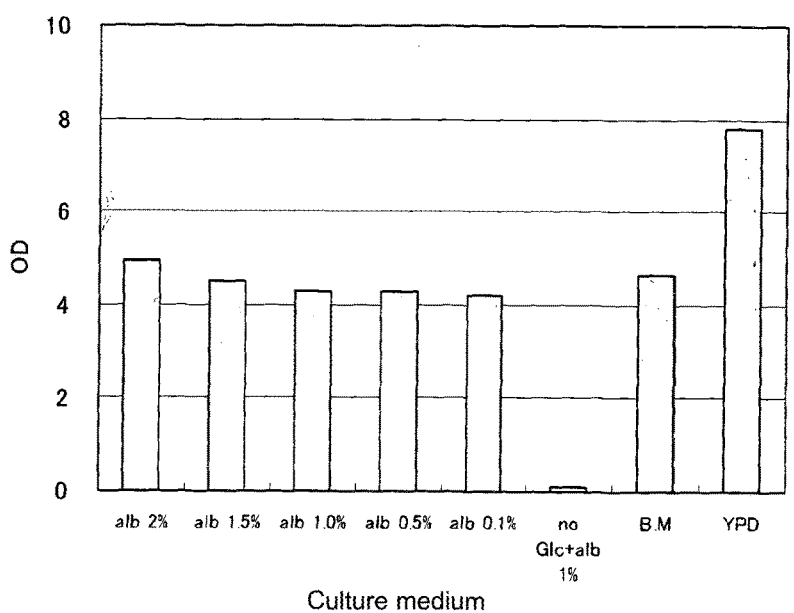
Figure 7A:
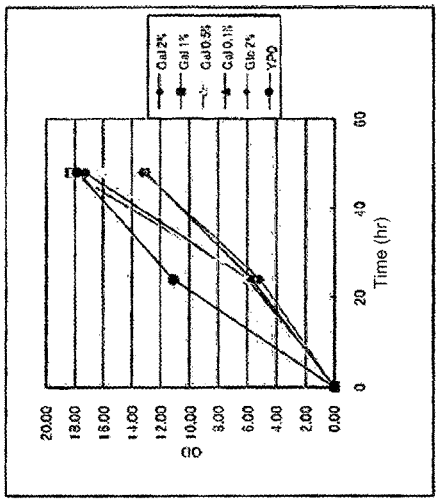
FIG. 7 illustrates $OD_{600}$ when yeast has been cultivated in a culture medium in which a plurality of sugars have been mixed together and added to a BM culture medium containing 2% glucose. (a) indicates results in a case where galactose is added. (b) indicates results in a case where raffinose or mannose is further mixed together with 1% fructose and added. (c) indicates results in a case where sucrose is further added to 1% fructose. (d) indicates results in a case where maltose is added. In all cases, 2% glucose and YPD are used as the control. The vertical axis indicates $OD_{600}$.
Figure 7B:
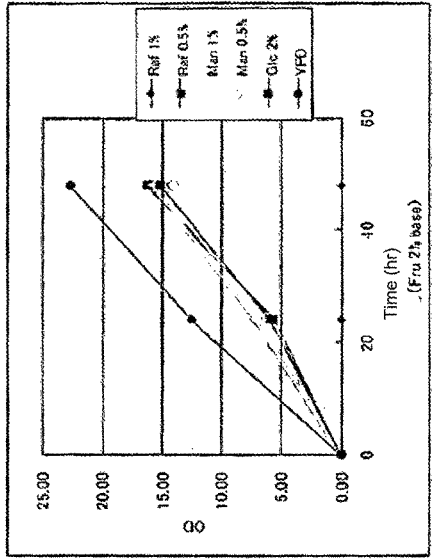
Figure 7C:
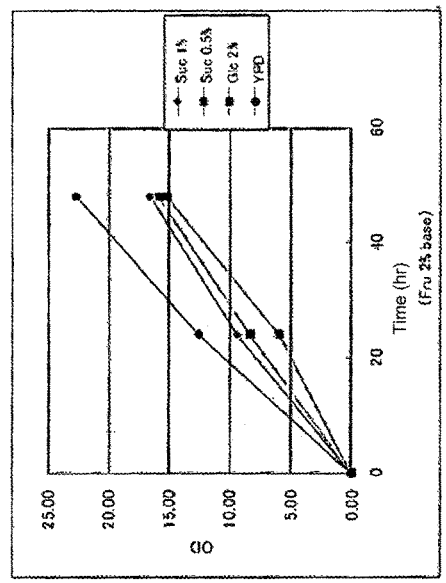
Figure 7D:
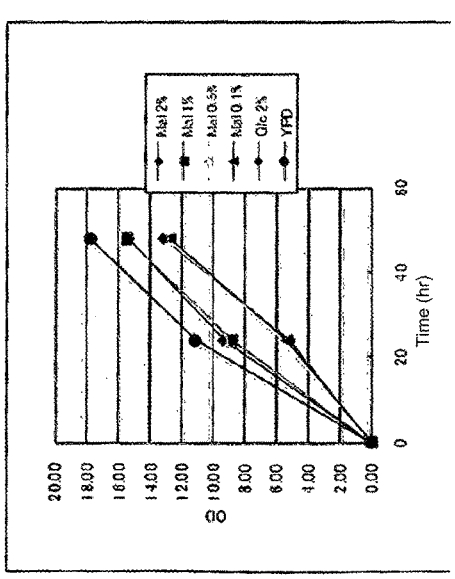

$OD_{600}$ was measured 24 hours after RAK2683 yeast strain had been cultivated in 2% ethanol; in 2% glycerol; in a BM culture medium containing glucose; in a culture medium in which 2% ethanol had been added to a BM culture medium not containing glucose; in a culture medium in which 2% glycerol had been added to a BM culture medium not containing glucose; in a culture medium in which 2% glucose had been added to a BM culture medium not containing glucose. Results are shown in FIG. 6B. $OD_{600}$ was measured after RAK2683 yeast strain had been cultivated for 24 hours in a culture medium in which between 0.1 and 2% albumin had been added to the BM culture medium. Results are shown in FIG. 6B. In a case where glucose was not added to the culture medium, but ethanol, glycerol, or albumin was added, the yeast exhibited almost no proliferation, and using ethanol, glycerol, or albumin as the carbon source was understood to be difficult.

Various culture mediums were prepared in which each of the sugars galactose, raffinose, fructose, maltose, mannose, sucrose, and the like were added to the BM culture medium at a concentration of between 0.5 and 2%, and proliferation was tested. Results are shown in FIG. 7A to 7D. All of the sugars were confirmed to be assimilatable; however, in comparison to a case using only 2% glucose, a particularly high proliferation was not exhibited, and even when a plurality of sugars were mixed together, none exhibited proliferation at the level of the YPD culture medium. Following this, a determination was made to continue investigation with 2% glucose established as the carbon source.

(5) Investigation 5

[Investigation of Various Component Mixes]

Figure 8:
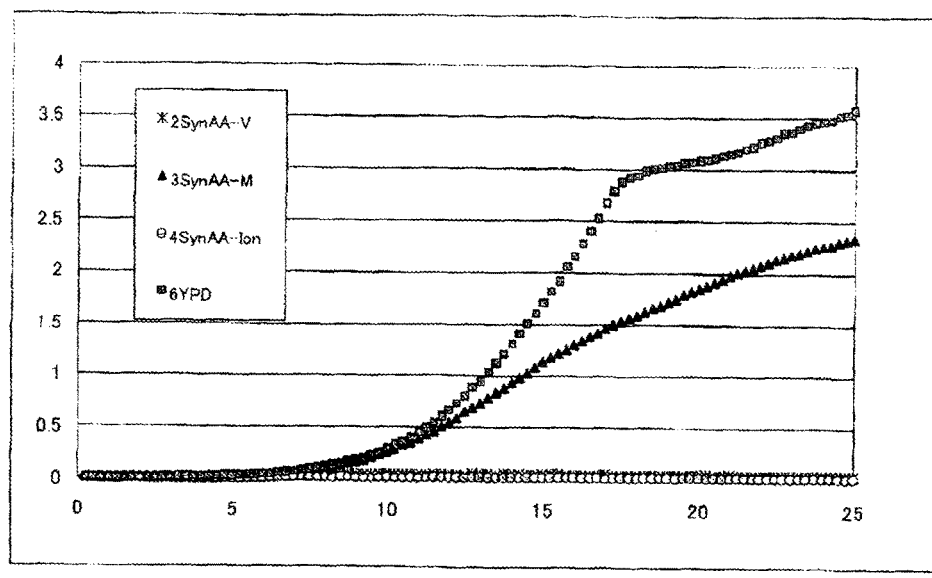
FIG. 8 illustrates results where cultivation was performed in culture mediums in which one each of three component mixes (a vitamin mix (V), a metallic ion mix (M), and an inorganic ion mix (Ion)) are deficient in a SynAA culture medium.

Various component mixes were prepared having as constituent components each of the four component mixes noted in Tables 5 to 8 below, specifically an amino acid mix (AA), a vitamin mix (V), a metallic ion mix (M), and an inorganic ion mix (Ion). Cultivation was performed in a culture medium in which one each of three component mixes (the vitamin mix (V), the metallic ion mix (M), and the inorganic ion mix (Ion)) were deficient in a culture medium in which the four component mixes have been mixed with 20 g/L glucose and 0.5 g/L ammonium sulfate (hereafter also referred to as a "SynAA culture medium"), results of which are shown in FIG. 8. In the culture mediums deficient in the vitamin mix or the inorganic ion mix (SynAA-V or SynAA-Ion), no proliferation whatsoever was observed. Furthermore, in the culture medium deficient in the metallic ion mix (SynAA-M), proliferation was notably poor in comparison to YPD. An inference was made that a component essential or important to yeast proliferation was contained in the constituent components of each of the vitamin mix, inorganic ion mix, and metallic ion mix.

TABLE 5

| Amino acid mix (AA) | Product name | Concentration (g/L) |
|---|---|---|
| Asparatic acid (Asp) (sodium salt monohydrate) | Sigma A6683 | 5 |
| Arginine (Arg) (monohydrochloride) | Sigma A5131 | 10 |
| Lysine (Lys) (monohydrochloride) | Katayama Chemicals 18-1900 | 1 |
| Proline (Pro) | Sigma P0380 | 1 |
| Glutamic acid (Glu) (monosodium salt hydrate) | Sigma G1626 | 1 |
| Alanine (Ala) | Wako 014-01045 | 0.1 |
| Methionine (Met) | Sigma M9625 | 0.1 |
| Serine (Ser) | Sigma S4500 | 0.1 |
| Threonine (Thr) | Sigma T8625 | 0.1 |
| Glycine (Gly) | Katayama 12-1210 | 0.1 |
| Asparagine (Asn) (monohydrate) | Sigma A8381 monohydrate | 0.01 |
| Isoleucine (Ile) | Sigma I2752 | 0.01 |
| Leucine (Leu) | Katayama SAJ 18-1010-2 | 0.01 |
| Phenylalanine (Phe) | Sigma P2126 | 0.01 |
| Valine (Val) | Sigma V0500 | 0.01 |
| Tryptophan (Trp) | Sigma T0254 | 0.01 |
| Tyrosine (Tyr) | Katayama Chemicals 30-5530-2 | 0.01 |
| Glutamine (Gln) | Katayama Chemicals SAJ 12-0950-2 | 0.01 |
| Histidine (His) (monohydrochloride monohydrate) | Sigma H8125 | 0.01 |
| Cysteine (Cys) (hydrochloride monohydrate) | Sigma 05-7470-2 | 0.01 |
| Adenine (Ade) (hemisulfate salt) | Sigma A9126 | 0.01 |
| Uracil (Ura) | Sigma U0750 | 0.01 |

TABLE 6

| Vitamin mix (V) | Product name | Concentration (µg/L) |
|---|---|---|
| Biotin | Wako 023-08711 or SIGMA B4501 | 2 |
| Pantothenic acid Ca | SIGMA P5710 | 400 |
| Folic acid | Wako 062-01801 | 2 |
| Inositol | SIGMA 15-0510-2 | 2000 |
| Niacin | SIGMA A1167 | 400 |
| PABA (p-aminobenzoic acid) | SIGMA A8157 | 200 |
| Pyridoxine hydrochloride | Wako 165-05401 | 400 |
| Riboflavin | SIGMA R4500 | 200 |
| Thiamine hydrochloride | Wako 203-00851 | 400 |
| Boric acid | Kanto Chemicals K8863 | 500 |

TABLE 7

| Metallic ion mix (M) | Product name | Concentration (μg/L) |
|---|---|---|
| Copper sulfate pentahydrate | Katayama 05-6210 | 40 |
| Potassium iodide | Wako 160-03952 | 100 |
| Anhydrous ferric (III) chloride | Wako 093-01672 | 200 |
| Manganese sulfate pentahydrate | Wako 130-13182 | 400 |
| Sodium molybdate dihydrate | Wako 190-02472 | 200 |
| Zinc sulfate heptahydrate | Wako 251-01051 | 400 |

TABLE 8

| Inorganic ion mix (Ion) | Product name | Concentration (mg/L) |
|---|---|---|
| Ammonium sulfate | SIGMA 01-5110-6 | 0.5 |
| $KH_2PO_4$ | SIGMA 24-5260-5 or Katayama Chemicals 24-5260 | 1 |
| $MgSO_4 \cdot 7H_2O$ | Wako 138-00414 or Katayama Chemicals 19-0480 | 0.5 |
| NaCl | SIGMA 28-2270-5 | 0.1 |
| $CaCl \cdot 2H_2O$ | Katayama Chemicals 05-0590 | 0.1 |

(6) Investigation 6

[Investigation of Inorganic Ion Concentration]

Figure 9:
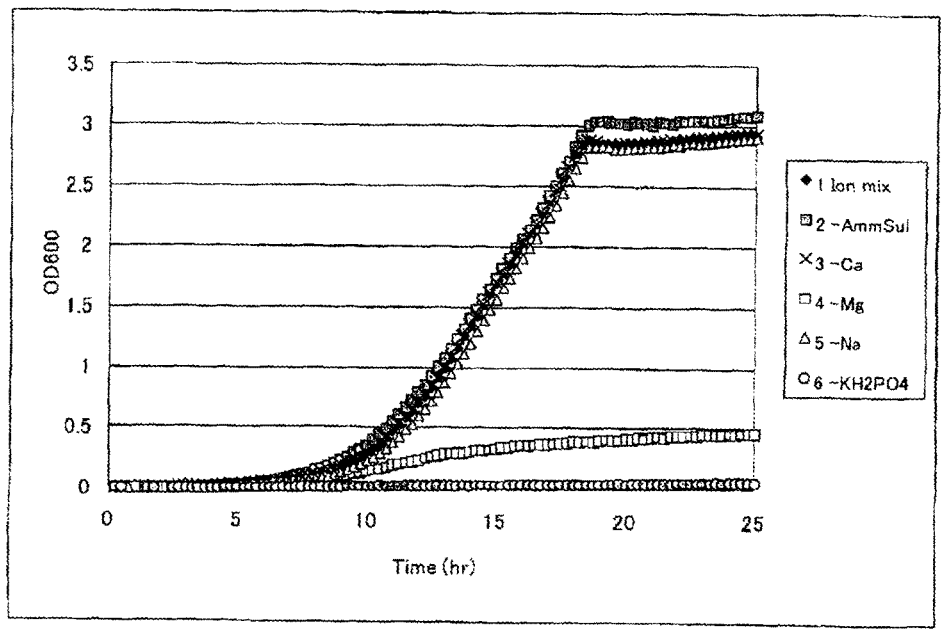
FIG. 9 illustrates results where cultivation was performed in culture mediums in which one component each of the components configuring the inorganic ion mix was eliminated from the SynAA culture medium. Symbol legend 1 (Ion mix) indicates results for the SynAA culture medium (positive control).

Culture mediums were prepared in which one component each of the components configuring the inorganic ion mix was eliminated from the SynAA culture medium, and $OD_{600}$ was measured. Results are shown in FIG. 9. An ion mix to which either $MgSO_4 \cdot 7H_2O$ (represented by Mg in the drawings) or $KH_2PO_4$ is not added was confirmed to have extremely low proliferation. Thereafter, an investigation specifically of inorganic ion concentration was conducted. Moreover, as shown by 2 (ammonium sulfate absent from the SynAA culture medium) in FIG. 9, a culture medium to which ammonium sulfate is not added exhibits a higher proliferation than a culture medium to which the inorganic ion mix has been added; therefore, a determination was made that ammonium sulfate is not essential as the nitrogen source. An investigation was conducted using RAK3599 strain (hereafter, simply referred to as "RAK3599 strain"), which is a strain of Saccharomyces cerevisiae not having a particular nutritional requirement. Where no subsequent special provisions were made, proliferation was investigated by performing roller tube culture for an appropriate amount of time at 28° C. and measuring $OD_{600}$.

(K Ion)

Figure 10:
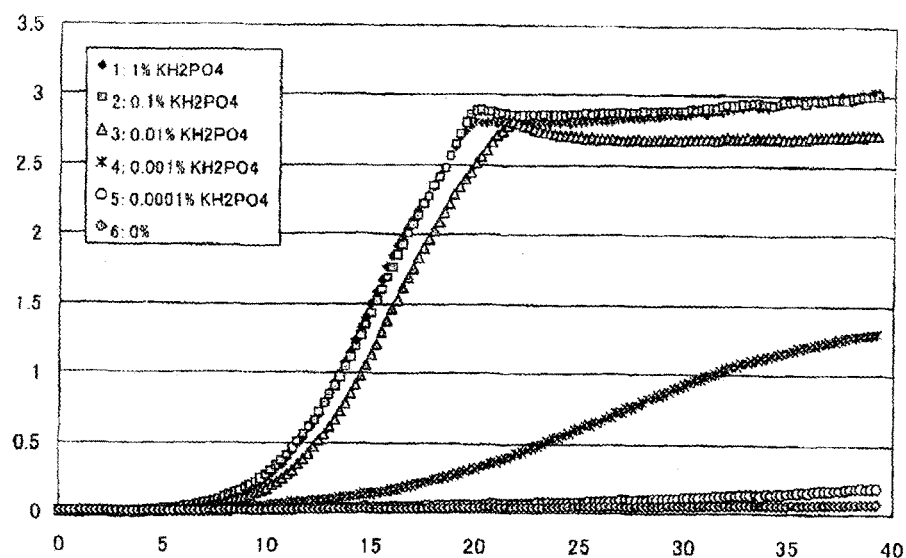
FIG. 10 illustrates proliferation of a *Saccharomyces cerevisiae* RAK3599 strain due to differences in concentration of $KH_2PO_4$ contained in the SynAA culture medium.

$KH_2PO_4$ concentration in the SynAA culture mediums was adjusted to 0%, 0.0001%, 0.001%, 0.01%, 0.1%, and 1%, respectively, and proliferation of the RAK3599 strain was investigated. Results are shown in FIG. 10. Moreover, although not shown in FIG. 10, $OD_{600}$ for 1/100 solutions after 42 hours was 0.02, 0.02, 0.03, 0.11, 0.13, and 0.14, respectively. $OD_{600}$ reached a maximum value at $KH_2PO_4$ concentrations of between 0.1% and 1%.

(Na Ion)

Figure 11:
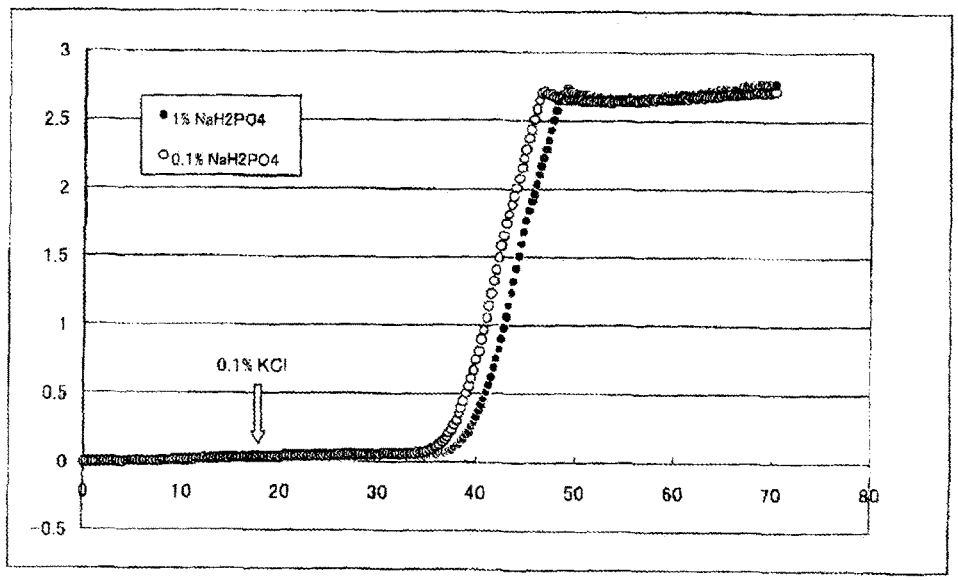
FIG. 11 illustrates proliferation of the *Saccharomyces cerevisiae* RAK3599 strain in a case where 0.1% $NaH_2PO_4$ has been added to the SynAA culture medium instead of $KH_2PO_4$ and, after 20 hours have elapsed, 0.1% KCl is added to the culture medium.

In the SynAA culture medium, 0.1% of $NaH_2PO_4$ (product #28-3790, manufactured by Katayama Co.) was added instead of $KH_2PO_4$ and the RAK3599 strain was cultivated. Even after 20 hours had elapsed, proliferation had not occurred. However, when 0.1% KCl was added after 20 hours had elapsed, proliferation began. Results are shown in FIG. 11. Given these results, K ion was believed to have an important effect on proliferation in the culture medium of the present invention, rather than Na ion.

(Mg Ion)

Figure 12:
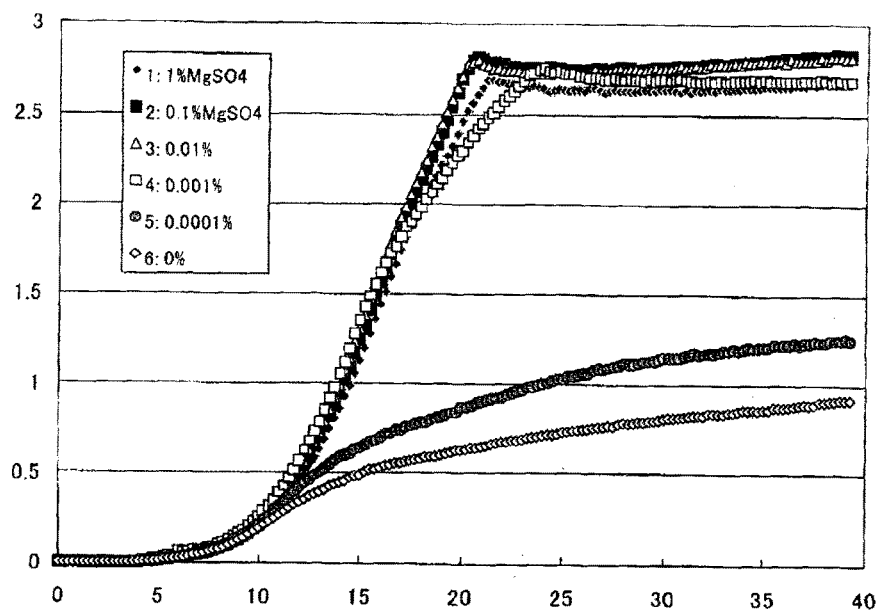
FIG. 12 illustrates proliferation of the *Saccharomyces cerevisiae* RAK3599 strain due to differences in concentration of $MgSO_4$ contained in the SynAA culture medium.
Figure 13:
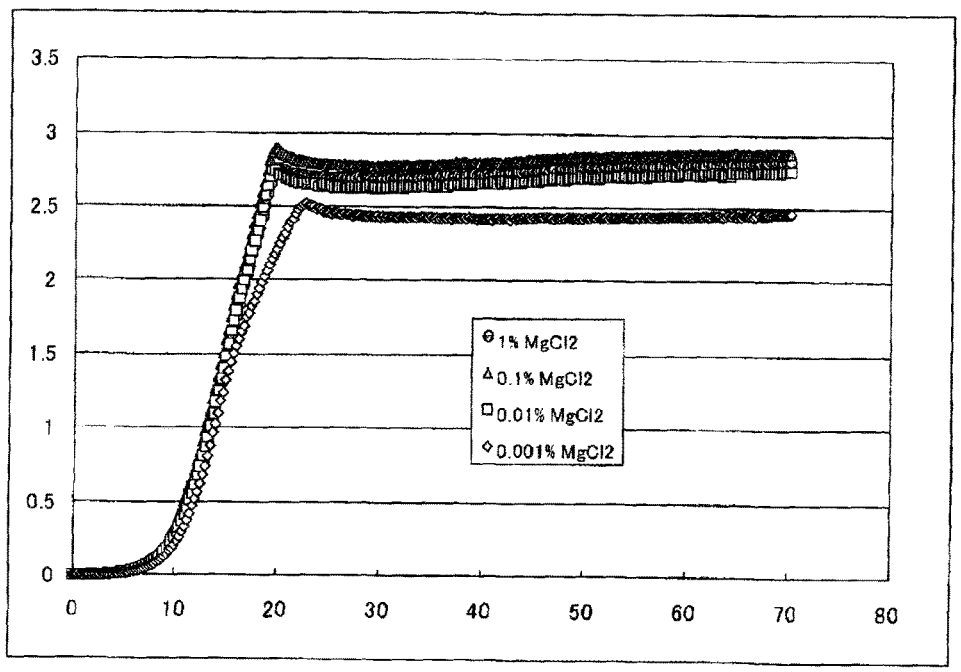
FIG. 13 illustrates proliferation of the *Saccharomyces cerevisiae* RAK3599 strain due to differences in concentration of $MgCl_2$ contained in the SynAA culture medium.

$MgSO_4$ concentration in the SynAA culture mediums was adjusted to 0%, 0.0001%, 0.001%, 0.01%, 0.1%, and 1%, respectively, and proliferation of the RAK3599 strain was investigated. Results are shown in FIG. 12. $OD_{600}$ for 1/100 solutions after 42 hours was 0.02, 0.04, 0.09, 0.12, 0.13, and 0.13, respectively, and reached a maximum value at $MgSO_4$ concentrations of between 0.01% and 1%. Next, $MgCl_2$ concentration in the SynAA culture mediums was adjusted to 0.001%, 0.01%, 0.1%, and 1%, respectively, and proliferation of the RAK3599 strain was investigated. Results are shown in FIG. 13. A maximum value was reached at between 0.01% and 1%, similar to $MgSO_4$, and $Mg^{2+}$ influenced proliferation; however, no particular difference was believed to be present between $SO_4^{2-}$ and $Cl^-$.

(7) Investigation 7

[Investigation of Vitamins]

Figure 14A:
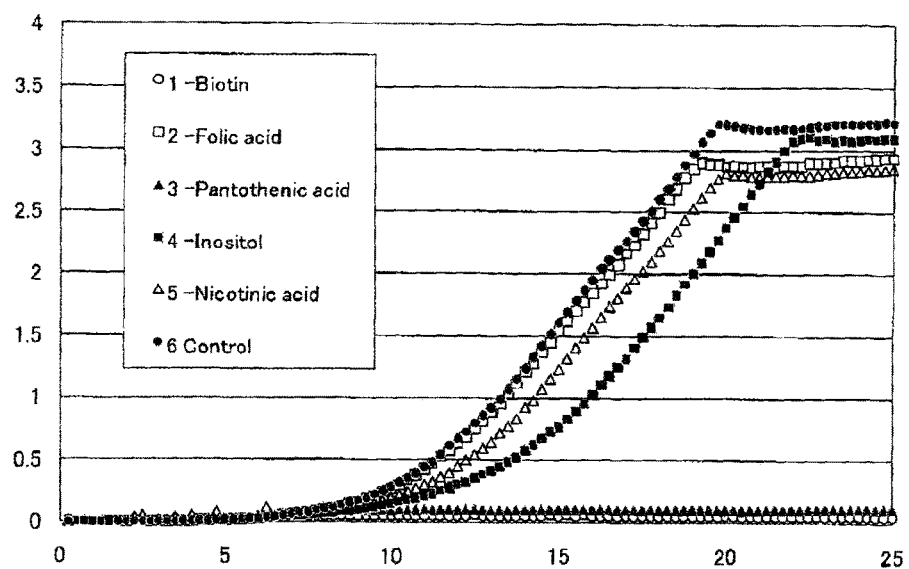
FIG. 14 illustrates results where cultivation was performed in culture mediums in which one component each of the components configuring the vitamin mix was eliminated from the SynAA culture medium. Symbol legend 6 in (a) and "vitamin mix" in (b) indicate results for the SynAA culture medium (positive control).
Figure 14B:
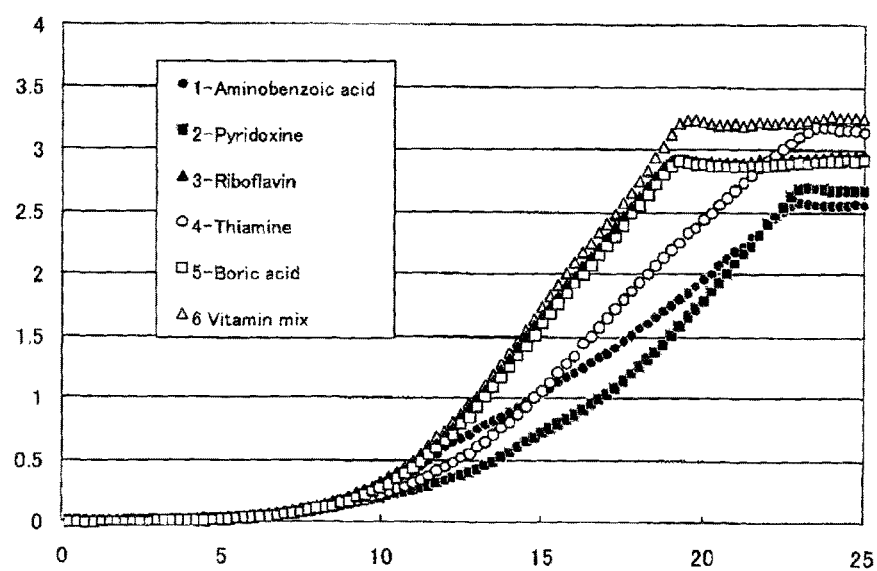

A culture medium was prepared in which one component each of the components configuring the vitamin mix was eliminated from the SynAA culture medium, with the SynAA culture medium as the control, and proliferation of the RAK3599 strain was investigated. Results are shown in FIGS. 14A and 14B. Also, pantothenic acid or biotin were confirmed to be essential components for increasing proliferation of the RAK3599 strain. In addition, folic acid, boric acid, and riboflavin were judged to not be essential components. A further investigation of a required amount of biotin, inositol, nicotinic acid, thiamine, pyridoxine, and pantothenic acid was believed necessary.

(8) Investigation 8

[AKD Culture Medium]

Based on results of investigations to that point, a formulation of a culture medium composition believed to have a high level of proliferation (AKD culture medium) was prepared. An exemplary AKD formulation is as follows.

TABLE 9

| Structural Component | | Mfctr name | g/L | Structural Component | | Mfctr name | g/L |
|---|---|---|---|---|---|---|---|
| Glucose | | Katayama | 20.00 | Asparagine | | Katayama 01-6780 | 0.01 |
| $KH_2PO_4$ | | Sigma 24-5260-5 | 1.00 | Glutamine | | Katayama 12-0950-2 | 0.01 |
| $MgSO_4 \cdot 7H_2O$ | | Katayama 19-0480 | 0.50 | Cysteine | hydrochloride monohydrate | Sigma 05-7470-2 | 0.01 |
| Aspartic acid | Sodium salt monohydrate | Sigma A6683 | 5.00 | Leucine | | Katayama 18-1010-2 | 0.01 |
| Arginine | monohydrochloride | Sigma A5131 | 10.00 | Tryptophan | | Sigma T0254 | 0.01 |
| Lysine | monohydrochloride | Katayama 18-1900 | 1.00 | Histidine | monohydrochloride monohydrate | Sigma H8125 | 0.01 |
| Proline | | Sigma P0380 | 1.00 | Adenine | hemisulfate salt | Sigma A9126 | 0.01 |

TABLE 9-continued

| Structural Component | Mfctr name | g/L | Structural Component | | Mfctr name | g/L |
|---|---|---|---|---|---|---|
| Glutamic acid sodium salt hydrate | Sigma G1626 | 1.00 | Uracil | | Sigma U0750 | 0.01 |
| Alanine | Sigma A7627 | 0.10 | myo-Inositol | | Sigma 15-0510-2 | 2000 μg |
| Isoleucine | Sigma I2752 | 0.01 | Pantothenic acid | Ca | Sigma P5710 | 400 μg |
| Phenylalanine | Sigma P2126 | 0.01 | Nicotinic acid (Niacin) | | Sigma A1167 | 400 μg |
| Valine | Sigma V0500 | 0.01 | Pyridoxine | hydrochloride | Wako 165-05401 | 400 μg |
| Tyrosine | Katayama 30-5530-2 | 0.01 | Thiamine | hydrochloride | Wako 203-00851 | 400 μg |
| Methionine | Sigma M9625 | 0.10 | Biotin | | Wako 023-08711 | 2 μg |
| Serine | Sigma S4500 | 0.10 | Ferric (III) chloride | anhydride | Wako 093-01672 | 200 μg |
| Threonine | Sigma T8625 | 0.10 | Zinc sulfate | heptahydrate | Wako 261-01051 | 400 μg |
| Glycine | Katayama 12-1210 | 0.10 | p-Aminobenzoic acid | | Sigma A8157 | 20 μg |

Figure 15:
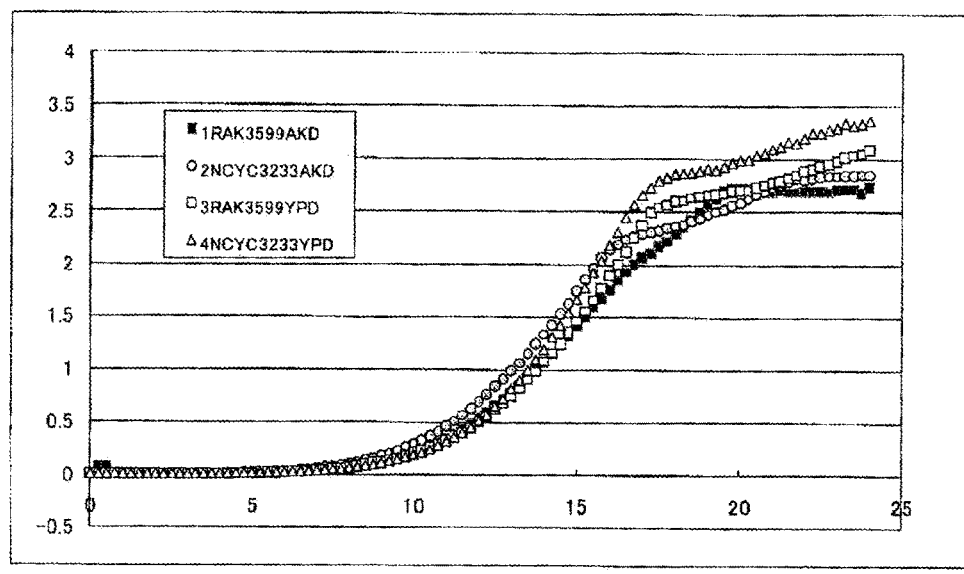
FIG. 15 illustrates a comparison of proliferation in an AKD culture medium and a YPD culture medium using the *Saccharomyces cerevisiae* RAK3599 strain and the *Saccharomyces cerevisiae* NCYC3233 strain.

Herein, proliferation in a YPD culture medium is compared with an AKD culture medium using the *Saccharomyces cerevisiae* RAK3599 strain and the *Saccharomyces cerevisiae* NCYC3233 strain. Results are shown in FIG. 15. The results approached the YPD proliferation curve rather closely, but proliferation of the YPD culture medium was higher, and therefore a decision was made to conduct further investigations into culture medium composition. Investigation began first with amino acids.

(9) Investigation 9
[Investigation of Amino Acid Concentration]
(Nutrition-requiring Strain)

One subject of the present invention is to manufacture a culture medium capable of maintaining a high level of proliferation even for nutrient-requiring yeast strains by cultivating the yeast in the culture medium of the present invention. Therefore, investigations were conducted using nutrient-requiring yeast strains.

(Leucine-requiring Strain)

Figure 16A:
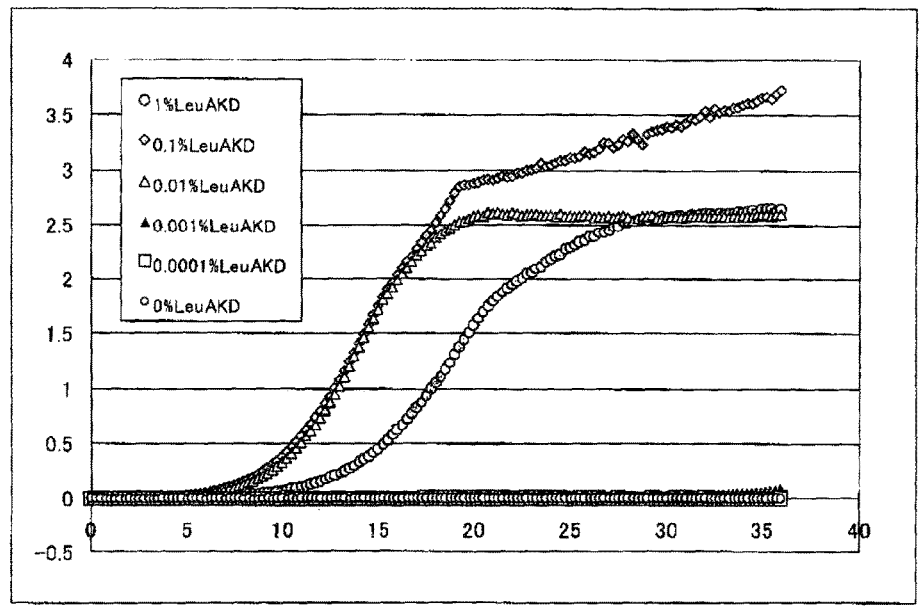
FIG. 16 (a) illustrates proliferation of the *Saccharomyces cerevisiae* leucine-requiring RAK778 strain due to differences in concentration of leucine contained in the AKD culture medium. (b) illustrates proliferation of the *Saccharomyces cerevisiae* RAK3599 strain due to differences in concentration of leucine contained in the AKD culture medium.
Figure 16B:
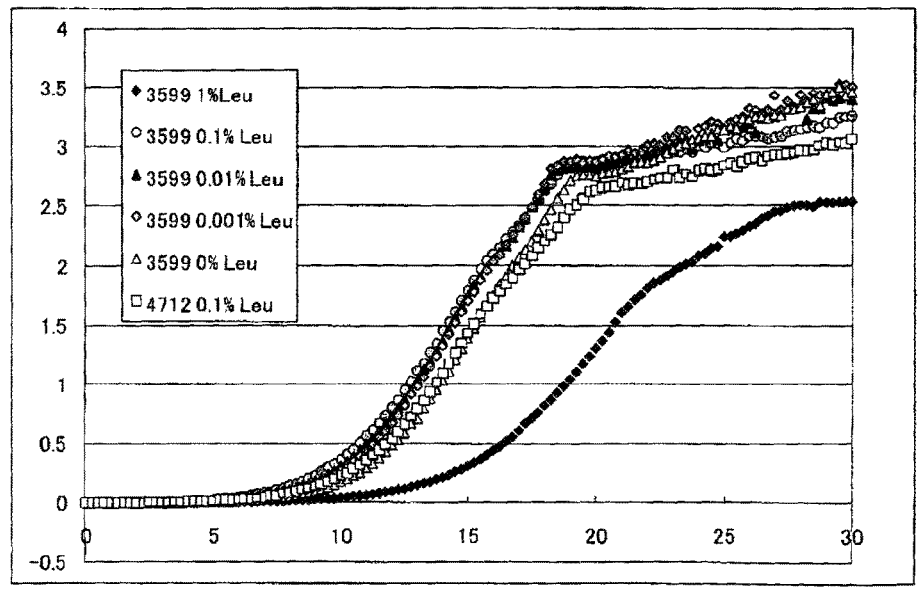

Leucine concentration in the AKD culture mediums was adjusted to 0%, 0.0001%, 0.001%, 0.01%, 0.1%, and 1%, respectively, and proliferation of a *Saccharomyces cerevisiae* leucine-requiring RAK778 strain (BY4712 (leu2Δ0) strain) was investigated. Results are shown in FIG. 16A. Almost no proliferation was observed at a leucine concentration of less than 0.001%; however, proliferation was confirmed to increase at 0.01%, reach a maximum value at 0.1%, and to be inhibited at 1%. Results of a similar experiment conducted using the *Saccharomyces cerevisiae* RAK3599 strain are shown in FIG. 16B. When leucine concentration is between 0 and 0.1%, a high level of proliferation was exhibited; however, proliferation was confirmed to be inhibited at 1%. Given the above-noted results, a preferred leucine concentration was understood to be around 0.1%.

(Histidine-requiring Strain)

Figure 17:
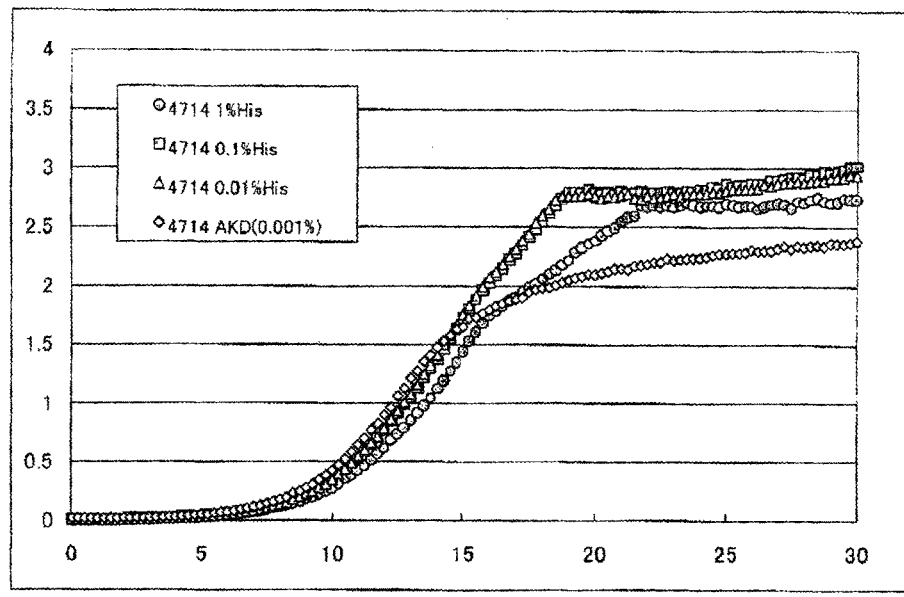
FIG. 17 illustrates proliferation of a *Saccharomyces cerevisiae* histidine-requiring BY4714 strain due to differences in concentration of histidine contained in the AKD culture medium.

Histidine concentration in the AKD culture mediums was adjusted to 0.001%, 0.01%, 0.1%, and 1%, respectively, and proliferation of a *Saccharomyces cerevisiae* histidine-requiring BY4714 (his3Δ1) strain was investigated. Results are shown in FIG. 17. A maximum value was reached between 0.01% and 1%. $OD_{600}$ for 1/100 solutions after 42 hours was 0.07, 0.18, 0.18, and 0.15, respectively. Given the above-noted results, a preferred histidine concentration was understood to be around 0.01%.

(Tryptophan-requiring Strain)

Figure 18:
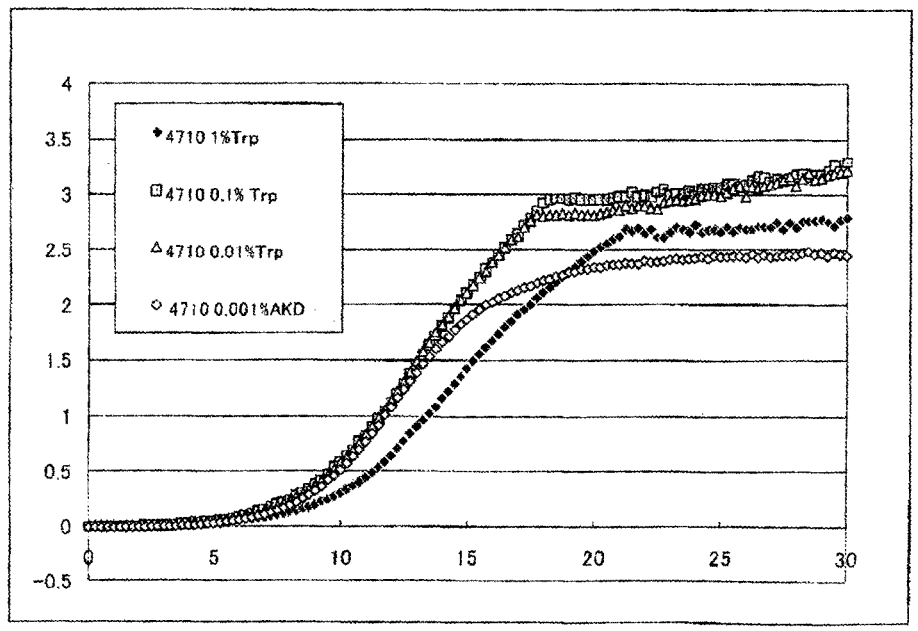
FIG. 18 illustrates proliferation of a *Saccharomyces cerevisiae* tryptophan-requiring BY4710 strain due to differences in concentration of tryptophan contained in the AKD culture medium.

Tryptophan concentration in the AKD culture mediums was adjusted to 0.001%, 0.01%, 0.1%, and 1%, respectively, and proliferation of a *Saccharomyces cerevisiae* tryptophan-requiring BY4710 (trp1Δ) strain was investigated. Results are shown in FIG. 18. $OD_{600}$ for 1/100 solutions after 48 hours was 0.08, 0.15, 0.13, and 0.12, respectively. Proliferation was confirmed to notably increase at 0.01%, and to be somewhat inhibited at 0.1%. Given the above-noted results, a preferred tryptophan concentration was understood to be around 0.01%.

(Uracil-requiring Strain)

Figure 19:
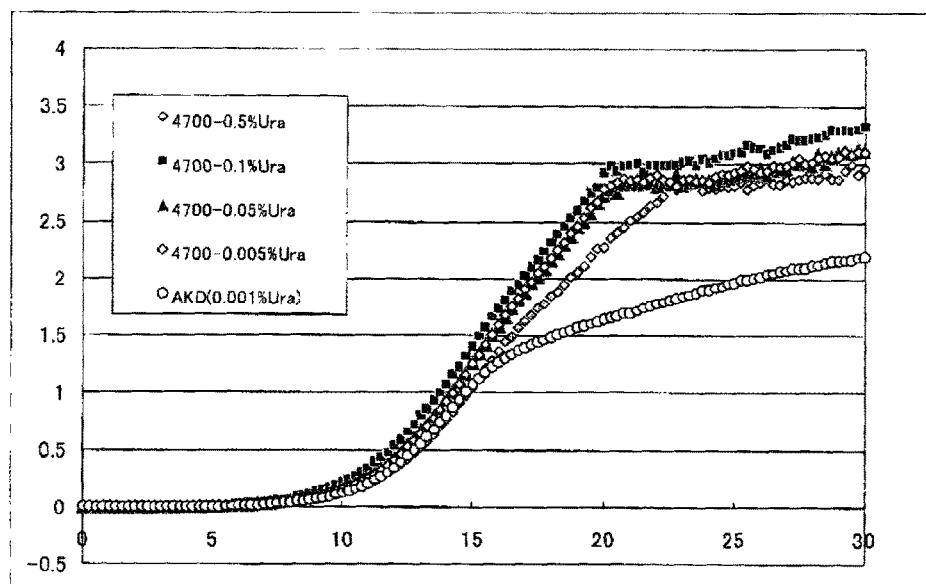
FIG. 19 illustrates proliferation of a *Saccharomyces cerevisiae* uracil-requiring BY4700 strain due to differences in concentration of uracil contained in the AKD culture medium.

A concentration of uracil contained in the amino acid mix of the AKD culture mediums for convenience was adjusted to 0.001%, 0.005%, 0.05%, 0.1%, and 0.5%, respectively, and proliferation of a *Saccharomyces cerevisiae* uracil-requiring BY4700 (ura3Δ) strain was investigated. Results are shown in FIG. 19. $OD_{600}$ for 1/100 solutions after 42 hours was 0.10, 0.21, 0.21, 0.22 and 0.20, respectively. Proliferation was confirmed to be low at 0.001%, to increase at 0.005%. and to markedly increase at between 0.05% and 0.1%. Proliferation was confirmed to be somewhat inhibited at 0.5%. Given the above-noted results, a preferred uracil concentration was understood to be around 0.01%.

(Adenine-requiring Strain)

Figure 20:
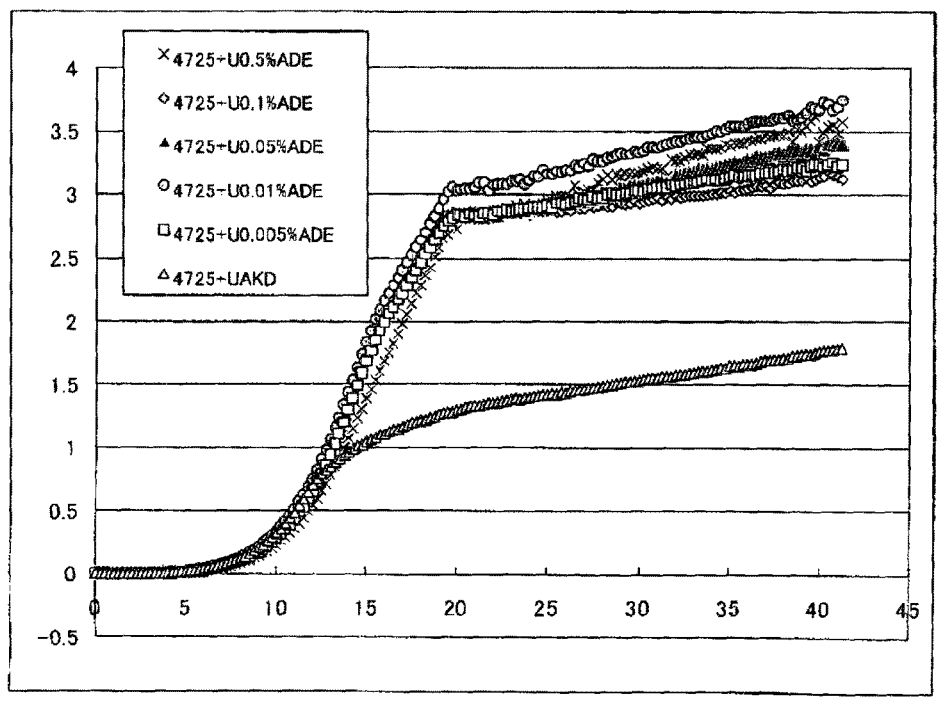
FIG. 20 illustrates proliferation of a *Saccharomyces cerevisiae* adenine-requiring BY4725 strain due to differences in concentration of adenine contained in the AKD culture medium.

A concentration of adenine contained in the amino acid mix of the AKD culture mediums for convenience was adjusted to 0%, 0.005%, 0.01%, 0.05%, 0.1%, and 0.5%, respectively, and proliferation of a *Saccharomyces cerevisiae* adenine-requiring BY4725 (ade2Δ) strain was investigated. Results are shown in FIG. 20. $OD_{600}$ for 1/20 solutions after 42 hours was 4, 15, 18, 18, 13 and 16, respectively. Proliferation was confirmed to be low at 0, to be maximized at between 0.01% and 0.05%, and to be slightly inhibited at 0.1% or more. Given the above-noted results, a preferred adenine concentration was understood to be around 0.01%.

(10) Investigation 10
[AKD' Culture Medium]

Figure 21:
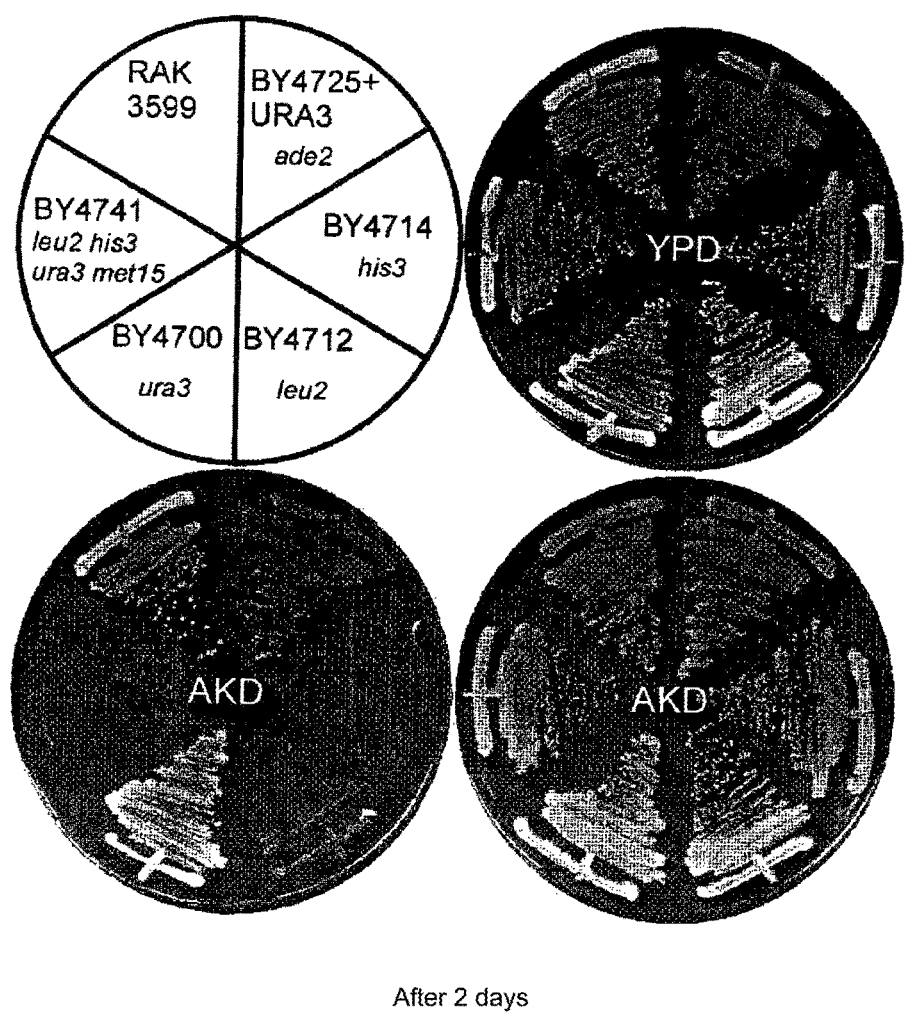
FIG. 21 illustrates proliferation of the *Saccharomyces cerevisiae* BY4741 strain (leu2Δ0 ura3Δ0 his3Δ1 met15Δ0), BY4700 strain (ura3Δ0), BY4712 strain (leu2Δ0), BY4714 strain (his3Δ1), and BY4725+URA3 strain (ade2Δ0) in the AKD culture medium and an AKD' culture medium.

Based on the results of the above amino acid investigations, an AKD' culture medium was prepared as shown in Table 10 below, the AKD' culture medium having increased concentrations of leucine, histidine, tryptophan, uracil, and adenine as compared to the AKD culture medium. Each auxotrophic strain used in Investigation 9 was cultivated for two days at 28° C. in an AKD' agar agar culture medium to which 20 g/L of agar agar (manufactured by Katayama Chemical Industries Co., 101-1900) was added. The AKD culture medium was used as a negative control, and the YPD culture medium was used as a positive control. Results are shown in FIG. 21. As a result, proliferation of the *Saccharomyces cerevisiae* BY4741 strain (leu2Δ0 ura3Δ0 his3Δ1 met15Δ0), BY4700 strain (ura3Δ0), BY4712 strain (leu2Δ0), BY4714 strain (his3Δ1), and BY4725+URA3 strain (ade2Δ0) all improved greatly in comparison to the AKD culture medium, similarly to RAK3599 and a decision was made to conduct further investigations into culture medium composition.

Figure 23:
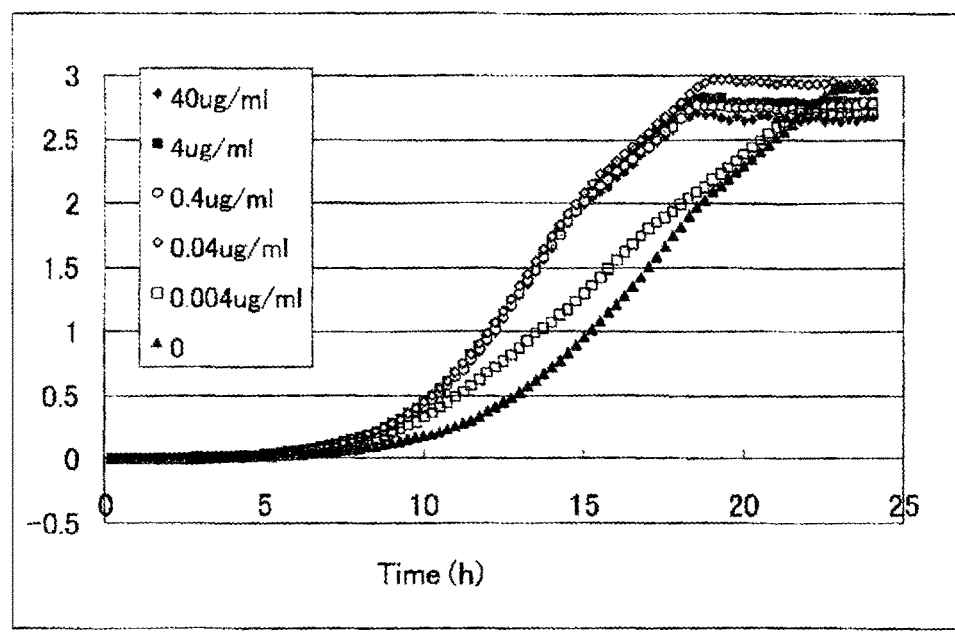
FIG. 23 illustrates proliferation of the RAK3599 strain due to differences in concentration of pyridoxine contained in the AKD' culture medium.

(Pyridoxine)
Pyridoxine concentration in the AKD' culture medium was adjusted to 0, 0.004, 0.04, 0.4, 4, and 40 µg/mL, respectively, and proliferation of the RAK3599 strain was investigated. Results are shown in FIG. 23. A fair degree of proliferation was observed even at a pyridoxine content of 0; however, proliferation increased at 0.04 µg/mL, and reached a maximum value at between 0.4 µg/mL and 40 µg/mL. Given these results, a preferred pyridoxine concentration was understood to be around 400 µg/L.

(Pantothenic Acid)
Pantothenic acid concentration in the AKD' culture medium was adjusted to 0, 0.004, 0.04, 0.4, 4, and 40 µg/mL, respectively, and proliferation of the RAK3599 strain was

TABLE 10

| Structural Component | Mfctr name | | g/L | Structural Component | | Mfctr name | g/L |
|---|---|---|---|---|---|---|---|
| Glucose | | Katayama | 20.00 | Asparagine | | Katayama 01-6780 | 0.01 |
| KH$_2$PO$_4$ | | Sigma 24-5260-5 | 1.00 | Glutamine | | Katayama 12-0950-2 | 0.01 |
| MgSO$_4$•7H$_2$O | | Katayama 19-0480 | 0.50 | Cysteine | hydrochloride monohydrate | Sigma 05-7470-2 | 0.01 |
| Aspartic acid | Sodium salt monohydrate | Sigma A6683 | 5.00 | Leucine | | Katayama 18-1010-2 | 1.00 |
| Arginine | monohydrochloride | Sigma A5131 | 10.00 | Tryptophan | | Sigma T0254 | 0.1 |
| Lysine | monohydrochloride | Katayama 18-1900 | 1.00 | Histidine | monohydrochloride monohydrate | Sigma H8125 | 0.1 |
| Proline | | Sigma P0380 | 1.00 | Adenine | hemisulfate salt | Sigma A9126 | 0.1 |
| Glutamic acid | sodium salt hydrate | Sigma G1626 | 1.00 | Uracil | | Sigma U0750 | 0.1 |
| Alanine | | Sigma A7627 | 0.10 | myo-Inositol | | Sigma 15-0510-2 | 2000 µg |
| Isoleucine | | Sigma I2752 | 0.01 | Pantothenic acid | Ca | Sigma P5710 | 400 µg |
| Phenylalanine | | Sigma P2126 | 0.01 | Nicotinic acid (Niacin) | | Sigma A1167 | 400 µg |
| Valine | | Sigma V0500 | 0.01 | Pyridoxine | hydrochloride | Wako 165-05401 | 400 µg |
| Tyrosine | | Katayama 30-5530-2 | 0.01 | Thiamine | hydrochloride | Wako 203-00851 | 400 µg |
| Methionine | | Sigma M9625 | 0.10 | Biotin | | Wako 023-08711 | 2 µg |
| Serine | | Sigma S4500 | 0.10 | Ferric (III) chloride | anhydride | Wako 093-01672 | 200 µg |
| Threonine | | Sigma T8625 | 0.10 | Zinc sulfate | heptahydrate | Wako 261-01051 | 400 µg |
| Glycine | | Katayama 12-1210 | 0.10 | p-Aminobenzoic acid | | Sigma A8157 | 20 µg |

(11) Investigation 11
[Investigation of Vitamin Concentration]
As noted above, inorganic ion concentration and amino acid concentration were investigated in detail. Next, a decision was made to investigate vitamin concentration. Biotin, pyridoxine, pantothenic acid, thiamine, nicotinic acid, and inositol were targeted as the vitamins.

Figure 22:
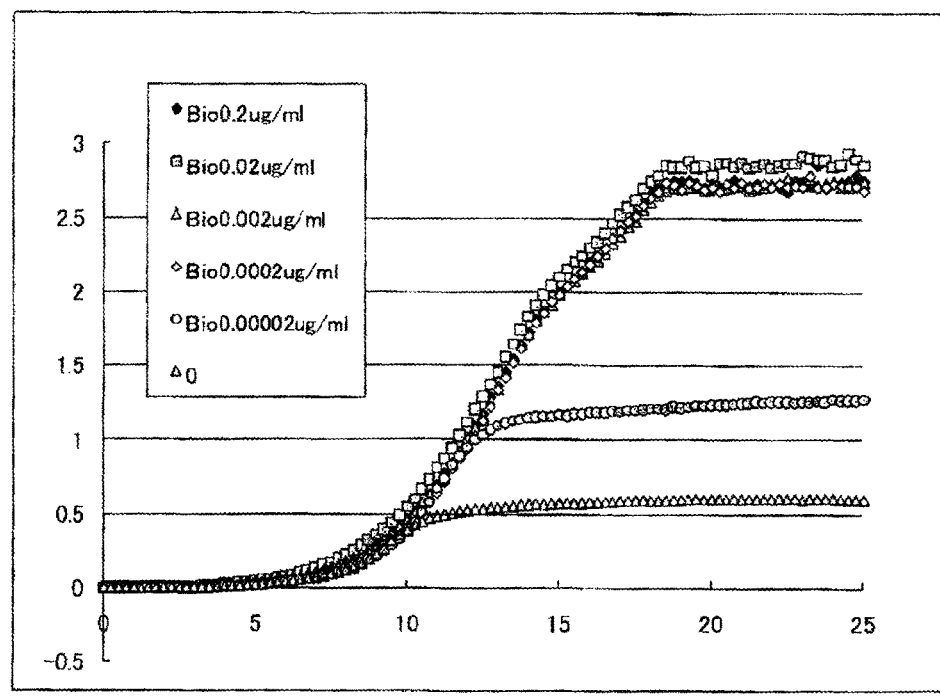
FIG. 22 illustrates proliferation of the *Saccharomyces cerevisiae* RAK3599 strain due to differences in concentration of biotin contained in the AKD' culture medium.
Figure 24:
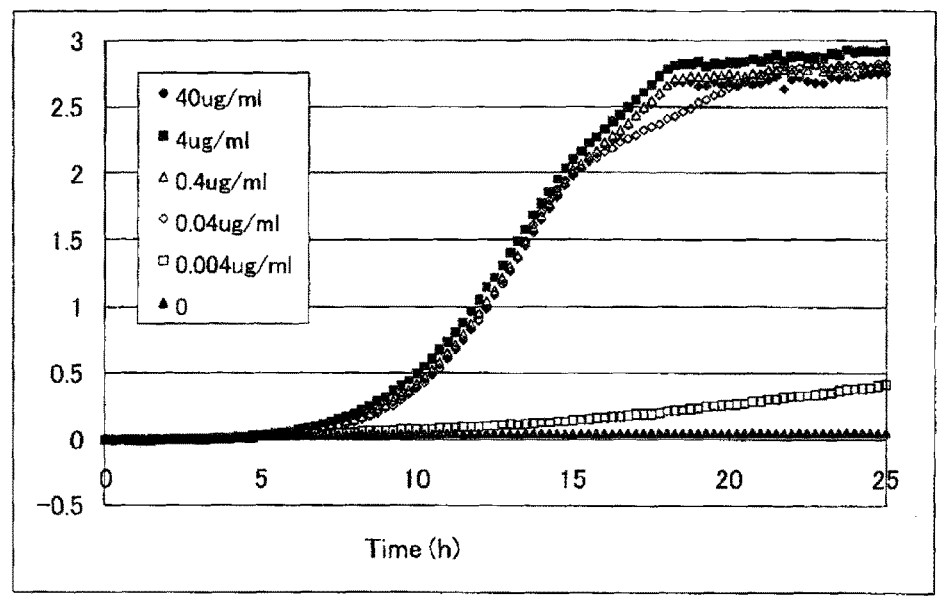
FIG. 24 illustrates proliferation of the RAK3599 strain due to differences in concentration of pantothenic acid contained in the AKD' culture medium.

(Biotin)
Biotin concentration in the AKD' culture medium was adjusted to 0, 0.02 ng/mL, 0.2 ng/mL, 2 ng/mL, 0.02 µg/mL, and 0.2 µg/mL, respectively, and proliferation of the RAK3599 strain was investigated. Results are shown in FIG. 22. Almost no proliferation was observed at a biotin content of 0; however, proliferation was confirmed to reach a maximum value at between 0.2 µg/L and 20 µg/L, and to be slightly inhibited at 200 µg/L. Given these results, a preferred biotin concentration was understood to be around 2 µg/L.

investigated. Results are shown in FIG. 24. At a pantothenic acid content of 0, no proliferation whatsoever occurred, confirming at least that pantothenic acid is an essential component for *Saccharomyces cerevisiae*. Proliferation was confirmed to increase at 0.04 µg/mL, to reach a maximum value at between 0.4 µg/mL and 4 µg/mL, and to be slightly inhibited at 40 µg/mL. Given these results, a preferred pantothenic acid concentration was understood to be around 4000 µg/L.

Figure 25:
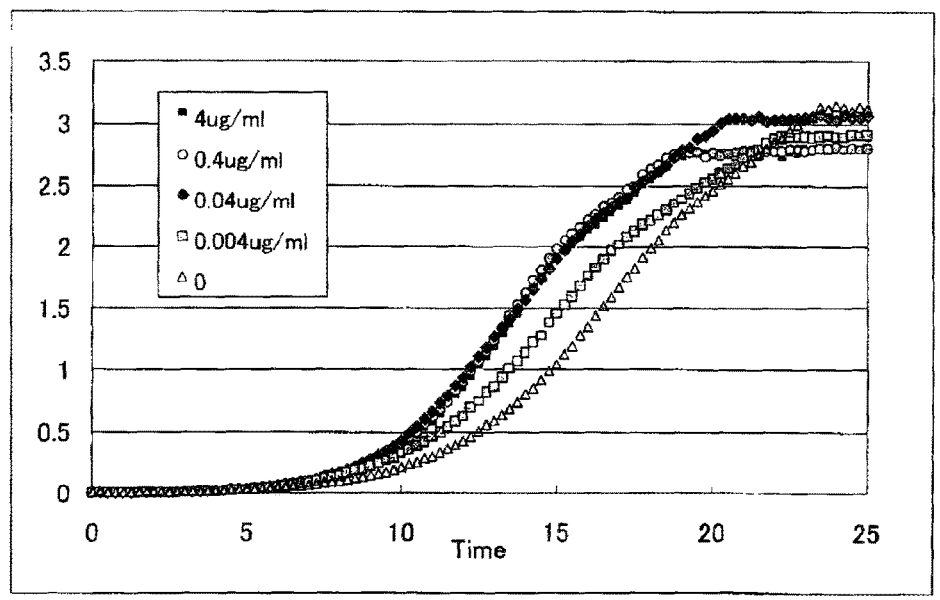
FIG. 25 illustrates proliferation of the RAK3599 strain due to differences in concentration of thiamine contained in the AKD' culture medium.

(Thiamine)
Thiamine concentration in the AKD' culture medium was adjusted to 0, 0.004, 0.04, 0.4, 4, and 40 µg/mL, respectively, and proliferation of the RAK3599 strain was investigated. Results are shown in FIG. 25. A fair degree of proliferation was observed even at a thiamine content of 0; however, proliferation reached a maximum value at between 0.4 µg/mL and 4 µg/mL. Given these results, a preferred thiamine concentration was understood to be around 400 µg/L.

(Nicotinic Acid)

Figure 26:
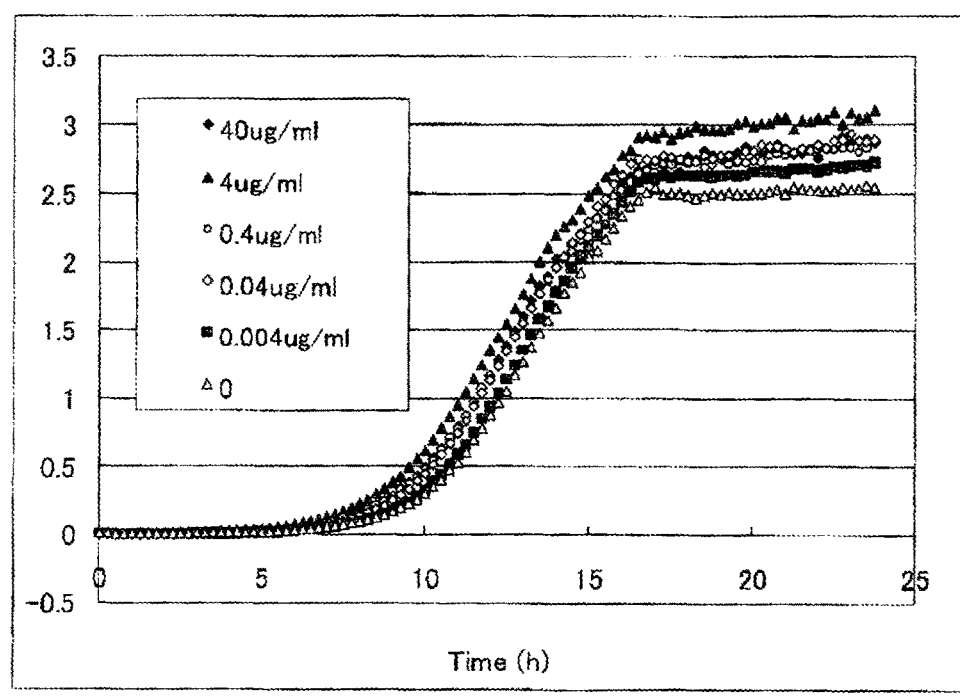
FIG. 26 illustrates proliferation of the RAK3599 strain due to differences in concentration of nicotinic acid contained in the AKD' culture medium.

Nicotinic acid concentration in the AKD' culture medium was adjusted to 0, 0.004, 0.04, 0.4, 4, and 40 µg/mL, respectively, and proliferation of the RAK3599 strain was investigated. Results are shown in FIG. 26. Although not shown clearly in FIG. 26, $OD_{600}$ after 24 hours was 9, 10, 10, 9, 10, and 8, respectively. A significant degree of proliferation was observed even at a nicotinic acid content of 0; however, proliferation increased at 0.04 µg/mL, and reached a maximum value at 4 µg/mL. Proliferation was confirmed to be somewhat inhibited at 40 µg/mL. Given these results, a preferred nicotinic acid concentration was understood to be around 4000 µg/L.

(Inositol)

Figure 27A:
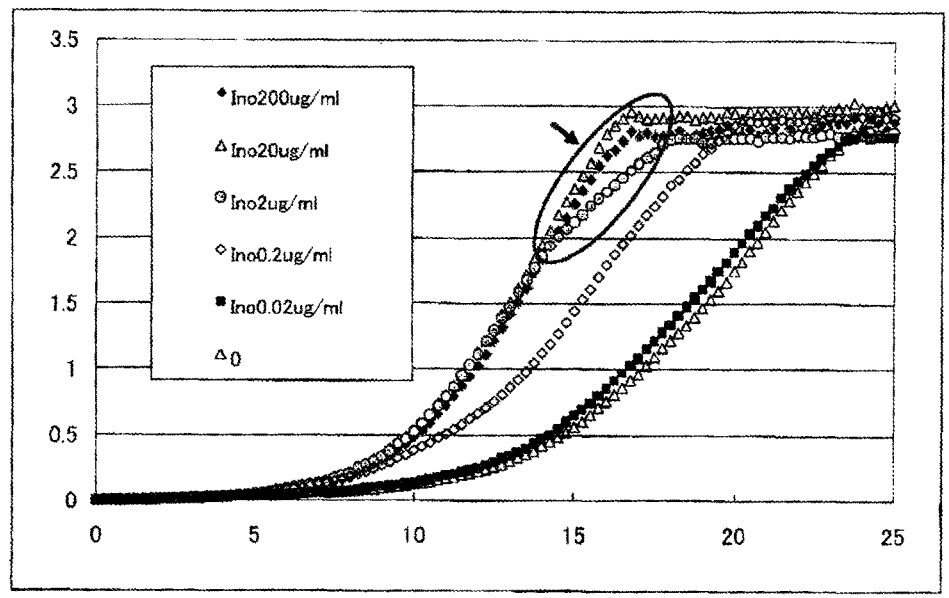
FIG. 27 illustrates proliferation of the RAK3599 strain due to differences in concentration of inositol contained in the AKD' culture medium. (a) and (b) investigate different concentrations.
Figure 27B:
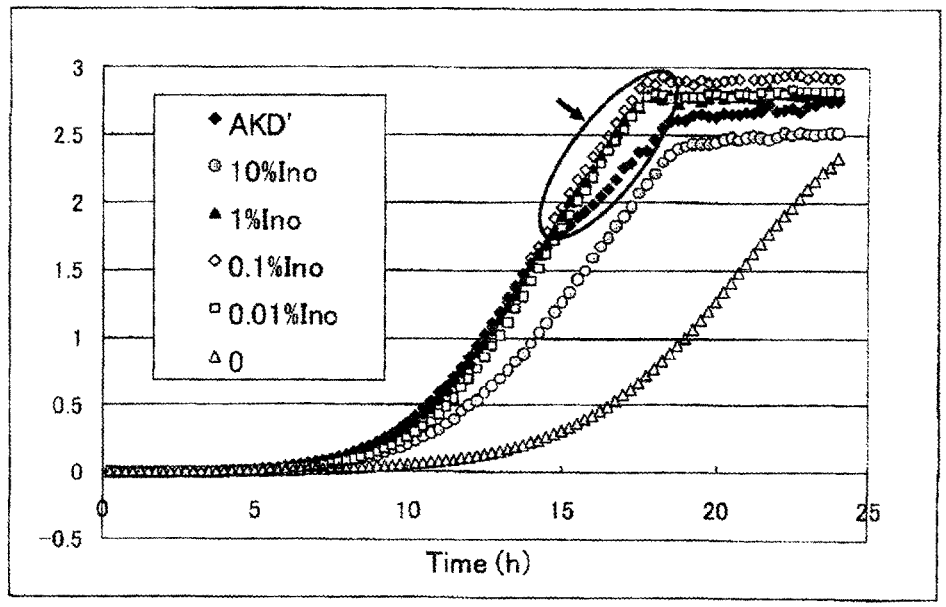

Myo-inositol concentration in the AKD' culture medium was adjusted to 0, 0.02 µg/mL, 0.2 µg/mL, 2 µg/mL, 20 µg/mL, and 200 µg/mL, respectively, and proliferation of the RAK 3599 strain was investigated. Results are shown in FIG. 27A. Proliferation increased in proportion to an increase in inositol content. Given this, inositol concentration in the AKD' culture medium was adjusted to 0, 0.01%, 0.1%, 1%, and 10% (equivalent to 100 g/L), respectively, and proliferation of the RAK3599 strain was investigated. Results are shown in FIG. 27B. At the maximum value, at between 0.01% and 1%, proliferation of the AKD', which until that point it had not been possible to resolve, was surpassed; an increase in slope (i.e., elevation of a line (arrow in the drawing)) of the proliferation curve was confirmed that erased a difference with YPD; and unexpected information was obtained to the effect that inositol is a rate-limiting step. Moreover, in a case where inositol is added at 10%, proliferation was confirmed to be below that of AKD'. Accordingly, a preferred inositol concentration was understood to be between 50 and 10,000 mg/L.

(12) Investigation 12 [Investigation of Metallic Ion Concentration]

Figure 28:
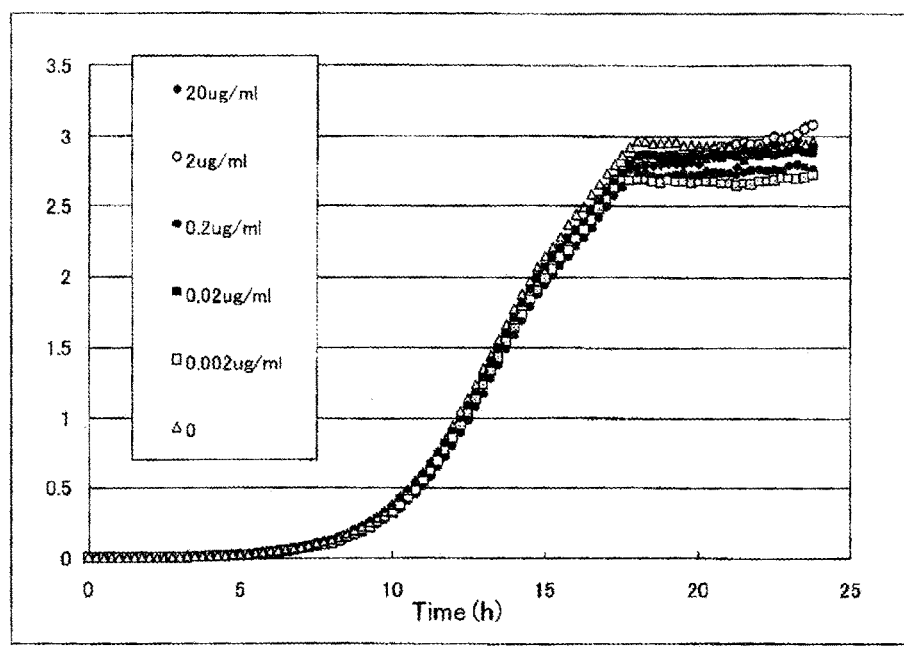
FIG. 28 illustrates proliferation of the RAK3599 strain due to differences in concentration of $FeCl_3$ contained in the AKD' culture medium.

Continuing from the inorganic ion concentration, amino acid concentration, and vitamin concentration, a decision was made to investigate Fe ion (metallic ion) concentration. $FeCl_3$ concentration in the AKD' culture medium was adjusted to 0, 0.002, 0.02, 0.2, 2, and 20 µg/mL, respectively, and proliferation of the RAK3599 strain was investigated. Results are shown in FIG. 28. Although not shown clearly in FIG. 28, $OD_{600}$ after 24 hours was 10, 9, 11, 10, 13, and 14, respectively. A high level of proliferation was exhibited at between 2 and 20 µg/mL. Given these results, a preferred $FeCl_3$ concentration was understood to be around 4000 µg/L.

(13) Investigation 13

[AID Culture Medium] (Culture Medium A of the Present Invention)

In the above, given the results of investigations of Fe ion concentration and vitamin concentration, a culture medium 1 (AID culture medium) according to the present invention was prepared in which additive amounts of iron, pantothenic acid, inositol, and the like were increased as compared with the AKD' culture medium. An exemplary AID culture medium formulation is as follows.

TABLE 11

| Structural Component | Mfctr name | | g/L | Structural Component | | Mfctr name | g/L |
|---|---|---|---|---|---|---|---|
| Glucose | | Katayama | 20.00 | Asparagine | | Katayama 01-6780 | 0.01 |
| $KH_2PO_4$ | | Sigma 24-5260-5 | 1.00 | Glutamine | | Katayama 12-0950-2 | 0.01 |
| $MgSO_4 \cdot 7H_2O$ | | Katayama 19-0480 | 0.50 | Cysteine | hydrochloride monohydrate | Sigma 05-7470-2 | 0.01 |
| Aspartic acid | Sodium salt monohydrate | Sigma A6683 | 5.00 | Leucine | | Katayama 18-1010-2 | 1.00 |
| Arginine | monohydrochloride | Sigma A5131 | 10.00 | Tryptophan | | Sigma T0254 | 0.1 |
| Lysine | monohydrochloride | Katayama 18-1900 | 1.00 | Histidine | monohydrochloride monohydrate | Sigma H8125 | 0.1 |
| Proline | | Sigma P0380 | 1.00 | Adenine | hemisulfate salt | Sigma A9126 | 0.1 |
| Glutamic acid | sodium salt hydrate | Sigma G1626 | 1.00 | Uracil | | Sigma U0750 | 0.1 |
| Alanine | | Sigma A7627 | 0.10 | myo-Inositol | | Sigma 15-0510-2 | 1.00 |
| Isoleucine | | Sigma I2752 | 0.01 | Pantothenic acid | Ca | Sigma P5710 | 4000 µg |
| Phenylalanine | | Sigma P2126 | 0.01 | Nicotinic acid (Niacin) | | Sigma A1167 | 4000 µg |
| Valine | | Sigma V0500 | 0.01 | Pyridoxine | hydrochloride | Wako 165-05401 | 400 µg |
| Tyrosine | | Katayama 30-5530-2 | 0.01 | Thiamine | hydrochloride | Wako 203-00851 | 400 µg |
| Methionine | | Sigma M9625 | 0.10 | Biotin | | Wako 023-08711 | 2 µg |
| Serine | | Sigma S4500 | 0.10 | Ferric (III) chloride | anhydride | Wako 093-01672 | 4000 µg |
| Threonine | | Sigma T8625 | 0.10 | Zinc sulfate | heptahydrate | Wako 261-01051 | 400 µg |
| Glycine | | Katayama 12-1210 | 0.10 | p-Aminobenzoic acid | | Sigma A8157 | 20 µg |

(Investigation with AID Culture Medium)

As shown in the following, an investigation was conducted into concentrations of each amino acid and a substitution potential of pantothenic acid for the amino acid in the AID culture medium. A suitable YPD culture medium was used as a control.

(Alanine, Methionine, Serine, Threonine, Glycine, Glutamine, Cysteine, Asparagine, Isoleucine, Phenylalanine, and Valine)

Figure 29A:
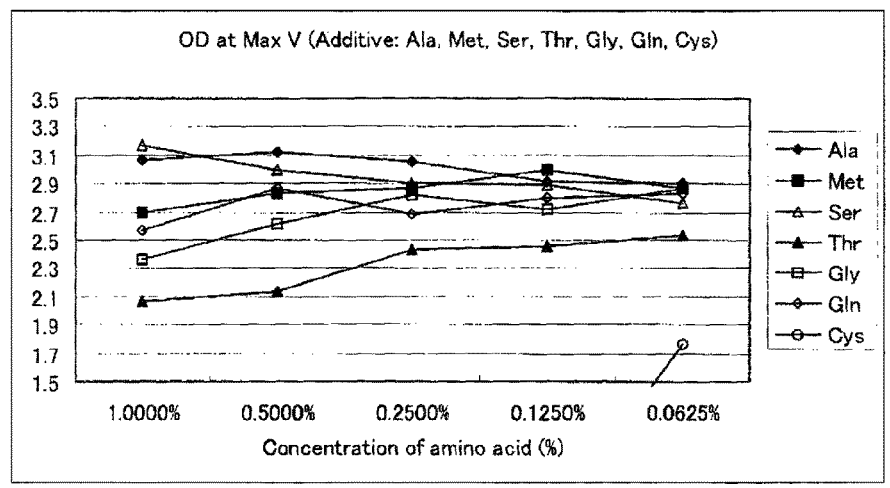
FIG. 29 illustrates concentration inhibition of (a) each of amino acids alanine, methionine, serine, threonine, glycine, glutamine, and cysteine; and (b) each of amino acids asparagine, isoleucine, phenylalanine, and valine added to an AID culture medium.
Figure 29B:
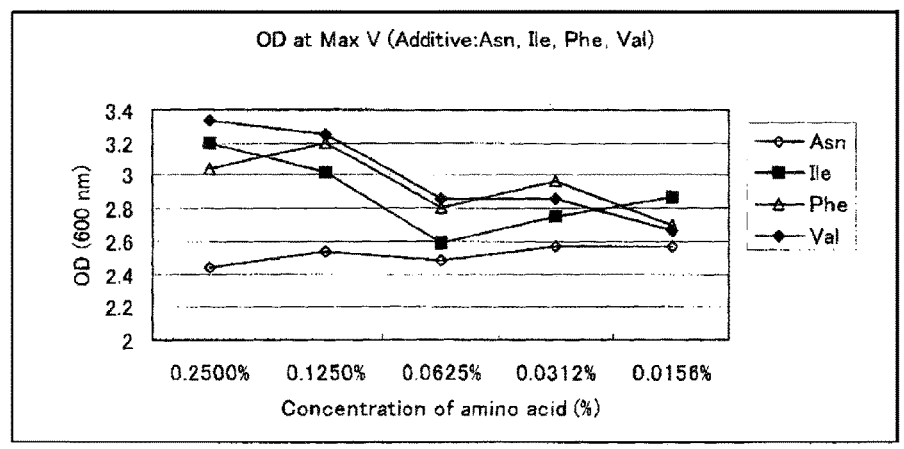

The amino acids alanine, methionine, serine, threonine, glycine, glutamine, and cysteine added to the AID culture medium were each adjusted to a culture medium additive concentration of 0.0625%, 0.125%, 0.25%, 0.5%, and 1%, and $OD_{600}$ was measured. Results are shown in FIG. 29A. Next, the amino acids asparagine, isoleucine, phenylalanine, and valine were each adjusted to a culture medium additive concentration of 0.156%, 0.0312%, 0.0625%, 0.1250%, and 0.2500%, and $OD_{600}$ was measured after 24 hours. According to the results of FIGS. 29A and 29B, when methionine, threonine, glycine, glutamine, cysteine, and asparagine were added at high concentrations, proliferation was confirmed to be inhibited. Meanwhile, even when alanine, serine, isoleucine, phenylalanine, and valine were added at high concentrations, a positive influence was imparted to proliferation.

(Tyrosine)

Figure 30:
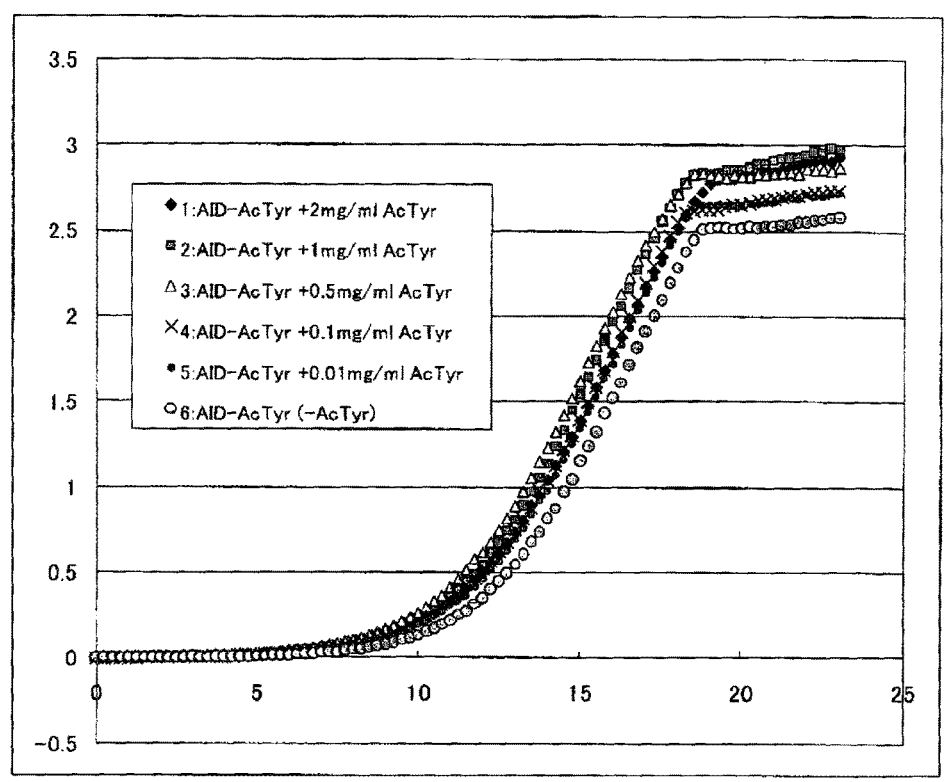
FIG. 30 illustrates proliferation of the RAK3599 strain due to differences in concentration of acetyl tyrosine contained in the AID culture medium.

Tyrosine has low solubility, and was investigated at a concentration of 0.01 g/L to this point. However, a decision was made to use acetyl tyrosine (aY) instead of tyrosine to increase solubility. Proliferation of the RAK3599 strain was investigated in AID culture mediums where acetyl tyrosine (A2513, manufactured by Sigma Co.) concentration was adjusted to 0, 0.01, 0.1, 0.5, 1, and 2 mg/mL, respectively. Results are shown in FIG. 30. Although not shown clearly in FIG. 30, $OD_{600}$ after 24 hours was 13, 14, 15, 14, 15, and 18, respectively. Given these results, going forward, a decision was made to use acetyl tyrosine as a tyrosine derivative and an acetyl tyrosine concentration of about 1 g/L was determined to be preferred.

(Alanine)

Figure 31:
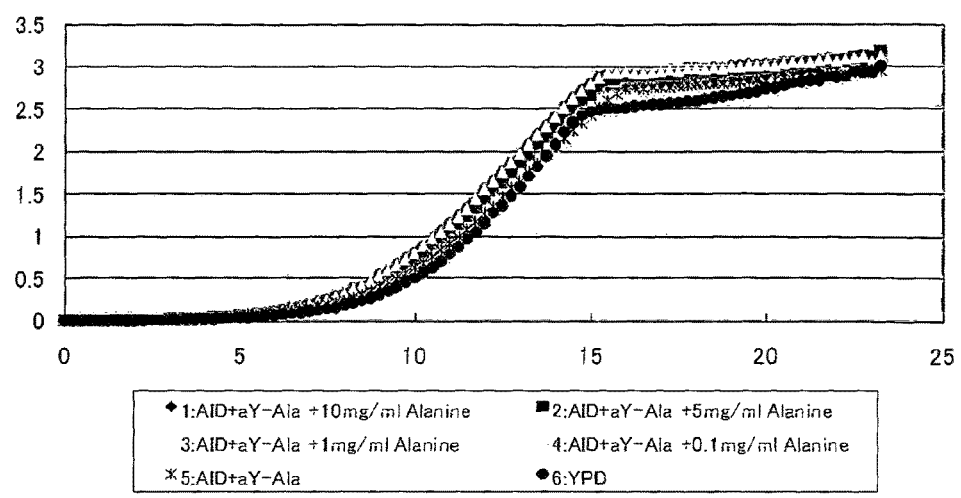
FIG. 31 illustrates proliferation of the RAK3599 strain due to differences in concentration of alanine contained in the AID culture medium.

Alanine concentration in the AID culture medium to which 1 g/L acetyl tyrosine was added (aY-AID culture medium) was adjusted to 0, 0.1, 1, 5, and 10 mg/mL, respectively, and proliferation of the RAK3599 strain was investigated. Results are shown in FIG. 31. Although not shown clearly in FIG. 31, $OD_{600}$ after 24 hours was 17, 18, 18, 17, and 18, respectively. Given these results, a determination was made that the slope of the proliferation curve is greatest at an alanine content of around 1 mg/mL.

(Isoleucine)

Figure 32:
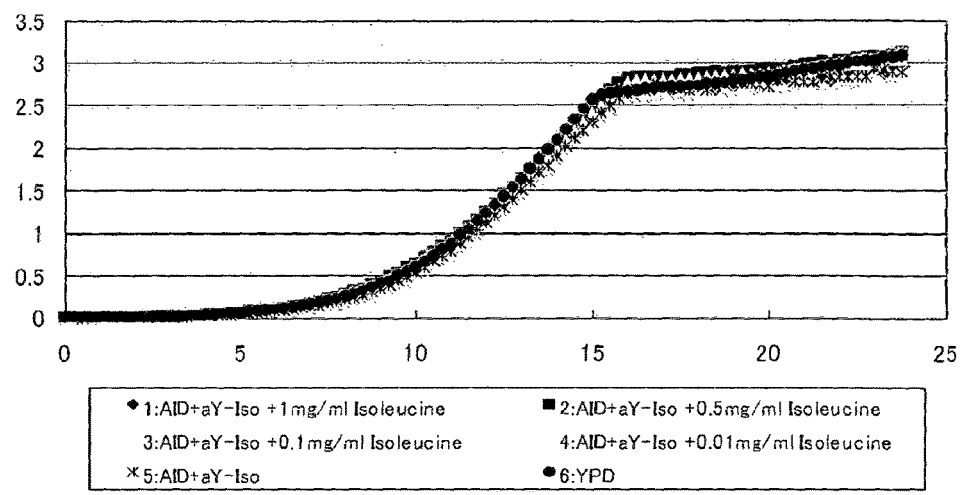
FIG. 32 illustrates proliferation of the RAK3599 strain due to differences in concentration of isoleucine contained in the AID culture medium.

Isoleucine concentration in the aY-AID culture medium was adjusted to 0, 0.01 mg/mL, 0.1 mg/mL, 0.5 mg/mL, and 1 mg/mL, respectively, and proliferation of the RAK3599 strain was investigated. Results are shown in FIG. 32. Although not shown clearly in FIG. 32, $OD_{600}$ after 24 hours was 16, 17, 16, 17, and 19, respectively. Given these results, a preferred isoleucine content was understood to be around 1 g/L.

(Phenylalanine)

Figure 33:
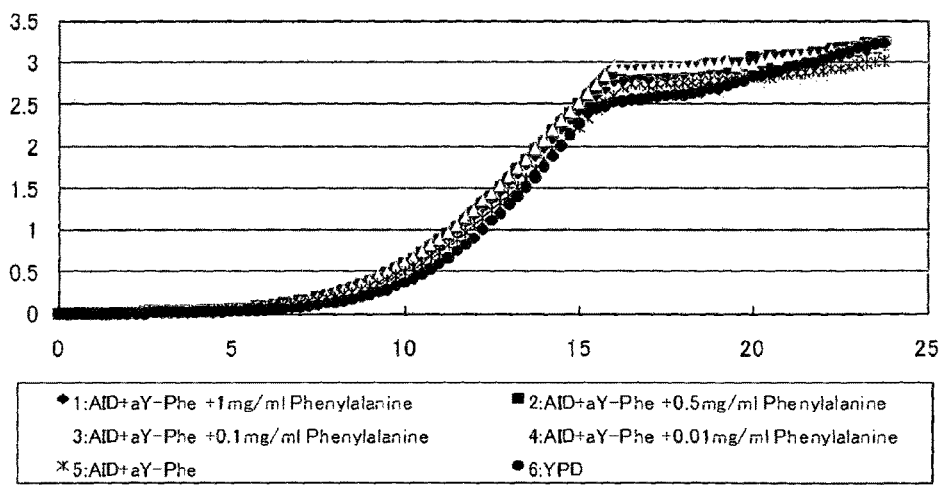
FIG. 33 illustrates proliferation of the RAK3599 strain due to differences in concentration of phenylalanine contained in the AID culture medium.

Phenylalanine concentration in the aY-AID culture medium was adjusted to 0, 0.01, 0.1, 0.5, and 1 mg/mL, respectively, and proliferation of the RAK3599 strain was investigated. Results are shown in FIG. 33. Although not shown clearly in FIG. 33, $OD_{600}$ after 24 hours was 17, 17, 19, 19, and 19, respectively. Given these results, a preferred phenylalanine content was understood to be around 1 g/L.

(Valine)

Figure 34:
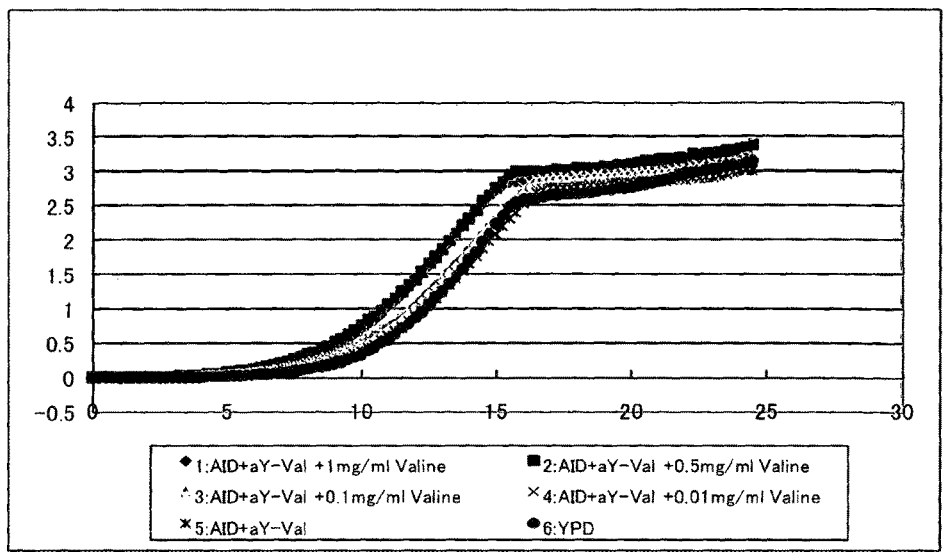
FIG. 34 illustrates proliferation of the RAK3599 strain due to differences in concentration of valine contained in the AID culture medium.

Valine concentration in the aY-AID culture medium was adjusted to 0, 0.01, 0.1, 0.5, and 1 mg/mL, respectively, and proliferation of the RAK3599 strain was investigated. Results are shown in FIG. 34. Although not shown clearly in FIG. 34, $OD_{600}$ after 24 hours was 16, 15, 15, 16, and 16, respectively. Given these results, a preferred valine content was understood to be around 1 g/L.

(Serine)

Figure 35:
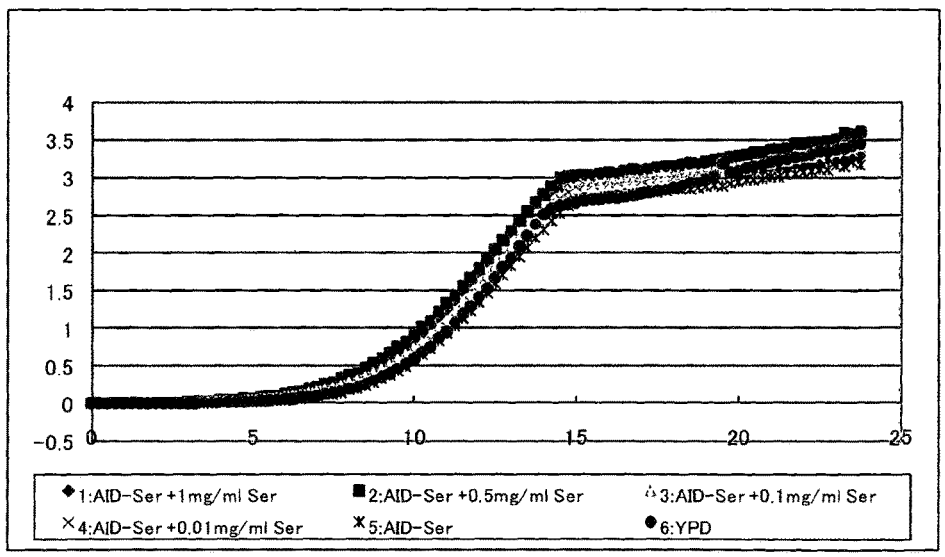
FIG. 35 illustrates proliferation of the RAK3599 strain due to differences in concentration of serine contained in the AID culture medium.

Serine concentration in the AID culture medium was adjusted to 0, 0.01 mg/mL, 0.1 mg/mL, 0.5 mg/mL, and 1 mg/mL, respectively, and proliferation of the RAK3599 strain was investigated. Results are shown in FIG. 35. According to the results in FIG. 35, proliferation was confirmed to particularly increase at a serine content of around 0.5 mg/mL. Given these results, a preferred serine content was understood to be around 0.5 g/L.

(Threonine)

Figure 36:
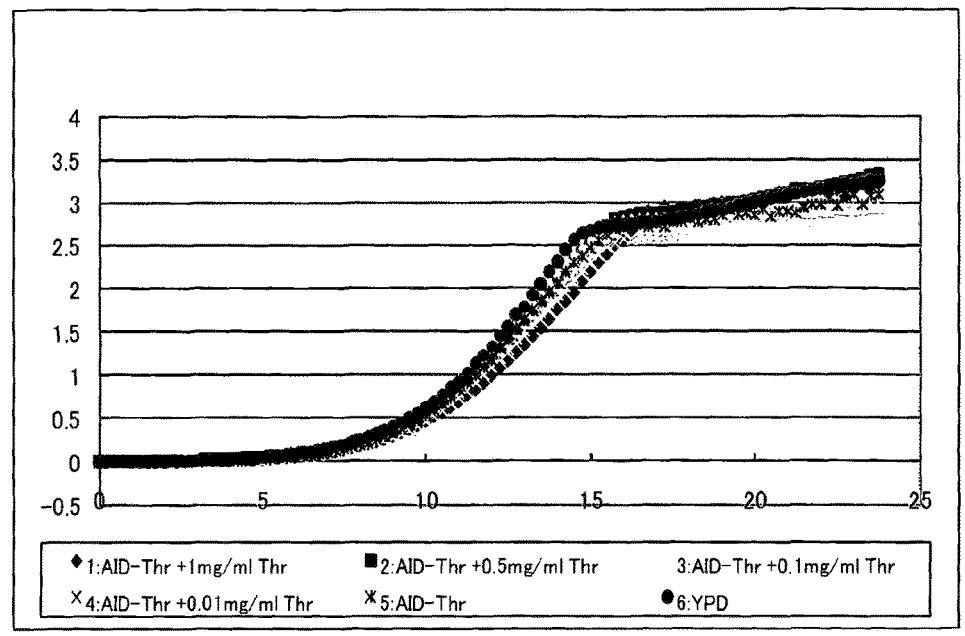
FIG. 36 illustrates proliferation of the RAK3599 strain due to differences in concentration of threonine contained in the AID culture medium.

Threonine concentration in the AID culture medium was adjusted to 0, 0.01, 0.1, 0.5, and 1 mg/mL, respectively, and proliferation of the RAK3599 strain was investigated. Results are shown in FIG. 36. Proliferation was confirmed to particularly increase at a threonine content of around 0.5 mg/mL. Given these results, a preferred threonine content was understood to be around 0.5 g/L.

(Asparagine)

Figure 37:
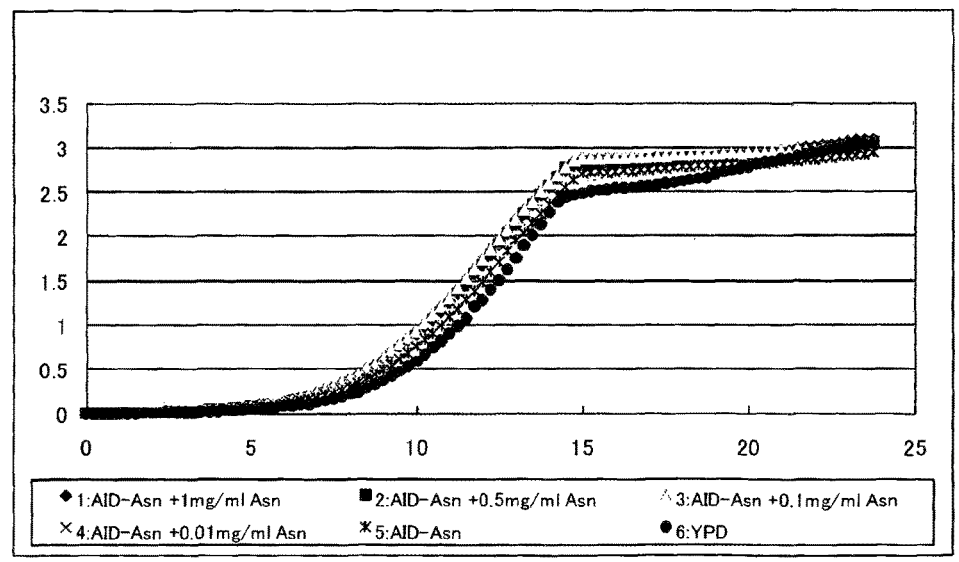
FIG. 37 illustrates proliferation of the RAK3599 strain due to differences in concentration of asparagine contained in the AID culture medium.

Asparagine concentration in the AID culture medium was adjusted to 0, 0.01, 0.1, 0.5, and 1 mg/mL, respectively, and proliferation of the RAK3599 strain was investigated. Results are shown in FIG. 37. Although not shown clearly in FIG. 37, $OD_{600}$ after 24 hours was 15, 16, 16, 17, and 16, respectively. Given these results, a preferred asparagine content was understood to be around 0.5 g/L.

(Investigation of Vitamin Concentration)

Figure 38:
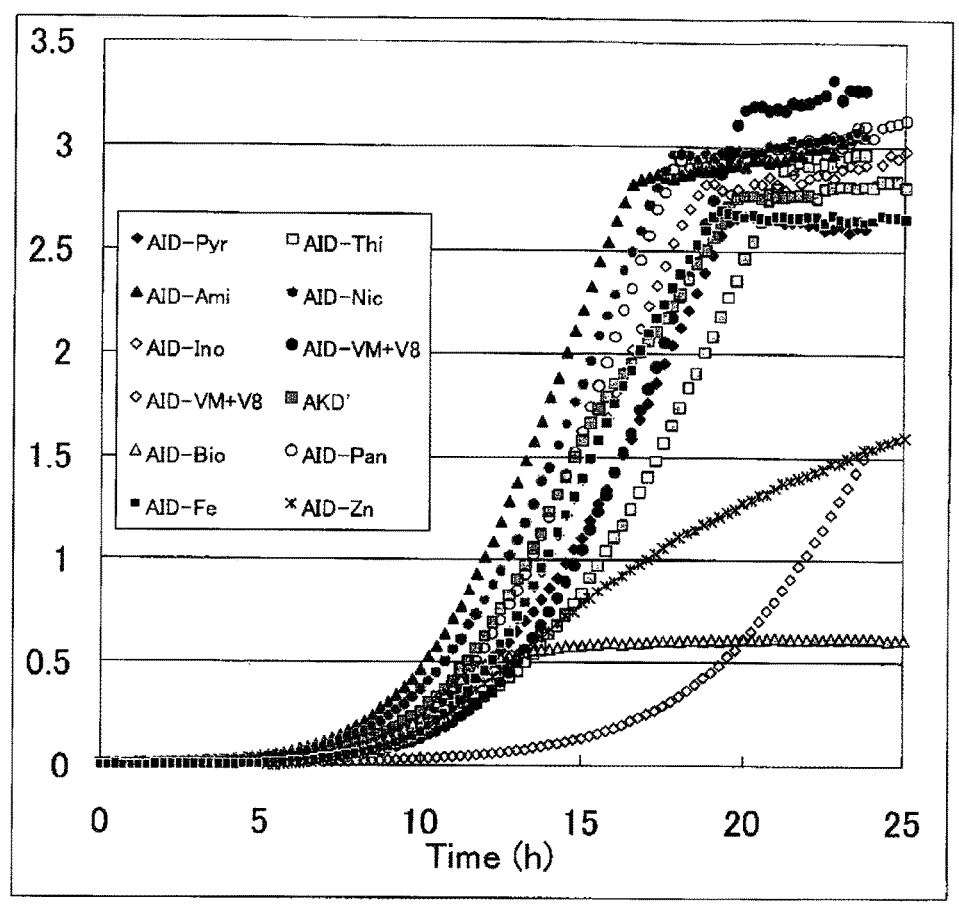
FIG. 38 illustrates an investigation of various kinds of vitamins and metallic ions contained in the AID culture medium.

An investigation was conducted into vitamins contained in the AID culture medium. Results are shown in FIG. 38. According to these results, para-aminobenzoic acid (represented by "Ami" in the drawings) was determined to have no effect to particularly increase proliferation.

(Substitution Potential of Pantothenic Acid)

Figure 39A:
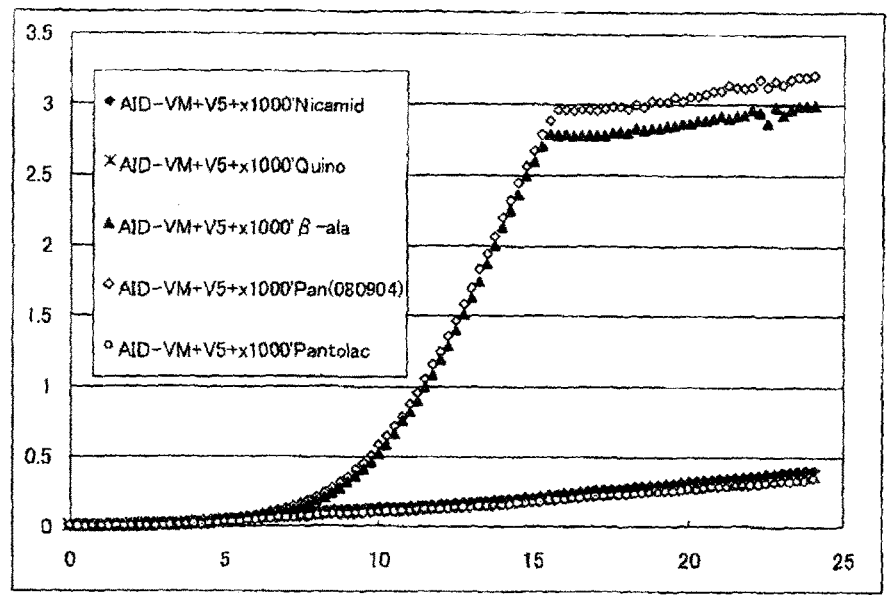
FIG. 39 illustrates (a) an investigation of substitution ability of pantothenic acid, and (b) proliferation of the RAK3599 strain due to differences in concentration of β-alanine.
Figure 39B:
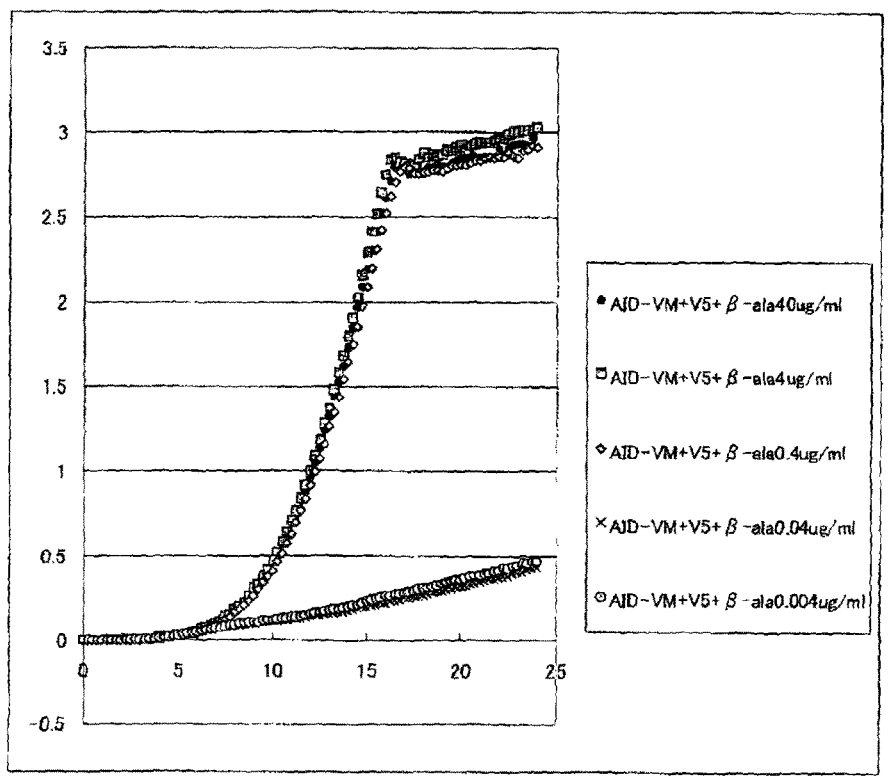

Next, substances capable of being substituted with pantothenic acid were investigated. Results are shown in FIG. 39A. β-alanine was confirmed to be substituted with pantothenic acid. Next, concentration of β-alanine was investigated. Results are shown in FIG. 39B. β-alanine was confirmed to be capable of substitution with pantothenic acid when 0.4 μg/mL or more β-alanine is added.

Embodiment 2

(Completion of AYD Culture Medium) (Culture Medium 3 of Present Invention)

Based on the investigation results of the AID culture medium and the aY-AID culture medium noted above, a formulation of a culture medium composition having still higher proliferation was prepared and named an AYD' culture medium (culture medium 2 of the present invention). An exemplary AYD' formulation is as follows.

TABLE 12

| Structural Component | Mfctr name | g/L | Structural Component | Mfctr name | g/L |
| --- | --- | --- | --- | --- | --- |
| Glucose | Katayama | 20.00 | Asparagine | Katayama 01-6780 Sigma A8381 | 0.50 |

TABLE 12-continued

| Structural Component | | Mfctr name | g/L | Structural Component | | Mfctr name | g/L | |
|---|---|---|---|---|---|---|---|---|
| KH$_2$PO$_4$ | | Sigma 24-5260-5 | 1.00 | Glutamine | | Katayama 12-0950-2 | 0.50 | |
| MgSO$_4$·7H$_2$O | | Katayama 19-0480 | 0.50 | Cysteine | hydrochloride monohydrate | Sigma 05-7470-2 | 0.50 | |
| Aspartic acid | Sodium salt monohydrate | Sigma A6683 | 5.00 | Leucine | | Katayama 18-1010-2 | 1.00 | |
| Arginine | monohydrochloride | Sigma A5131 | 10.00 | Tryptophan | | Sigma T0254 | 0.10 | |
| Lysine | monohydrochloride | Katayama 18-1900 | 1.00 | Histidine | monohydrochloride monohydrate | Sigma H8125 | 0.10 | |
| Proline | | Sigma P0380 | 1.00 | Adenine | hemisulfate salt | Sigma A9126 | 0.10 | |
| Glutamic acid | sodium salt hydrate | Sigma G1626 | 1.00 | Uracil | | Sigma U0750 | 0.10 | |
| Alanine | | Sigma A7627 | 1.00 | myo-Inositol | | Sigma 15-0510-2 | 1.00 | |
| Isoleucine | | Sigma I2752 | 1.00 | Pantothenic acid | Ca | Sigma P5710 | 4000 | μg |
| Phenylalanine | | Sigma P2126 | 1.00 | Nicotinic acid (Niacin) | | Sigma A1167 | 4000 | μg |
| Valine | | Sigma V0500 | 1.00 | Pyridoxine | hydrochloride | Wako 165-05401 | 400 | μg |
| Acetyl tyrosine | | Sigma A2513 | 1.00 | Thiamine | hydrochloride | Wako 203-00851 | 400 | μg |
| Methionine | | Sigma M9625 | 0.10 | Biotin | | Wako 023-08711 | 2 | μg |
| Serine | | Sigma S4500 | 0.50 | Ferric (III) chloride | anhydride | Wako 093-01672 | 4000 | μg |
| Threonine | | Sigma T8625 | 0.50 | Zinc sulfate | heptahydrate | Wako 261-01051 | 400 | μg |
| Glycine | | Katayama 12-1210 | 0.10 | | | | | |

(Glutamine, Cysteine)

Figure 40:
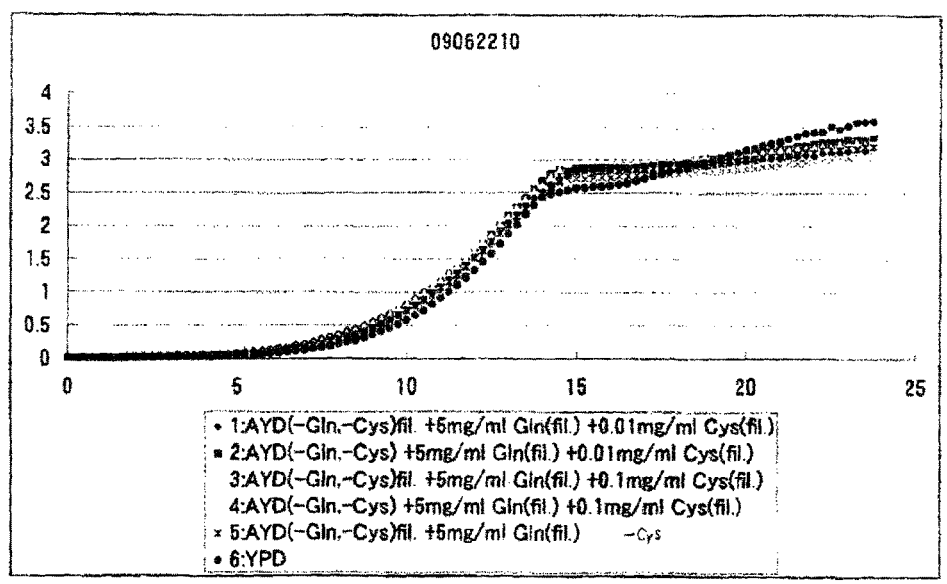
FIG. 40 illustrates proliferation of the RAK3599 strain due to differences in concentration of glutamine and cysteine contained in an AYD culture medium.

For the AYD' culture medium, an investigation was conducted into glutamine and cysteine concentrations using *Saccharomyces cerevisiae* RAK3599 strain. Results are shown in FIG. 40. In the process of trial-and-error, the glutamine concentration was set to 10 times the previous concentration, and growth was confirmed to be extremely improved. Therefore, a determination was made that glutamine at 5 g/L and cysteine at around 0.01 g/L was appropriate.

A culture medium for yeast having a high level of proliferation was achieved with the AYD culture medium (culture medium 3 of the present invention).

TABLE 13

| Structural Component | | Manufacturer Name | g/L | Structural Component | | Manufacturer Name | g/L | |
|---|---|---|---|---|---|---|---|---|
| Glucose | | Katayama | 20.00 | Asparagine | | Sigma A8381 | 0.50 | |
| KH$_2$PO$_4$ | | Katayama 24-5260-5 | 1.00 | Glutamine | | Katayama 12-0950-2 | 5.00 | |
| MgSO$_4$·7H$_2$O | | Katayama 19-0480 | 0.50 | Cysteine | hydrochloride monohydrate | Sigma 05-7470-2 | 0.01 | |
| Aspartic acid | Sodium salt monohydrate | Sigma A6683 | 5.00 | Leucine | | Katayama 18-1010-2 | 1.00 | |
| Arginine | monohydrochloride | Sigma A5131 | 10.00 | Tryptophan | | Sigma T0254 | 0.10 | |
| Lysine | monohydrochloride | Katayama 18-1900 | 1.00 | Histidine | monohydrochloride monohydrate | Sigma H8125 | 0.10 | |
| Proline | | Sigma P0380 | 1.00 | Adenine | hemisulfate salt | Sigma A9126 | 0.10 | |
| Glutamic acid | sodium salt hydrate | Sigma G1626 | 1.00 | Uracil | | Sigma U0750 | 0.10 | |
| Alanine | | Wako 014-01045 | 1.00 | myo-Inositol | | Sigma 15-0510-2 | 1.00 | |
| Isoleucine | | Sigma I2752 | 1.00 | Pantothenic acid | Ca | Sigma P5710 | 4000 | μg |
| Phenylalanine | | Sigma P2126 | 1.00 | Nicotinic acid (Niacin) | | Katayama SAJ 31-1460-2 | 4000 | μg |
| Valine | | Sigma V0500 | 1.00 | Pyridoxine | hydrochloride | Wako 165-05401 | 400 | μg |
| Acetyl tyrosine | | Sigma A2513 | 1.00 | Thiamine | hydrochloride | Wako 201-00852 | 400 | μg |

TABLE 13-continued

| Structural Component | Manufacturer Name | g/L | Structural Component | | Manufacturer Name | g/L |
|---|---|---|---|---|---|---|
| Methionine | Sigma M9625 | 0.10 | Biotin | | Sigma B4501 | 2 µg |
| Serine | Sigma S4500 | 0.50 | Ferric (III) chloride | anhydride | Wako 093-01672 | 4000 µg |
| Threonine | Sigma T8625 | 0.50 | Zinc sulfate | heptahydrate | Wako 261-01051 | 400 µg |
| Glycine | Katayama 12-1210 | 0.10 | | | | |

TABLE 14

| Culture medium composition | Abbrev. | | g/L AYD/L | |
|---|---|---|---|---|
| Glucose | Glc | Katayama | 20.00 | |
| Arginine | Arg | Sigma A5131 | 10.00 | AY7 |
| Aspartic acid | Asp | Sigma A6683 | 5.00 | |
| Glutamine | Gln | Katayama SAJ 12-0950-2 | 5.00 | |
| Alanine | Ala | Wako 014-01045 | 1.00 | |
| Glutamic acid | Glu | Sigma G1626 | 1.00 | |
| Proline | Pro | Sigma P0380 | 1.00 | |
| Asparagine | Asn | Sigma A8381 monohydrate | 0.50 | |
| Leucine | Leu | Katayama SAJ 18-1010-2 | 1.00 | ILV |
| Isoleucine | Ile | Sigma I2752 | 1.00 | |
| Valine | Val | Sigma V0500 | 1.00 | |
| Phenylalanine | Phe | Sigma P2126 | 1.00 | AY3 |
| N-acetyltyrosine | AcTyr | Sigma A2513 | 1.00 | |
| Tryptophan | Trp | Sigma T0254 | 0.10 | |
| Serine | Ser | Sigma S4500 | 0.50 | AY5 |
| Threonine | Thr | Sigma T8625 | 0.50 | |
| Glycine | Gly | Katayama 12-1210 | 0.10 | |
| Methionine | Met | Sigma M9625 | 0.10 | |
| Cysteine | Cys | Sigma 05-7470-2 | 0.01 | |
| Lysine | Lys | Katayama 18-1900 | 1.00 | AY4 |
| Histidine | His | Sigma H8125 | 0.10 | |
| Adenine | Ade | Sigma A9126 | 0.10 | |
| Uracil | Ura | Sigma U0750 | 0.10 | |
| $KH_2PO_4$ | KPO4 | Katayama 24-5260-5 | 1.00 | KIM |
| myo-Inositol | Ino | Sigma 15-0510-2 | 1.00 | |
| $MgSO_4 \cdot 7H_2O$ | Mg | Katayama 19-0480 | 0.50 | |
| Pantothenic acid | Pan | Sigma P5710 | 4 mg | |
| Pyridoxine | Pyr | Wako 163-05402 | 0.4 mg | Vitamin filtration ×1000 after |
| Thiamine | Thi | Wako 201-00852 | 0.4 mg | |
| Zinc sulfate | Zn | Wako 261-01051 | 0.4 mg | |
| Biotin | Bio | Sigma B4501 | 2 µg | |
| Ferric (III) chloride | Fe | Wako 093-01672 | 4 mg | |
| Nicotinc acid (Niacin) | Nic | Katayama SAJ 31-1430-2 | 4 mg | |

(Combination Effects of Amino Acids)

Figure 41A:
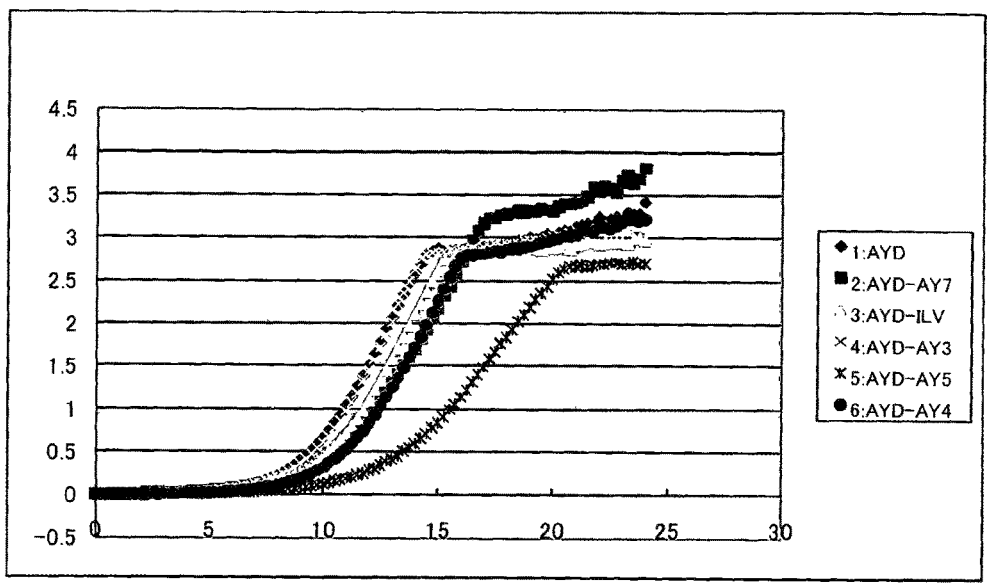
FIG. 41 illustrates an investigation of combination effects of amino acids. The amino acids are divided into five groups, and each group is eliminated from the culture medium and an effect confirmed, results of which are shown in FIG. 41(a).
FIG. 41(b) illustrates results of an investigation into an individual amino acid component of AY5 groups for which a significant decrease in proliferation was confirmed.
Figure 41B:
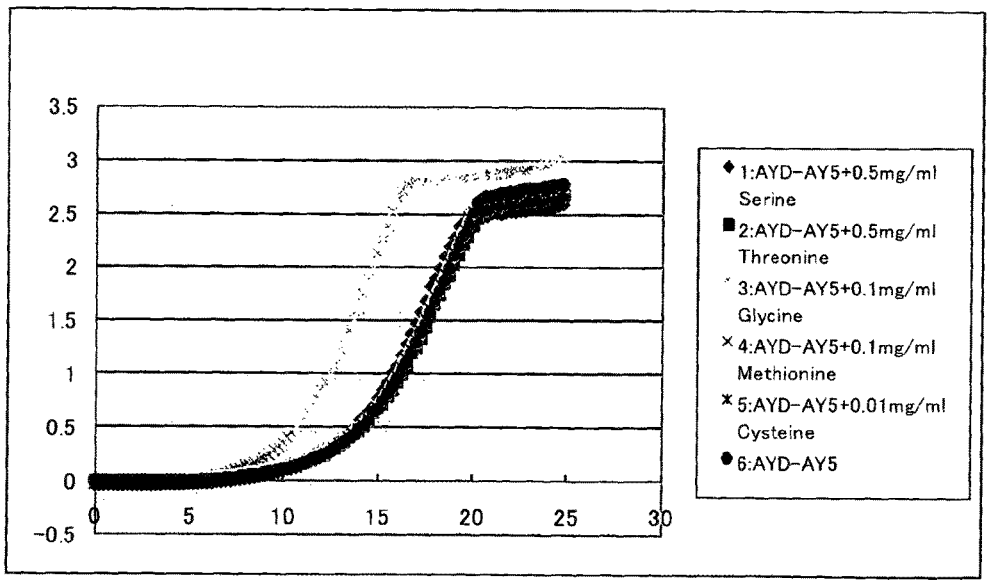

In the AYD culture medium, using the *Saccharomyces cerevisiae* RAK3599 strain, the amino acids are divided into five groups as shown in Table 14 above, and each group is eliminated from the culture medium to confirm any effect. Results are shown in FIG. 41A. In a culture medium (AYD-AY5) in which a group of serine, threonine, glycine, methionine, and cysteine are eliminated, a marked decrease in proliferation was confirmed. Therefore, individual amino acid components of the AY5 group were investigated. Results are shown in FIG. 41B. From these results, it was understood that when methionine is deficient, proliferation decreases. This result does not match results of an investigation of independent addition of methionine in the AID culture medium. As shown in Table 2 above, in a case where methionine was added independently to the AID culture medium as the amino acid, there was almost no proliferation of yeast, and no positive effect on proliferation was confirmed even when methionine was added at a high concentration. In addition, when a glutamine concentration in the AYD' culture medium was set to 5 g/L, growth was confirmed to improve further. Given this, an amino acid's effect on proliferation of yeast in a case of combination of multiple amino acids does not necessarily match that in a case of independent use of the amino acid.

(Comparison with YPD Culture Medium)

Figure 42:
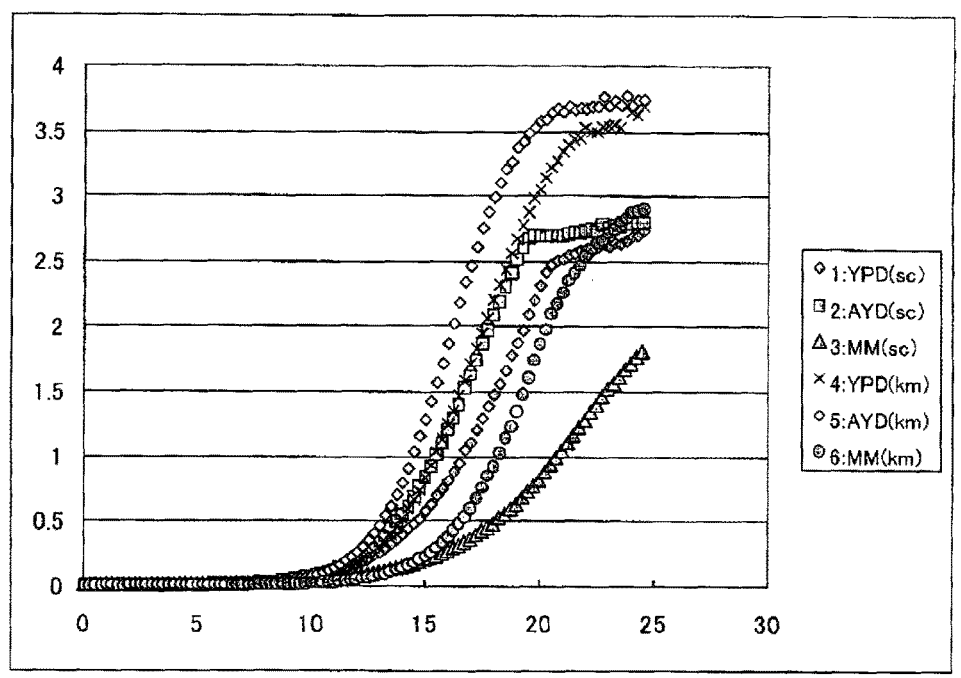
FIG. 42 compares the AYD culture medium with the YPD culture medium and an MM culture medium using a *Kluyveromyces* DMKU3-1042 strain and *Saccharomyces*.
Figure 43A:
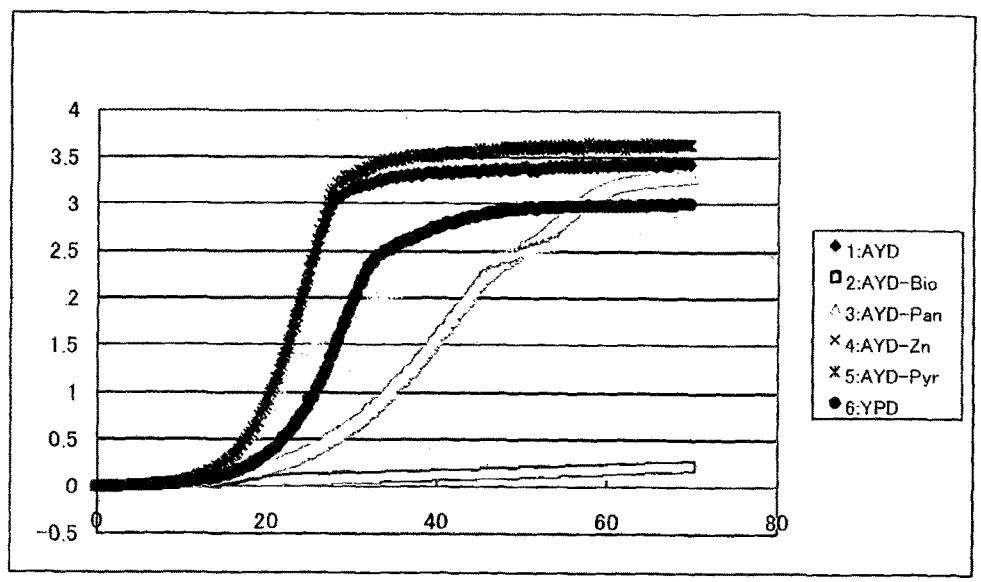
FIG. 43 investigates nutritional requirements of a *Schizosaccharomyces pombe* FY7507 strain. In (a), biotin, pantothenic acid, zinc, and pyridoxine are investigated, while in (b), thiamine, iron, and nicotinic acid (niacin) are investigated.
Figure 43B:
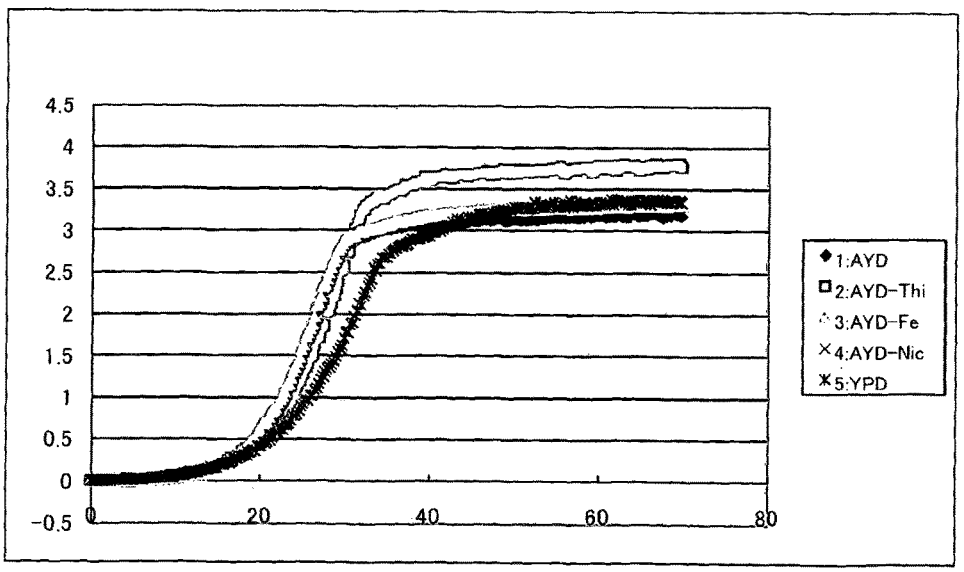
Figure 44A:
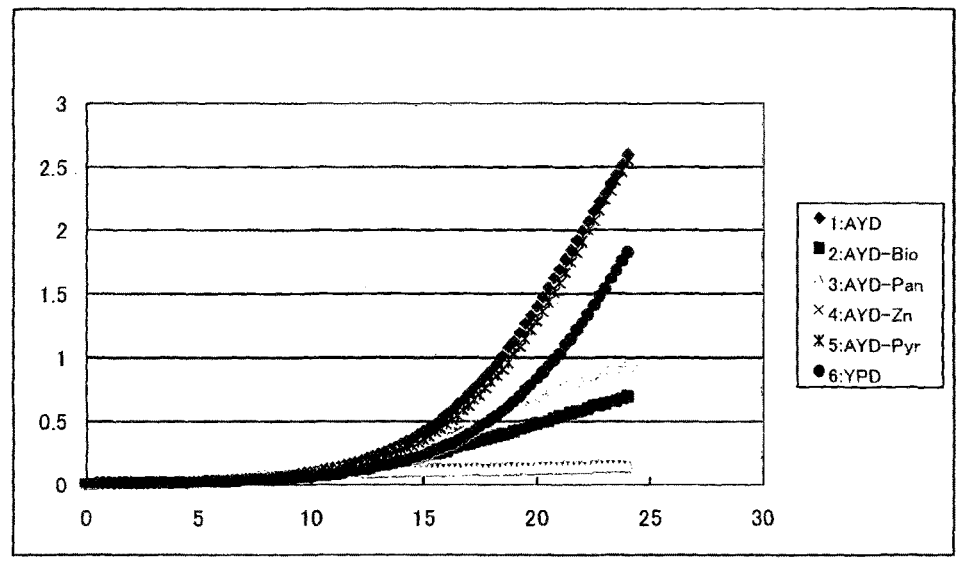
FIG. 44 investigates nutritional requirements of a *Schizosaccharomyces* RAK5576 strain. In (a), biotin, pantothenic acid, zinc, and pyridoxine are investigated, while in (b), thiamine, iron, and nicotinic acid (niacin) are investigated.
Figure 44B:
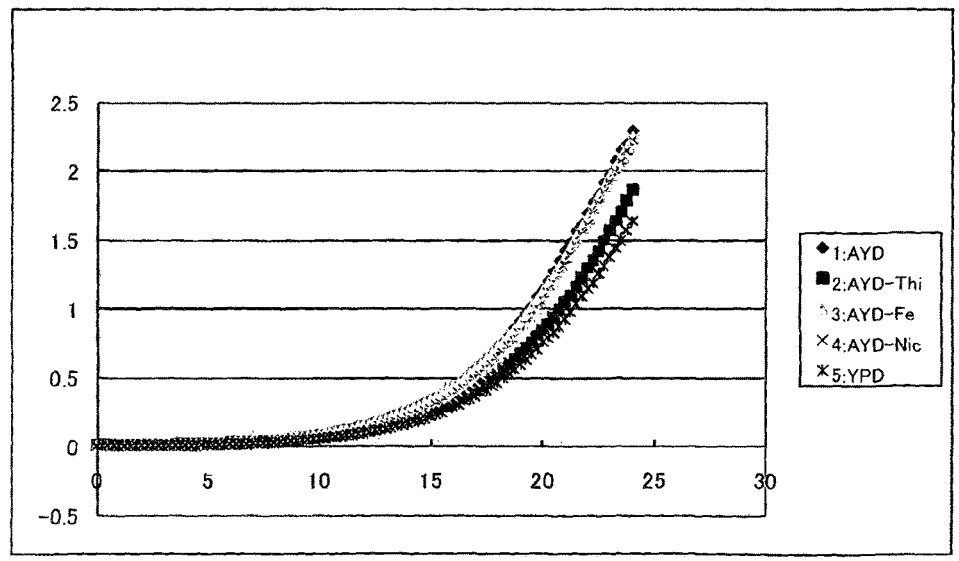
Figure 45A:
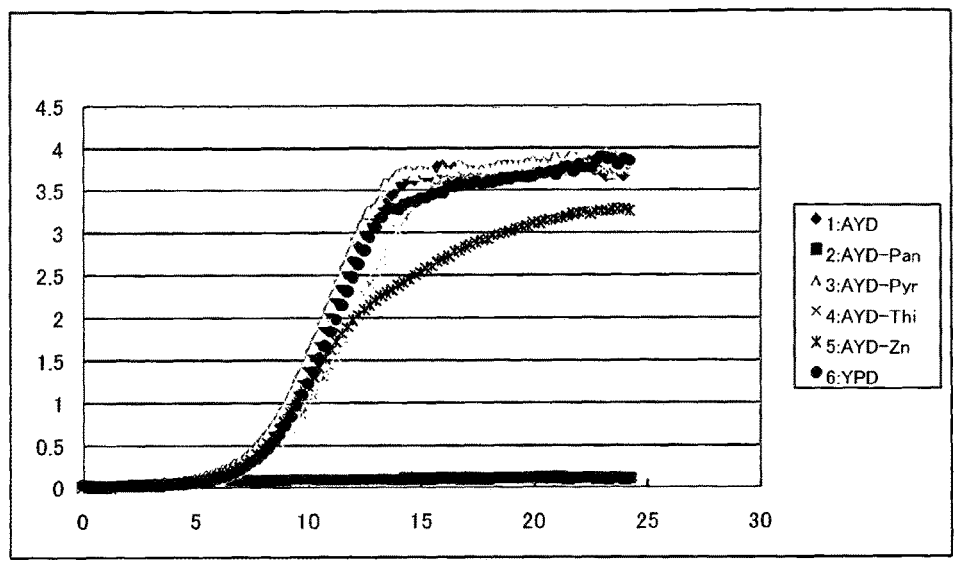
FIG. 45 illustrates nutritional requirements of a *Kluyveromyces marxianus* NCYC587 strain. In (a), pantothenic acid, pyridoxine, thiamine, and zinc are investigated, while in (b), biotin, iron, and nicotinic acid (niacin) are investigated.
Figure 45B:
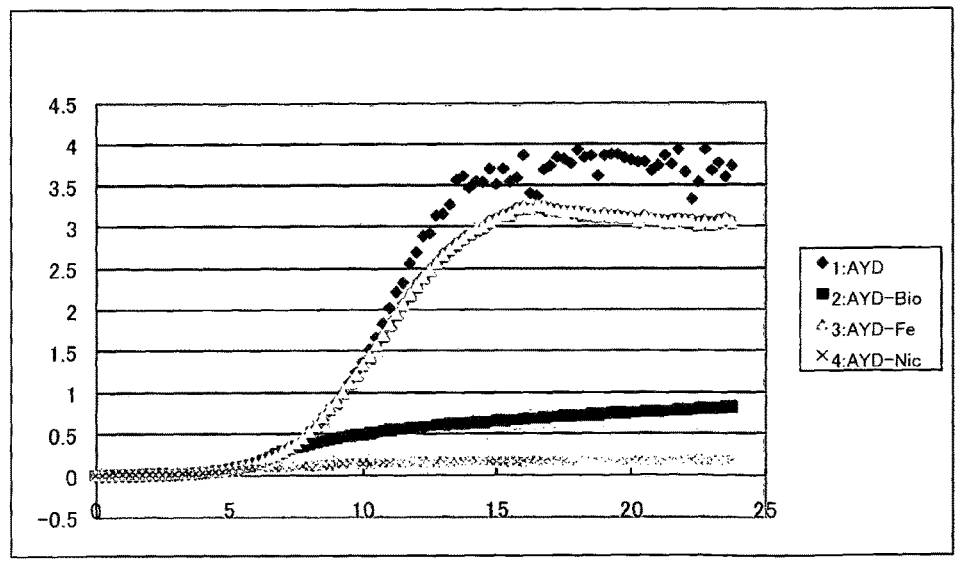
Figure 46A:
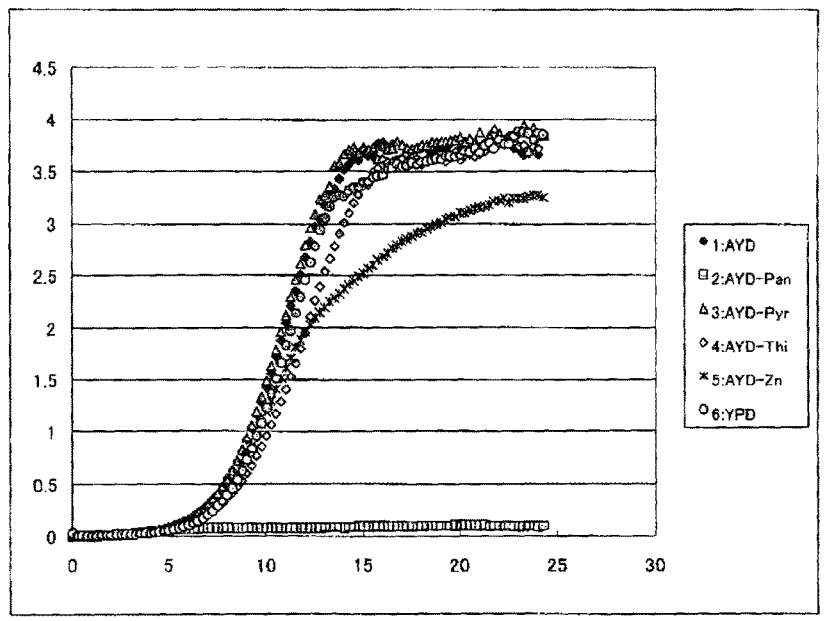
FIG. 46 illustrates nutritional requirements of a *Kluyveromyces marxianus* NCYC1429 strain. In (a), pantothenic acid, pyridoxine, thiamine, and zinc are investigated, while in (b), biotin, iron, and nicotinic acid (niacin) are investigated.
Figure 46B:
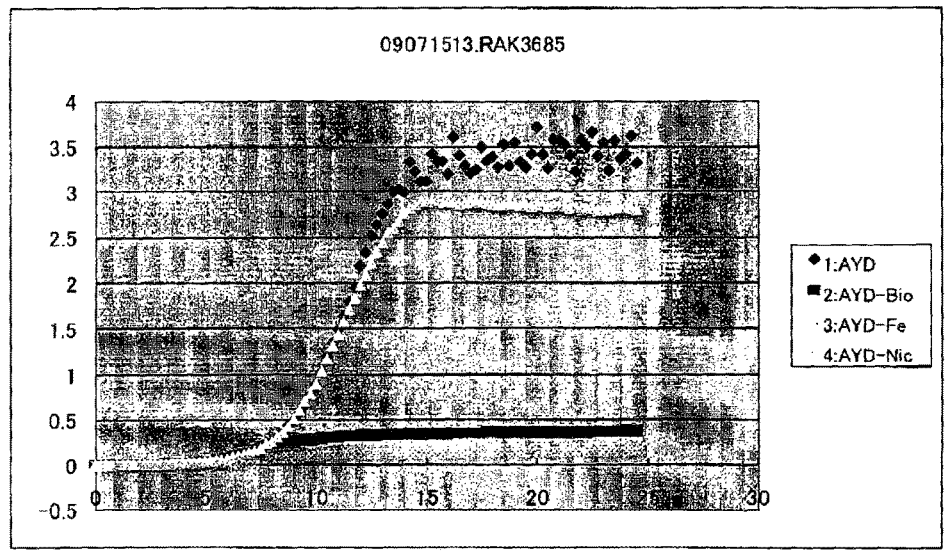
Figure 47A:
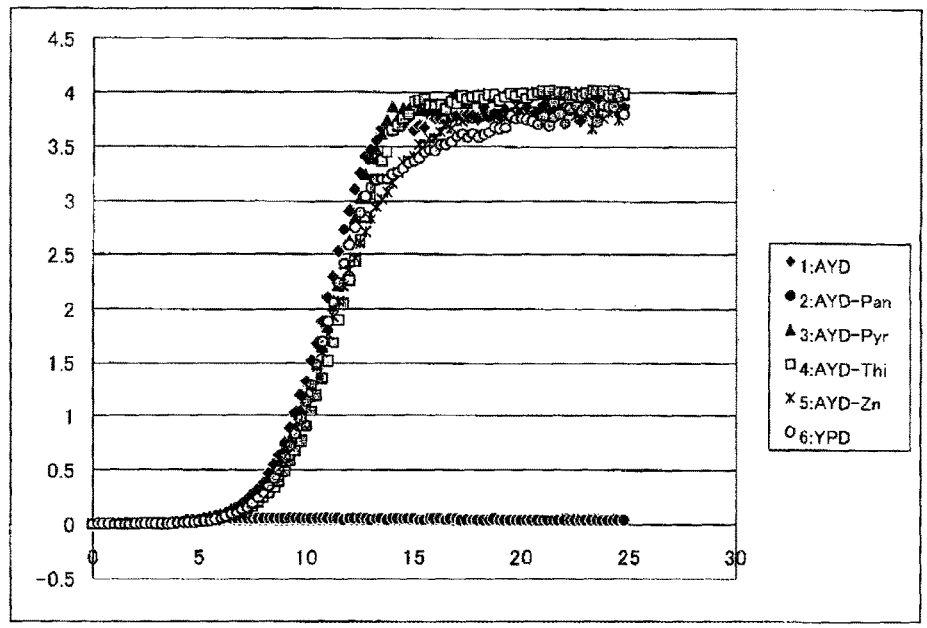
FIG. 47 illustrates nutritional requirements of a *Kluyveromyces marxianus* NCYC2791 strain. In (a), pantothenic acid, pyridoxine, thiamine, and zinc are investigated, while in (b), biotin, iron, and nicotinic acid (niacin) are investigated.
Figure 47B:
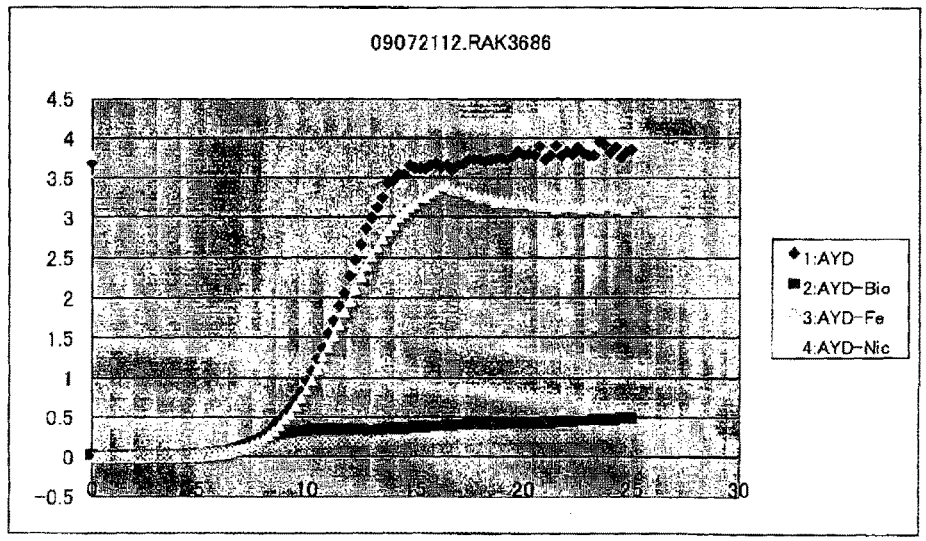
Figure 48A:
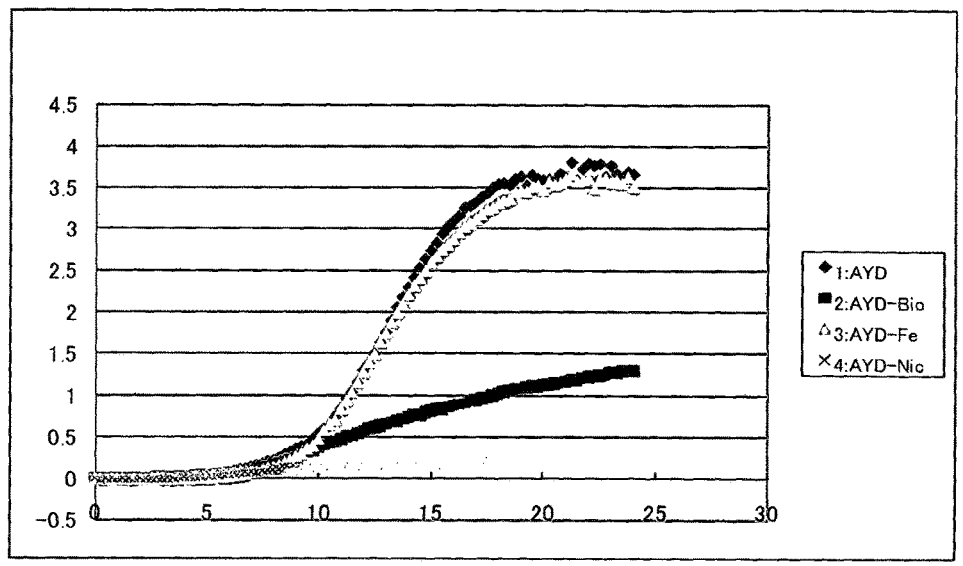
FIG. 48 illustrates nutritional requirements of a *Kluyveromyces lactis* NRRLY-1140 strain. In (a), biotin, iron, and nicotinic acid (niacin) are investigated, while in (b), pantothenic acid, pyridoxine, thiamine, and zinc are investigated.
Figure 48B:
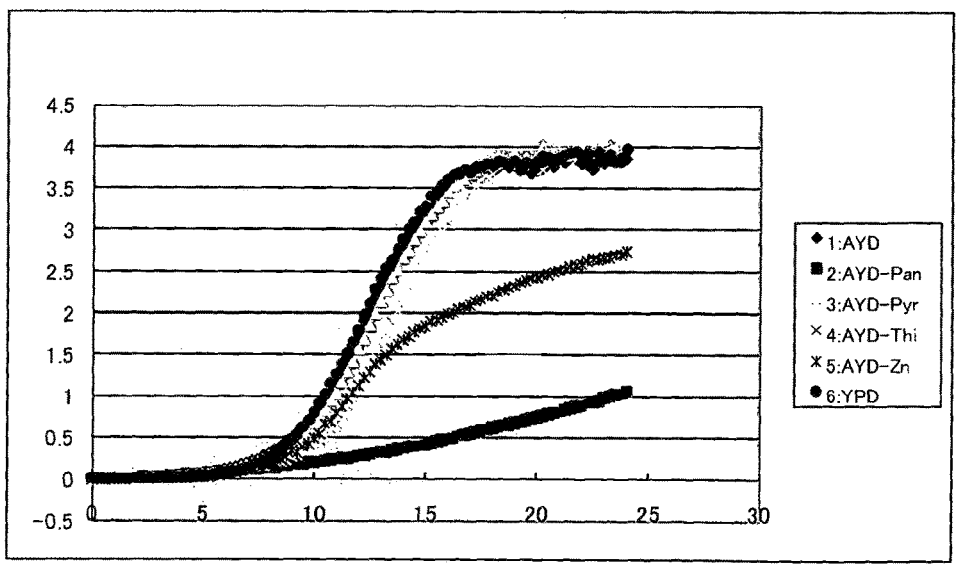
Figure 49A:
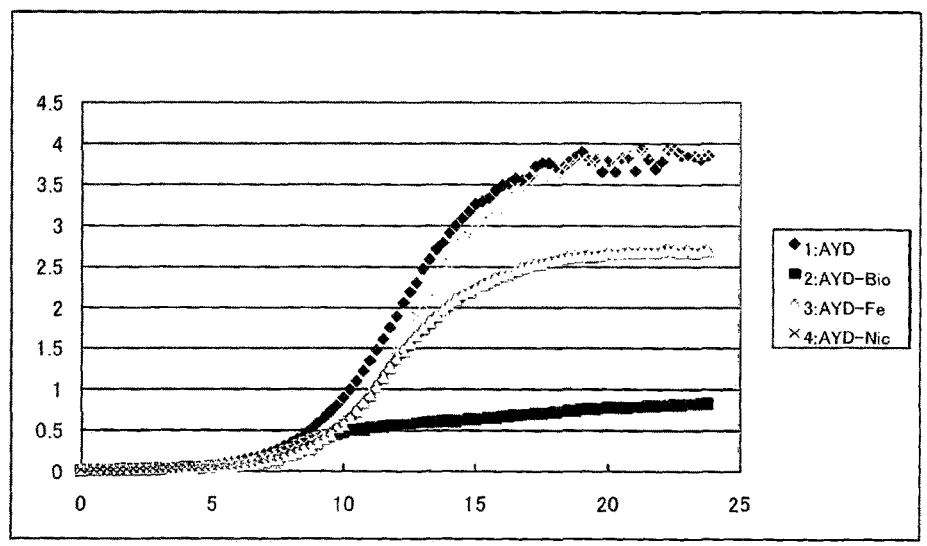
FIG. 49 illustrates nutritional requirements of a *Pichia stipitis* NBRC10063 strain. In (a), biotin, iron, and nicotinic acid (niacin) are investigated, while in (b), pantothenic acid, pyridoxine, thiamine, and zinc are investigated.
Figure 49B:
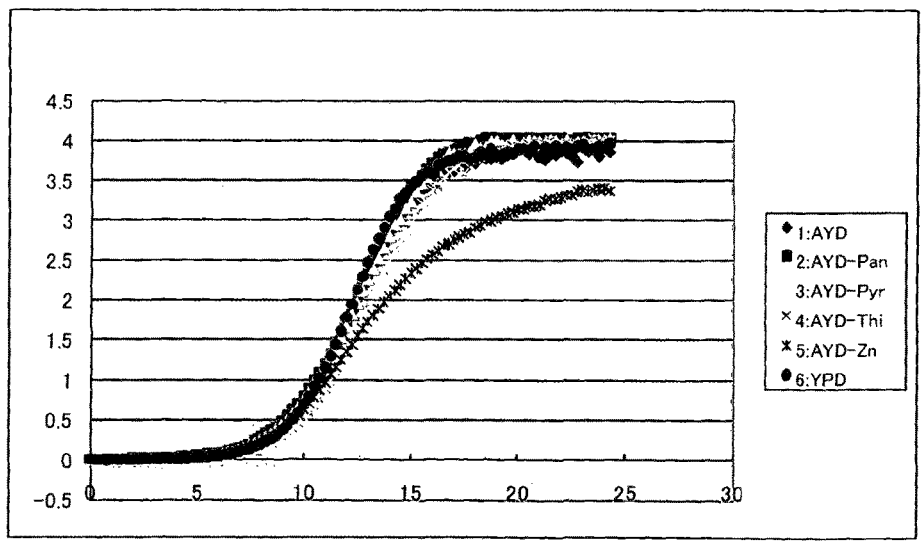
Figure 50A:
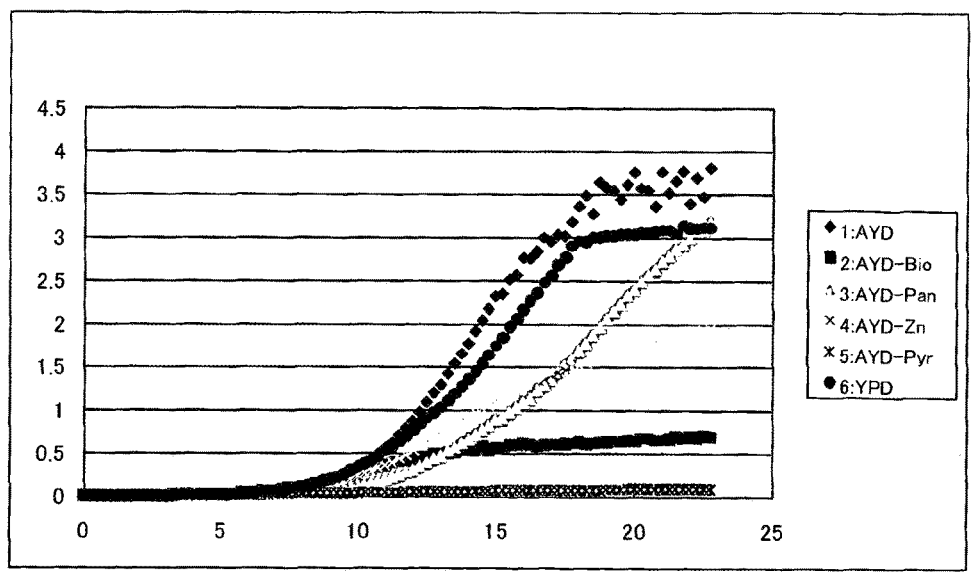
FIG. 50 illustrates nutritional requirements of a *Candida glabrata* BY23876 strain. In (a), biotin, pantothenic acid, zinc, and pyridoxine are investigated, while in (b), thiamine, iron, and nicotinic acid (niacin) are investigated.
Figure 50B:
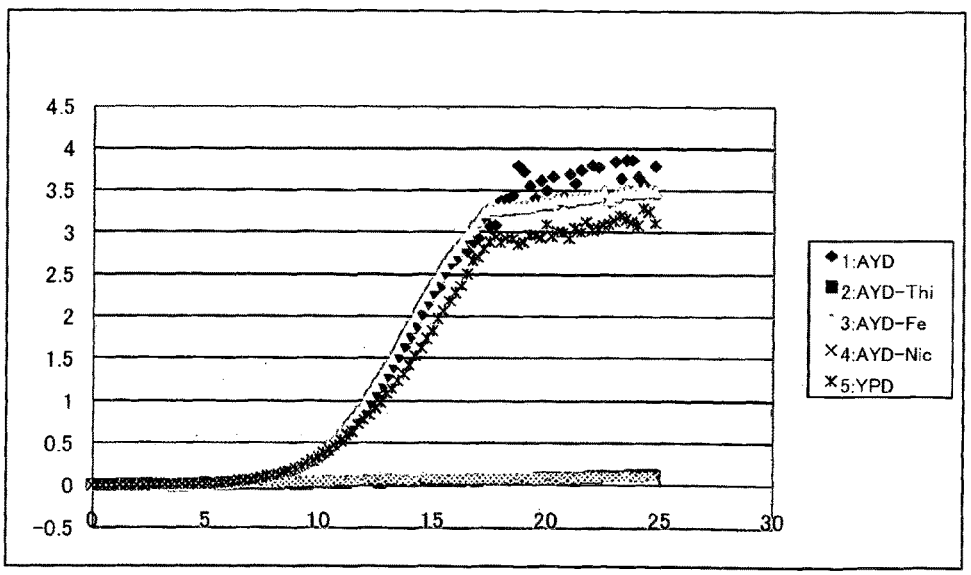
Figure 51A:
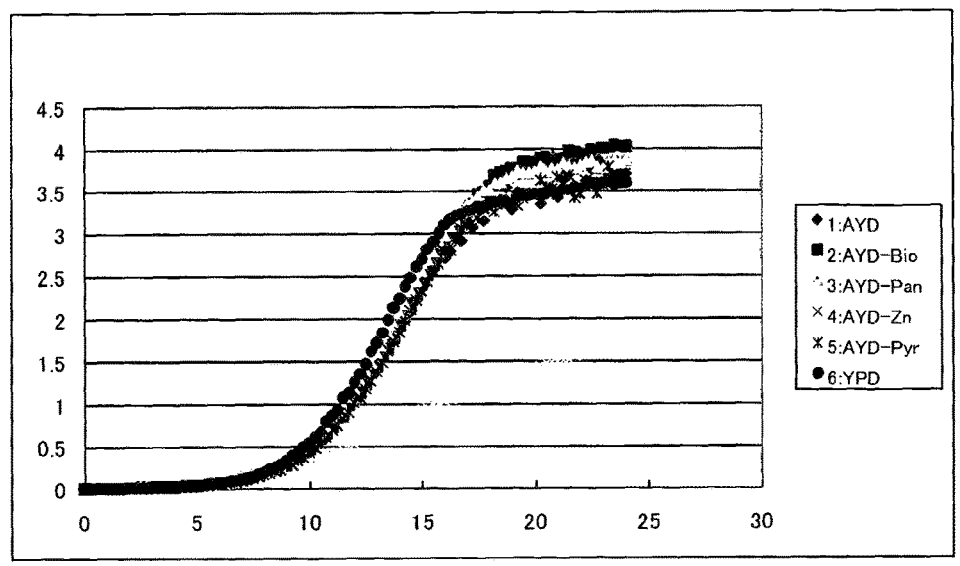
FIG. 51 illustrates nutritional requirements of a *Candida utilis* JCM9624 strain. In (a), biotin, pantothenic acid, zinc, and pyridoxine are investigated, while in (b), thiamine, iron, and nicotinic acid (niacin) are investigated.
Figure 51B:
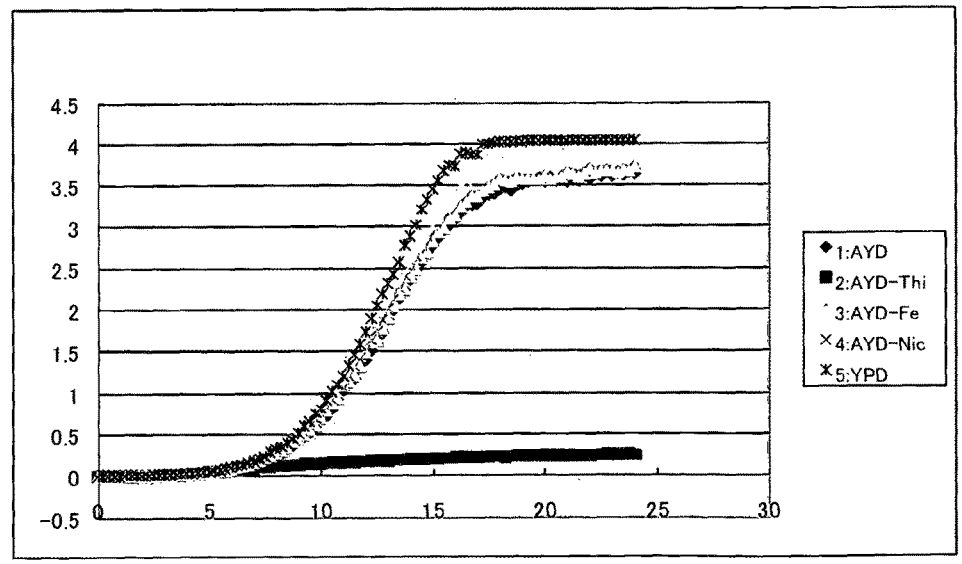
Figure 52A:
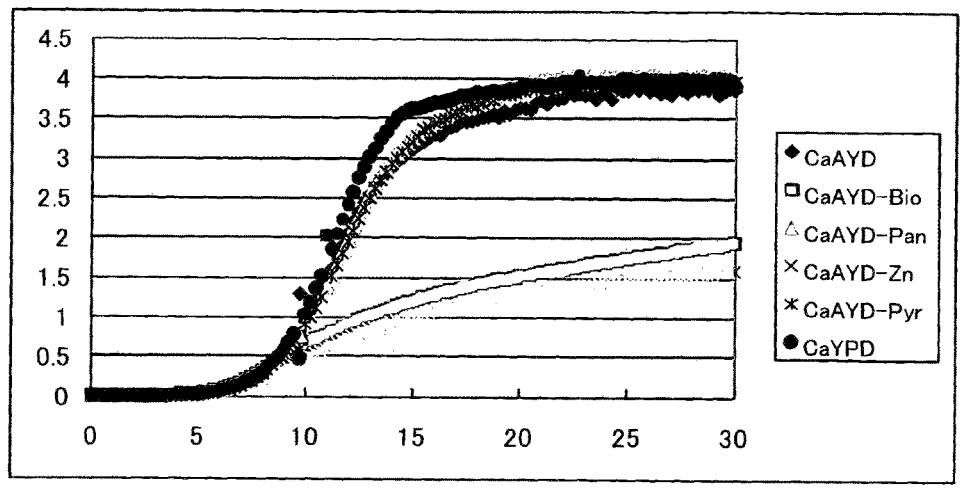
FIG. 52 illustrates nutritional requirements of a *Candida albicans* JCM1542 strain. In (a), biotin, pantothenic acid, zinc, and pyridoxine are investigated, while in (b), thiamine, iron, and nicotinic acid (niacin) are investigated.
Figure 52B:
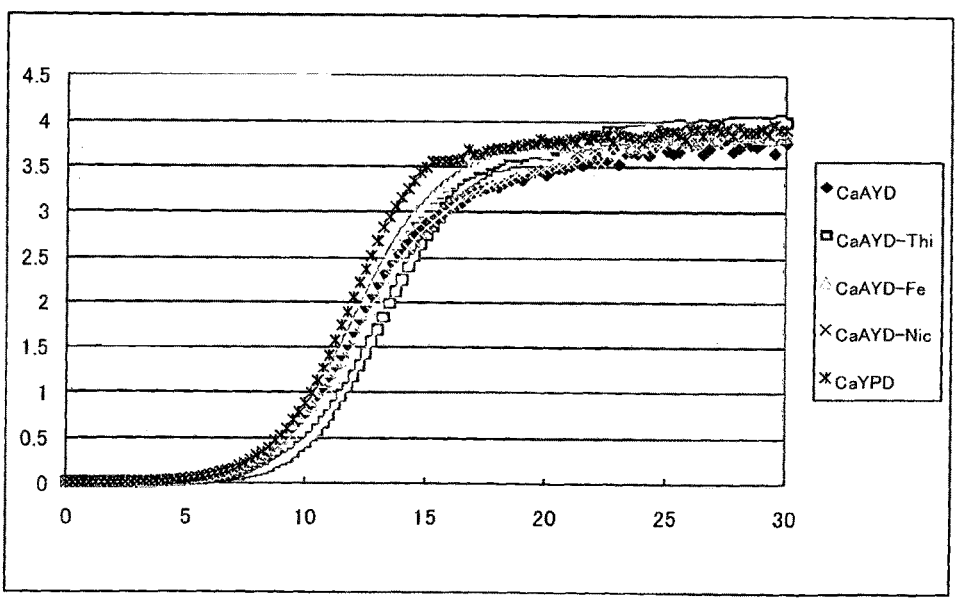

A comparison of the AYD culture medium, YPD culture medium, and MM culture medium was conducted. Results are shown in FIG. 42. The AYD culture medium exhibited proliferation extremely close to that of the YPD culture medium for both *Kluyveromyces* and *Saccharomyces*. *Kluyveromyces* exhibited a greater proliferation than *Saccharomyces*; however, the proliferation of both in the AYD culture medium was greater than that in the YPD culture medium, and a positive effect of the culture medium according to the present invention was confirmed.

(Investigation of Nutrient-requiring Strains)

Nutritional requirements of each of the following yeast strains were investigated in the AYD culture medium, and utility of the AYD culture medium was confirmed. Each of the yeast strains was cultured under identical conditions using the basic culture method described above. Results are shown in FIGS. 43 to 52.

Data is shown for when *Schizosaccharomyces pombe* FY7507 strain is cultivated for 70 hours. Although not clearly shown in FIG. 43, $OD_{600}$ after 72 hours for the AYD culture medium, biotin-deficient AYD culture medium, pantothenic acid-deficient AYD culture medium, $Zn^{2+}$-deficient AYD culture medium, pyridoxine-deficient AYD culture medium, thiamine-deficient AYD culture medium, Fe3+-deficient AYD culture medium, niacin-deficient AYD culture medium, and YPD culture medium was between 18 and 20; 1; 15; 8; 19; 19; 17; 2; and between 15 and 17, respectively. The *Schizosaccharomyces pombe* FY7507 strain was confirmed to require biotin and to require nicotinic acid. Including Zn2+ was also confirmed as preferable for proliferation of this strain (see FIGS. 43A and 43B).

Data is shown for when *Zygosaccharomyces* RAK5576 strain is cultivated for 24 hours. Although not clearly shown in FIG. 44, $OD_{600}$ after 24 hours for the AYD culture medium, biotin-deficient AYD culture medium, pantothenic acid-deficient AYD culture medium, $Zn^{2+}$-deficient AYD culture medium, pyridoxine-deficient AYD culture medium, thiamine-deficient AYD culture medium, $Fe^{3+}$-deficient AYD culture medium, niacin-deficient AYD culture medium, and YPD culture medium was between 8 and 10; 2; 1; 2; 8; 6; 5; 9; and between 5 and 6, respectively. The *Zygosaccharomyces* RAK5576 strain was confirmed to require biotin and to require pantothenic acid. Including $Zn^{2+}$ was also confirmed as preferable for proliferation of this strain (see FIGS. 44A and 44B).

Data is shown for when *Kluyveromyces marxianus* NCYC587 (RAK3684) strain, NCYC1429 (RAK3685) strain, and NCYC2791 (RAK3686) strain are each cultivated for 24 hours. Although not clearly shown in FIGS. 45 to 47, $OD_{600}$ after 24 hours for the AYD culture medium, biotin-deficient AYD culture medium, pantothenic acid-deficient AYD culture medium, $Zn^{2+}$-deficient AYD culture medium, pyridoxine-deficient AYD culture medium, thiamine-deficient AYD culture medium, $Fe^{3+}$-deficient AYD culture medium, niacin-deficient AYD culture medium, and YPD culture medium was between 35 and 37; between 2 and 7; between 0 and 4; between 12 and 29; between 34 and 45; between 26 and 50; between 13 and 35; between 1 and 6; and between 34 and 44, respectively. These strains were confirmed to require biotin, to require niacin, and also to require pantothenic acid. Proliferation of these strains was also confirmed to require $Zn^{2+}$ (see FIGS. 45A and 45B, FIGS. 46A and 46B, and FIGS. 47A and 47B).

Similarly, data is shown for when *Kluyveromyces lactis* NRRLY-1140 strain is cultivated for 24 hours. Although not clearly shown in FIG. 48, $OD_{600}$ after 24 hours for the AYD culture medium, biotin-deficient AYD culture medium, $Fe^{3+}$-deficient AYD culture medium, niacin-deficient AYD culture medium, pantothenic acid-deficient AYD culture medium, pyridoxine-deficient AYD culture medium, thiamine-deficient AYD culture medium, $Zn^{2+}$-deficient AYD culture medium, and YPD culture medium was between 28 and 30; 1; 18; 1; 0; 27; 29; 6; and 45, respectively. *Kluyveromyces lactis* was confirmed to require biotin, to require niacin, and also to require pantothenic acid. Proliferation of these strains was also confirmed to require $Zn^{2+}$ (see FIGS. 48A and 48B).

Data is shown for when *Pichia stipitis* NBRC10063 (RAK5128) strain is cultivated for 24 hours. Although not clearly shown in FIG. 49, $OD_{600}$ after 24 hours for the AYD culture medium, biotin-deficient AYD culture medium, $Fe^{3+}$-deficient AYD culture medium, niacin-deficient AYD culture medium, pantothenic acid-deficient AYD culture medium, pyridoxine-deficient AYD culture medium, thiamine-deficient AYD culture medium, $Zn^{2+}$-deficient AYD culture medium, and YPD culture medium was between 35 and 38; 4; 12; 40; 34; 38; 35; 22; and 58, respectively. *Pichia stipitis* was confirmed to require biotin, but did not require pantothenic acid. Including $Zn^{2+}$ and an iron ion was also confirmed as preferable for proliferation of this strain (see FIGS. 49A and 49B).

*Candida glabrata* BY23876 strain was confirmed to require biotin, and to require pyridoxine, thiamine, and nicotinic acid (see FIGS. 50A and 50B). *Candida utilis* JCM9624 strain was confirmed to not require biotin, but to require thiamine. Including a Zn ion was also confirmed as preferable for proliferation of this strain (see FIGS. 51A and 51B). *Candida albicans* JCM1542 strain was confirmed to require biotin. Including Zn2+ was also confirmed as preferable for proliferation of this strain (see FIGS. 52A and 52B).

INDUSTRIAL APPLICABILITY

Figure 53A:
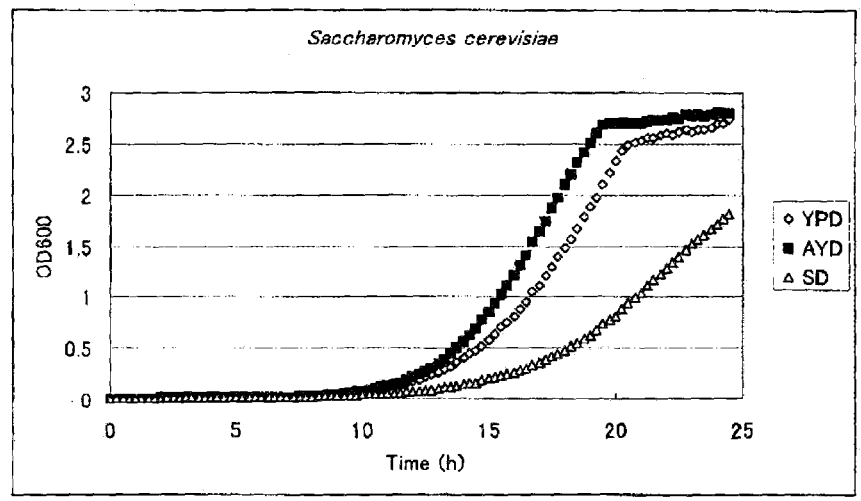
FIG. 53 illustrates, in (a) and (b), results of comparing proliferation after cultivating *Saccharomyces cerevisiae* and *Kluyveromyces marxianus* using the SD culture medium, the YPD culture medium, and a culture medium according to the present invention.
Figure 53B:
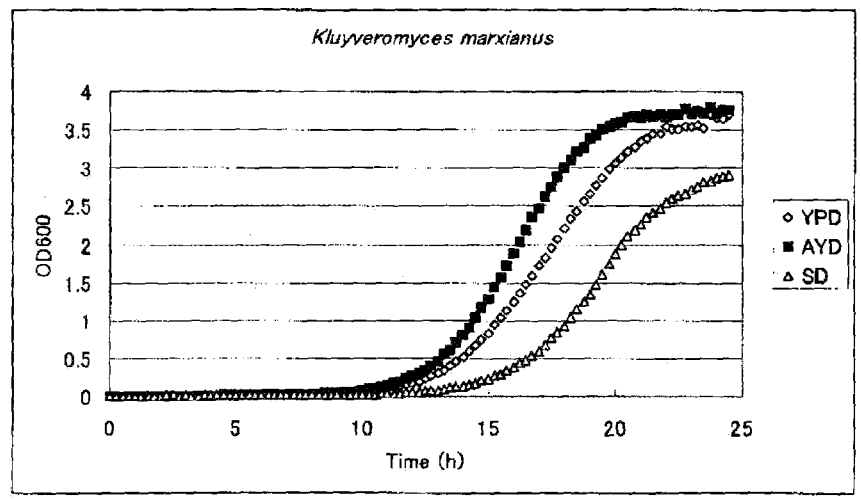

*Saccharomyces cerevisiae* and *Kluyveromyces marxianus* were cultivated using a culture medium according to the present invention, as well as an SD culture medium and a YPD culture medium, which are widely-used conventional synthetic culture mediums for yeast, and a comparison was conducted of proliferation. Results are shown in FIGS. 53A and 53B. The culture medium according to the present invention exhibited proliferation close or equivalent to a eutrophic culture medium and, due to a positive effect of the culture medium according to the present invention, the present invention can be said to provide a culture medium that is useful in fermentation industries and the like.

The invention claimed is:
1. A yeast culture medium comprising:
   a) a sugar capable of being assimilated by yeast;
   b) an amino acid comprising aspartic acid, acetyl tyrosine, or proline;
   c) vitamins;
   d) inositol;
   e) zinc ions ($Zn^{2+}$);
   f) potassium ions ($K^+$), and
   g) magnesium ions ($Mg^{2+}$), and
   wherein:
      the amount of sugar is between 1 g/L and 200 g/L;
      the amount of aspartic acid is between 0.1 g/L and 10 g/L, when selected;
      the amount of proline is between 0.1 g/L and 5 g/L, when selected;
      the amount of acetyl tyrosine is between 0.1 g/L and 5 g/L, when selected;
      the amount of zinc ions is between 0.405 µg/L and 2024.9 µg/L;
      the amount of potassium ions is between 0.0287 g/L and 2.87 g/L;
      the amount of magnesium ions is between 0.986 mg/L and 493 mg/L; and
      the amount of inositol is between 50 mg/L and 10,000 mg/L.
2. The yeast culture medium according to claim 1 further comprising adenine, uracil, guanine, cytosine, or thymine.
3. The yeast culture medium according to claim 1 further comprising at least two amino acids selected from arginine, lysine, proline, glutamic acid, alanine, isoleucine, phenyl- alanine, valine, methionine, serine, threonine, glycine, asparagine, glutamine, cysteine, leucine, tryptophan, and histidine.

4. The yeast culture medium according to claim 1, wherein ammonium ions are not present in the medium.

5. The yeast culture medium according to claim 1, wherein the vitamins comprise at least two selected from biotin, pantothenic acid, niacin, pyridoxine, and thiamine.

6. The yeast culture medium according to claim 1, wherein the sugar comprises glucose, lactose, mannose, fructose, sucrose, maltose, or raffinose.

7. The yeast culture medium according to claim 1, wherein yeast extract is not present in the medium.

8. The yeast culture medium according to claim 1, wherein the vitamins comprises between 0.02 µg/L and 10 µg/L of biotin.

9. A yeast culture medium comprising the following the concentrations of structural components

TABLE 1

| Structural Component | Concentration | Structural Component | Concentration |
|---|---|---|---|
| Glucose | 20 g/L | Asparagine | 0.5 g/L |
| $KH_2PO_4$ | 1 g/L | Glutamine | 5 g/L |
| $MgSO_4 \cdot 7H_2O$ | 0.5 g/L | Cysteine | 0.01 g/L |
| Aspartic acid | 5 g/L | Leucine | 1 g/L |
| Arginine | 10 g/L | Tryptophan | 0.1 g/L |
| Lysine | 1 g/L | Histidine | 0.1 g/L |
| Proline | 1 g/L | Adenine | 0.1 g/L |
| Glutamic acid | 1 g/L | Uracil | 0.1 g/L |
| Alanine | 1 g/L | myo-Inositol | 1 g/L |
| Isoleucine | 1 g/L | Pantothenic acid | 4000 µg/L |
| Phenylalanine | 1 g/L | Nicotinic acid (Niacin) | 4000 µg/L |
| Valine | 1 g/L | Pyridoxine | 400 µg/L |
| N-Acetyl tyrosine | 1 g/L | Thiamine | 400 µg/L |
| Methionine | 0.1 g/L | Biotin | 2 µg/L |
| Serine | 0.5 g/L | Ferric (III) chloride | 4000 µg/L |
| Threonine | 0.5 g/L | Zinc sulfate | 400 µg/L |
| Glycine | 0.1 g/L. | | |

10. A method of determining nutritional requirements of a yeast comprising:
  growing a yeast under aerobic conditions in the yeast culture medium of claim 9,
  growing the yeast under aerobic conditions in a modified yeast culture medium of claim 9 from which one structural component has been eliminated and/or reduced in concentration, and
  determining whether the elimination and/or reduction of the structural component affects the growth of the yeast.

11. A method of determining nutritional requirements of a yeast comprising:
  growing a yeast under aerobic conditions in the yeast culture medium of claim 9,
  growing the yeast under aerobic conditions in a first modified yeast culture medium of claim 9 from which a first structural component has been eliminated and/or reduced in concentration,
  determining whether the elimination and/or reduction of the first structural component affects the growth of the yeast,
  growing the yeast under aerobic conditions in a second modified yeast culture medium of claim 9 from which a second structural component has been eliminated or reduced in concentration, and
  determining whether the elimination and/or reduction of the second structural component affects the growth of the yeast.

12. A method of determining nutritional requirements of a yeast comprising:
  growing a yeast under aerobic conditions in the yeast culture medium of claim 9,
  growing the yeast under aerobic conditions in a first modified yeast culture medium of claim 9 from which a first structural component has been eliminated and/or reduced in concentration,
  growing the yeast under aerobic conditions in a second modified yeast culture medium of claim 9 from which a second structural component has been eliminated or reduced in concentration,
  determining whether the elimination and/or reduction of the first structural component affects the growth of the yeast,
  determining whether the elimination and/or reduction of the second structural component affects the growth of the yeast, and
  ranking the first structural component and second structural component by the growth of the yeast.

* * * * *

UNITED STATES PATENT AND TRADEMARK OFFICE
CERTIFICATE OF CORRECTION

PATENT NO. : 10,023,836 B2
APPLICATION NO. : 14/423292
DATED : July 17, 2018
INVENTOR(S) : R. Akada Page 1 of 1

It is certified that error appears in the above-identified patent and that said Letters Patent is hereby corrected as shown below:

In the Claims

At Column 39, Line 15 (Claim 8, Line 2), please change "comprises" to -- comprise --.

Signed and Sealed this
Fifteenth Day of January, 2019

Andrei Iancu
*Director of the United States Patent and Trademark Office*